(12) United States Patent
Mei

(10) Patent No.: US 10,358,455 B2
(45) Date of Patent: Jul. 23, 2019

(54) ARENE RUTHENIUM COMPLEX, PREPARATION METHOD AND UTILIZATION THEREOF

(71) Applicant: Guangdong Pharmaceutical University, Guangzhou (CN)

(72) Inventor: Wenjie Mei, Guangzhou (CN)

(73) Assignee: GUANGDONG PHARMACEUTICAL UNIVERSITY, Guangzhou (CN)

( * ) Notice: Subject to any disclaimer, the term of this patent is extended or adjusted under 35 U.S.C. 154(b) by 0 days.

(21) Appl. No.: 15/947,865

(22) Filed: Apr. 9, 2018

(65) Prior Publication Data

US 2018/0334473 A1 Nov. 22, 2018

(30) Foreign Application Priority Data

May 19, 2017 (CN) .................... 2017 1 03607965

(51) Int. Cl.
- *C07F 15/00* (2006.01)
- *A61P 35/00* (2006.01)

(52) U.S. Cl.
CPC .......... *C07F 15/0046* (2013.01); *A61P 35/00* (2018.01); *C07F 15/0053* (2013.01)

(58) Field of Classification Search
CPC ................................................ C07F 15/0046
USPC ......................................................... 546/10
See application file for complete search history.

(56) References Cited

U.S. PATENT DOCUMENTS

| 8,357,678 B2 * | 1/2013 | Mei .................... C07F 15/0053 514/185 |
| 2017/0056525 A1 * | 3/2017 | Mei .................... C07F 15/0053 546/10 |

FOREIGN PATENT DOCUMENTS

CN    102898480 A  * 1/2013 .......... C07F 15/0046

OTHER PUBLICATIONS

Zhang, Q-L. et al.: DNA-binding and photoactivated enantiospecific cleavage of chiral polypyridyl ruthenium (II) complexes. Journal of Inorganic Biochem., vol. 98, pp. 1405-1412, 2004.*

(Continued)

*Primary Examiner* — Charanjit Aulakh
(74) *Attorney, Agent, or Firm* — Gokalp Bayramoglu

(57) ABSTRACT

Disclosed is an arene ruthenium complex with $R_1$, $R_2$, $R_3$, and piperidine as main ligands, preparation method and utilization thereof. $R_1$, $R_2$, $R_3$ are selected from —H, —Cl, —F, —Br, —I, —CF$_3$, —NO$_2$, —OCH$_3$, —OH, —COOH, —CH$_3$, —N(CH$_3$)$_2$, —C$_2$H$_2$, —SO$_2$CH$_3$, alkane with 1 to 6 carbon atoms, substituted alkyl with 1 to 6 carbon atoms, phenyl, substituted phenyl, pyridyl, substituted pyridyl, furyl, substituted furyl, pyrrolyl, substituted pyrrolyl, thiazyl or substituted thiazyl group respectively. The substituted groups in the substituted phenyl, substituted pyridyl, substituted furyl, substituted thiazyl and substituted pyrrolyl are selected from hydroxyl, nitro, halogen, amido, carboxyl, cyano, thiol or naphthene group with 3 to 8 carbon atoms, SO$_3$H, alkane with 1 to 6 carbon atoms, alkenyl with 2 to 6 carbon atoms, alkyne with 2 to 6 carbon atoms, $C_1$-$C_6$ hydroxyalkane, $C_1$-$C_6$ aminoalkane, CO$_2$R', CONR'R', COR', SO$_2$R'R', $C_1$-$C_6$ alkoxyl, $C_1$-$C_6$ alkyl thiol, —N=NR', NR'R' or $C_1$-$C_6$ trifloroalkyl.

3 Claims, 75 Drawing Sheets

(56) References Cited

OTHER PUBLICATIONS

Karlsson, S. et al.: Accumulative charge separation inspired by photosynthesis. J. Am. Chem. Soc., vol. 132, pp. 17977-17979 as well as supporting informatio, 2010.*

Y.N. Vashisht Gopal et al. "Topoisomerase II antagonism and anticancer activity of coordinated derivatives of [RuCl2(C6H6)(dmso)]", Archives of Biochemistry and Biophysics 401 (2002) 53-62.

Claudine Scolaro et al. "In Vitro and in Vivo Evaluation of Ruthenium(II)-Arene PTA Complexes", J. Med. Chem. 2005, 48, 4161-4171.

Soumya Chatterjee et al. "The ruthenium(II)-arene compound RAPTA-C induces apoptosis in EAC cells through mitochondrial and p53—JNK pathways", J Biol Inorg Chem ,2008,13:1149-1155.

Patrycja Nowak-Sliwinska et al. "Organometallic Ruthenium(II) Arene Compounds with Antiangiogenic Activity", J. Med. Chem. 2011, 54, 3895-3902.

Robert E. Morris et al. "Inhibition of Cancer Cell Growth by Ruthenium(II) Arene Complexes", J. Med. Chem. 2001, 44, 3616-3621.

A. Bergamo et al. "In vivo tumour and metastasis reduction and in vitro effects on invasion assays of the ruthenium RM175 and osmium AFAP51 organometallics in the mammary cancer model", Journal of Inorganic Biochemistry 104 (2010) 79-86.

Abraha Habtemariam et al. "Structure-Activity Relationships for Cytotoxic Ruthenium(II) Arene Complexes Containing N,N-, N,O-, and O,O-Chelating Ligands", J. Med. Chem. 2006, 49, 6858-6868.

Liang He et al. "Ruthenium—Arene—β-Carboline Complexes as Potent Inhibitors of Cyclin-Dependent Kinase 1: Synthesis, Characterization and Anticancer Mechanism Studies", Chem. Eur. J, 2013, 19, 12152-12160.

Wei Su et al. "Synthesis, crystal and electronic structure, anticancer activity of ruthenium(II) arene complexes with thiosemicarbazones", Appl. Organometal. Chem. (2013), 27(5): 307-312.

* cited by examiner

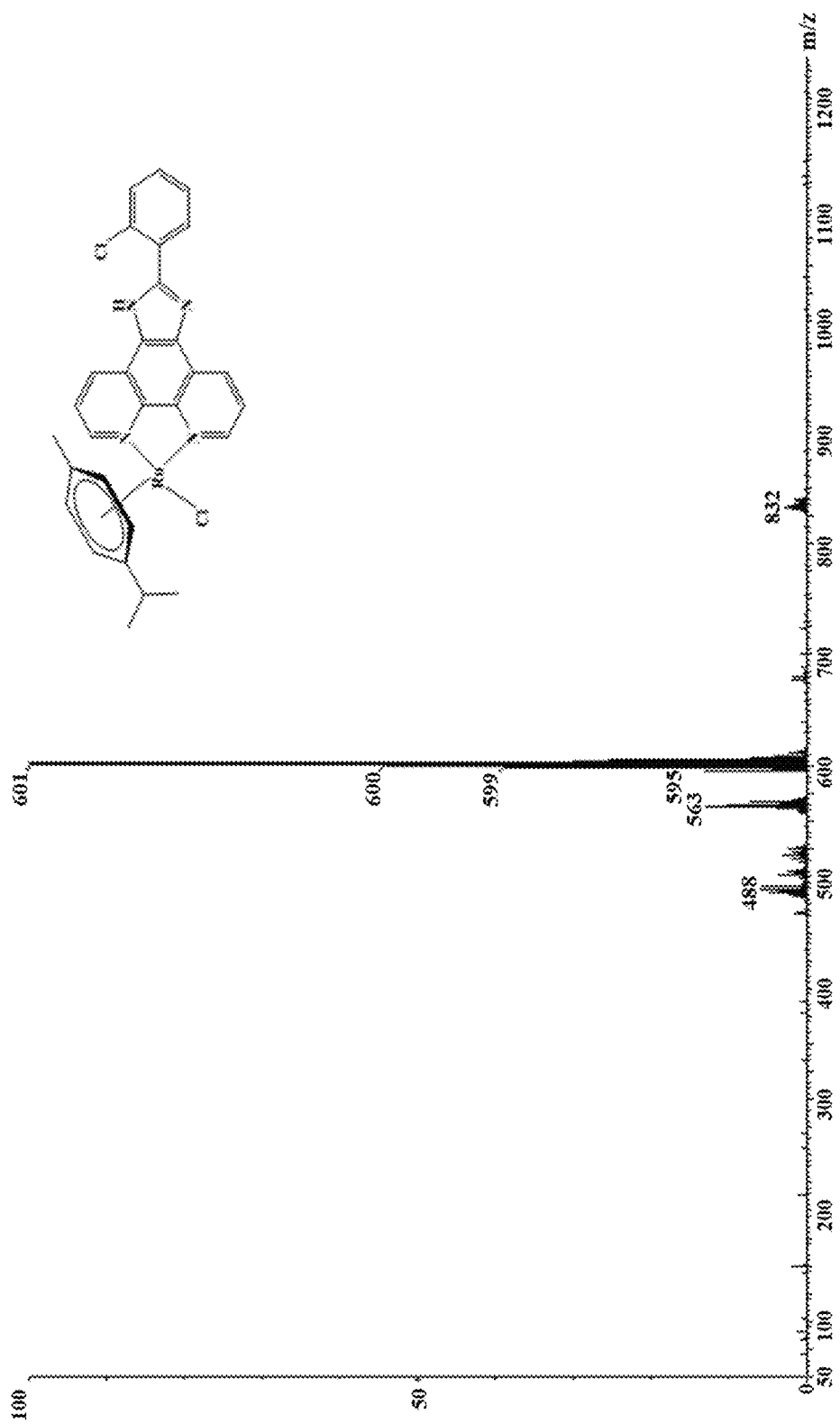
Figure 1 The ESI-MS spectra of RAP051

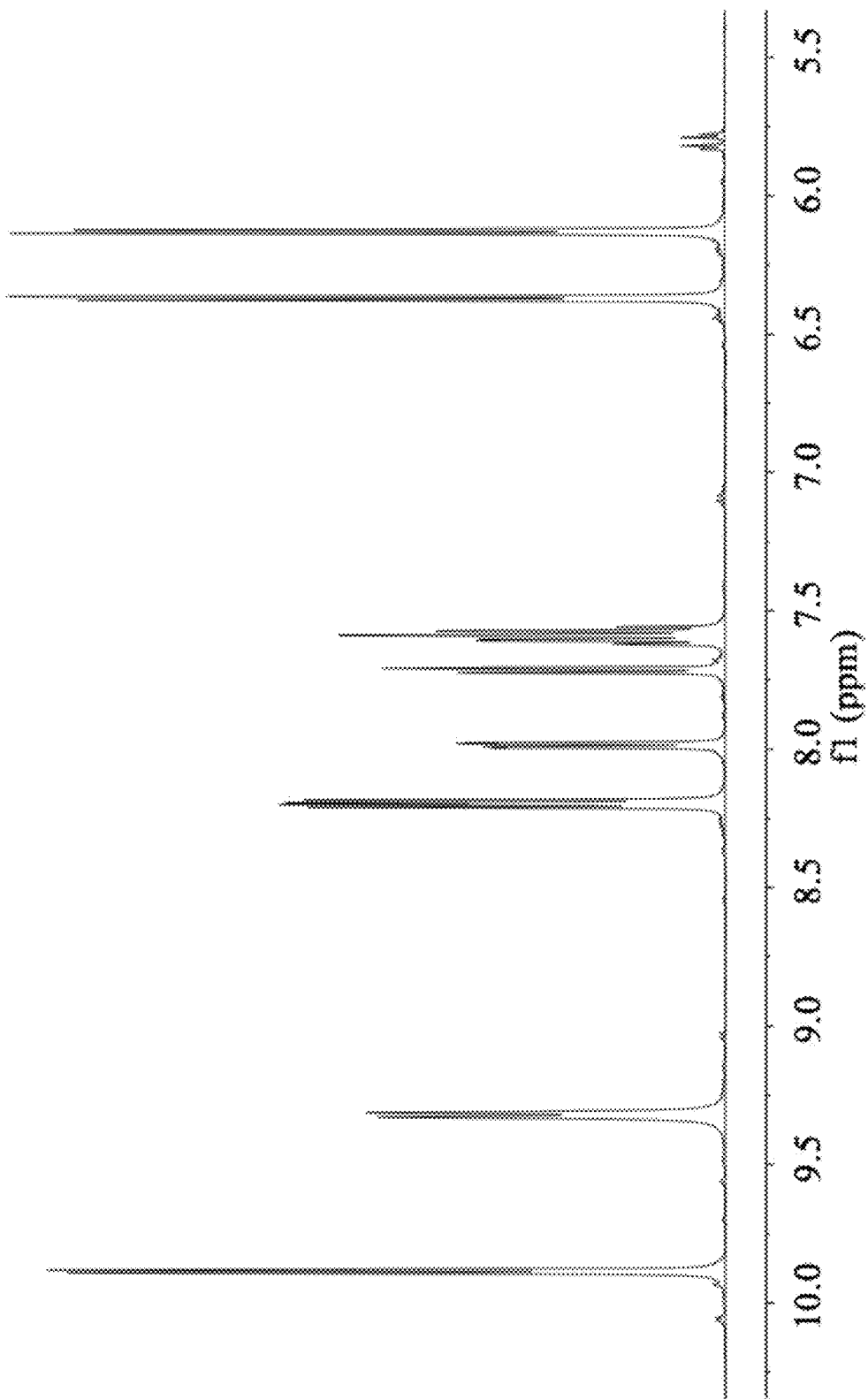
Figure 2 The $^1$H NMR spectra of RAP051

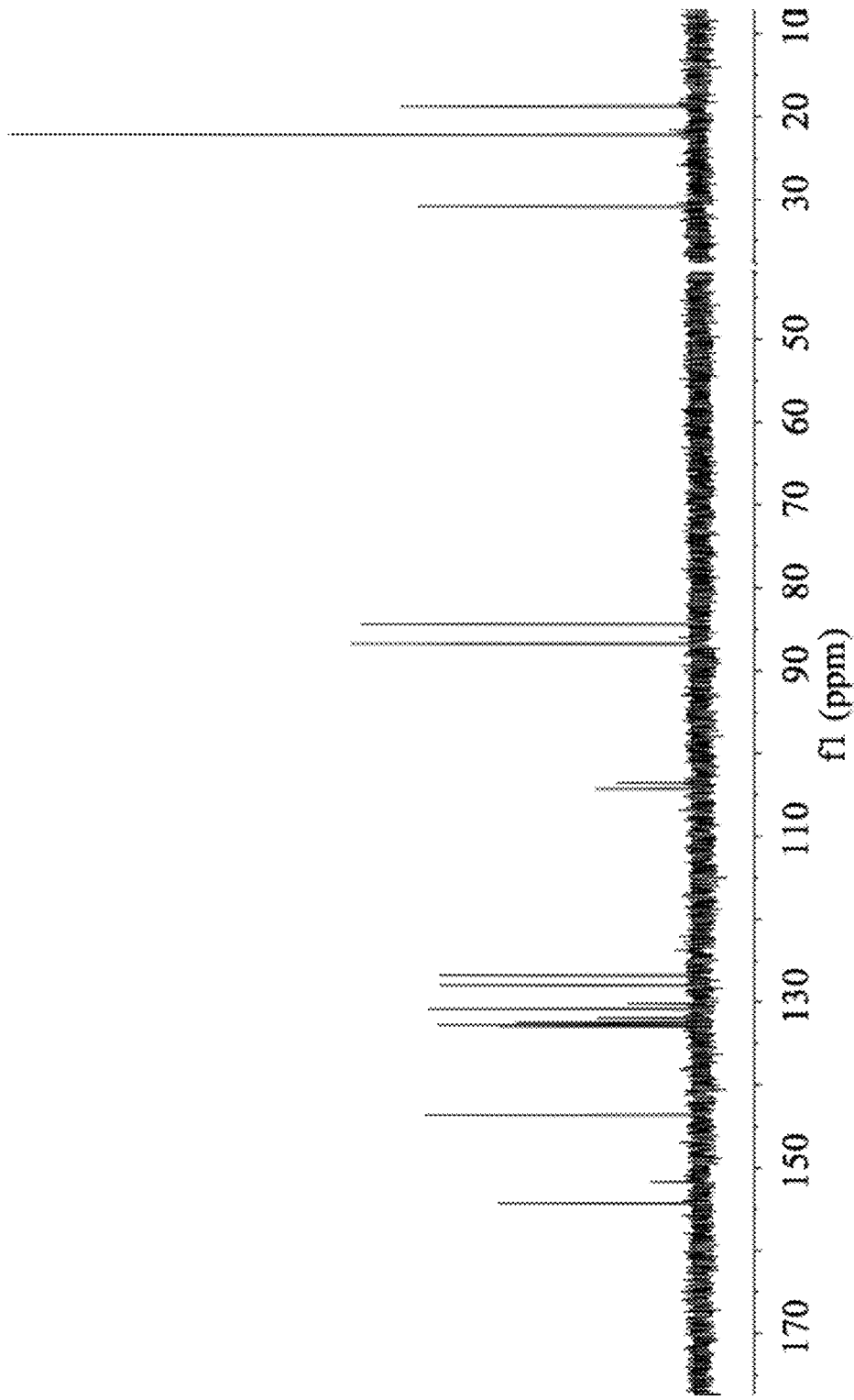
Figure 3 The ¹³C NMR spectra of RAP051

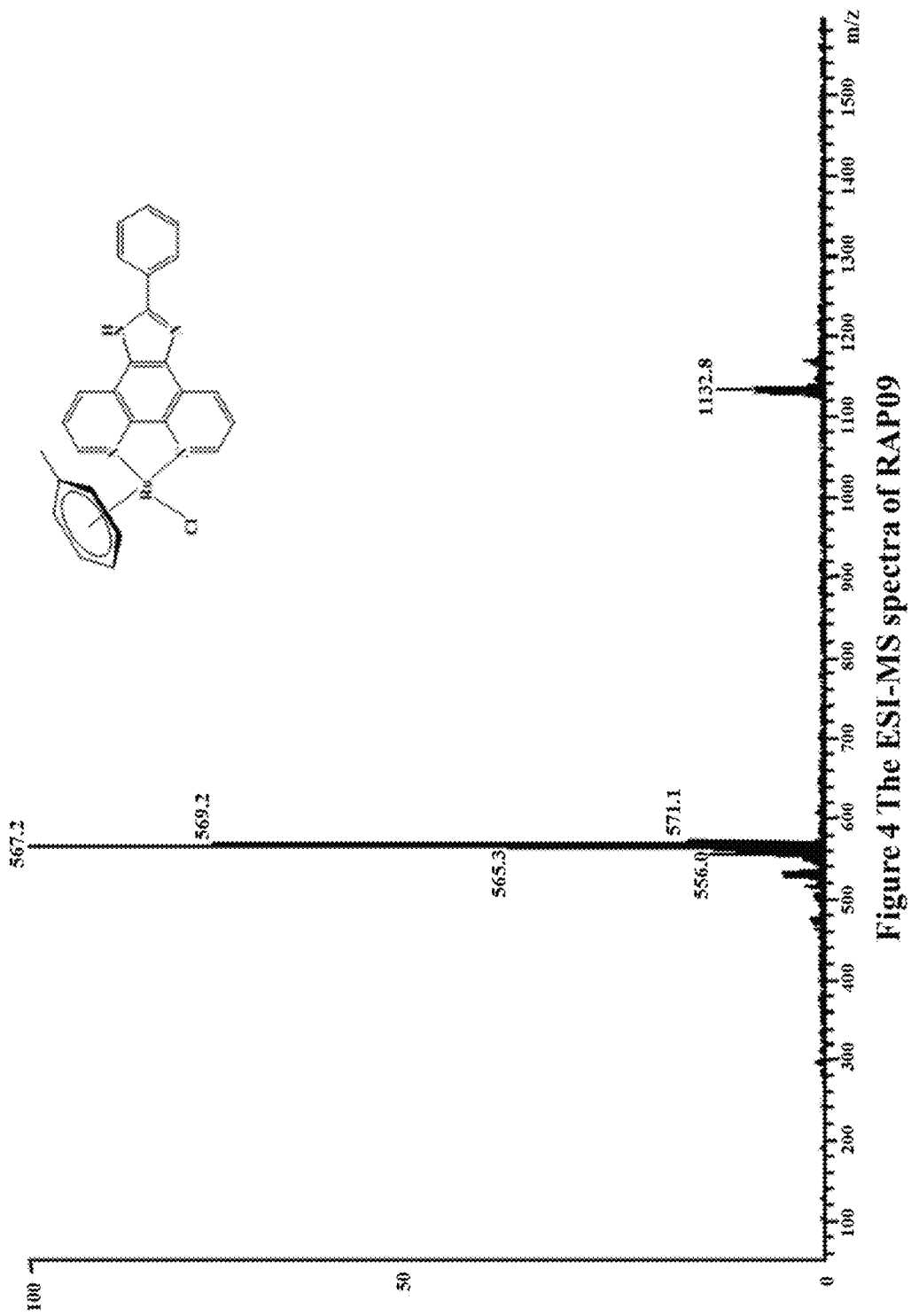
Figure 4 The ESI-MS spectra of RAP09

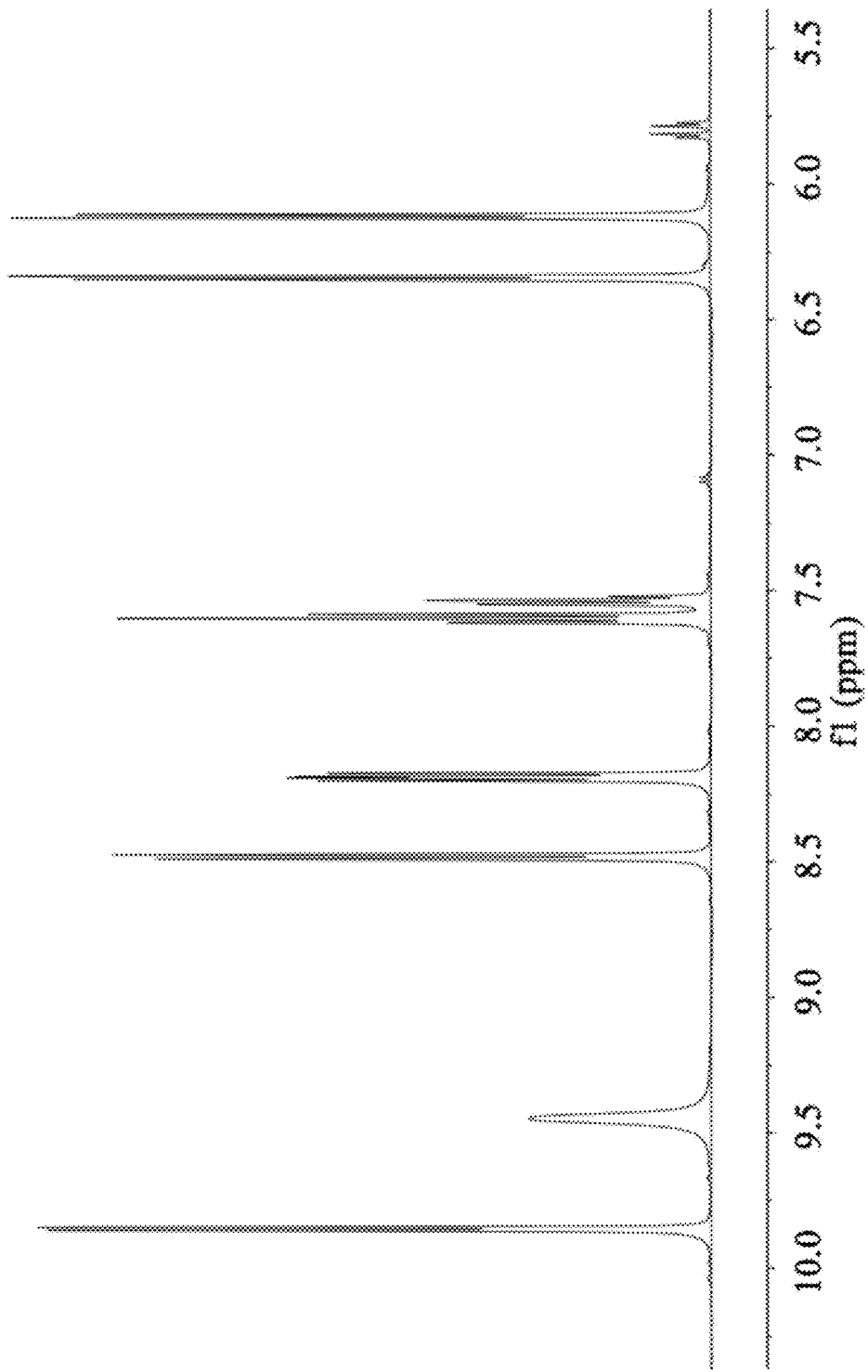

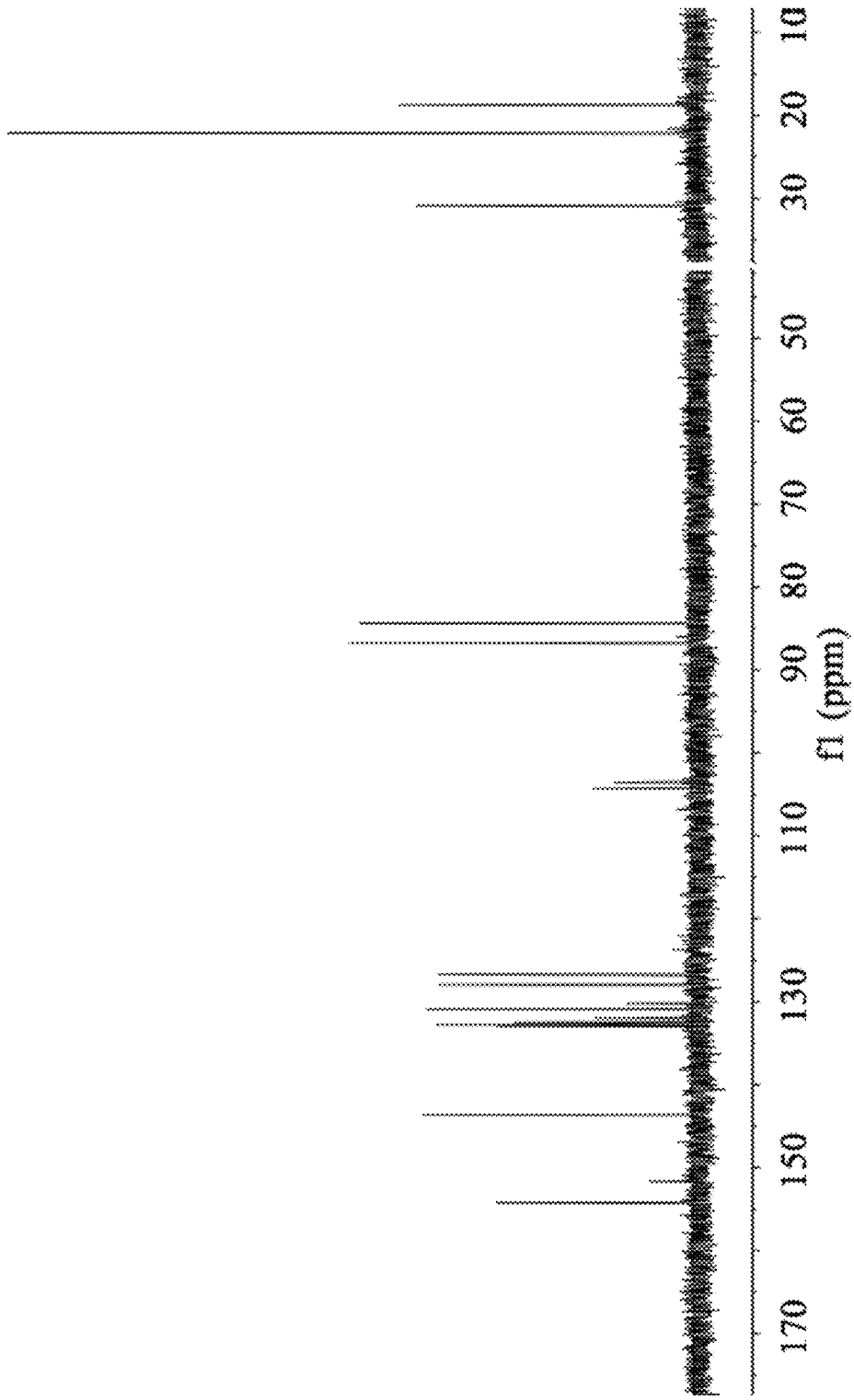
Figure 6 The $^{13}C$ NMR spectra of RAP09

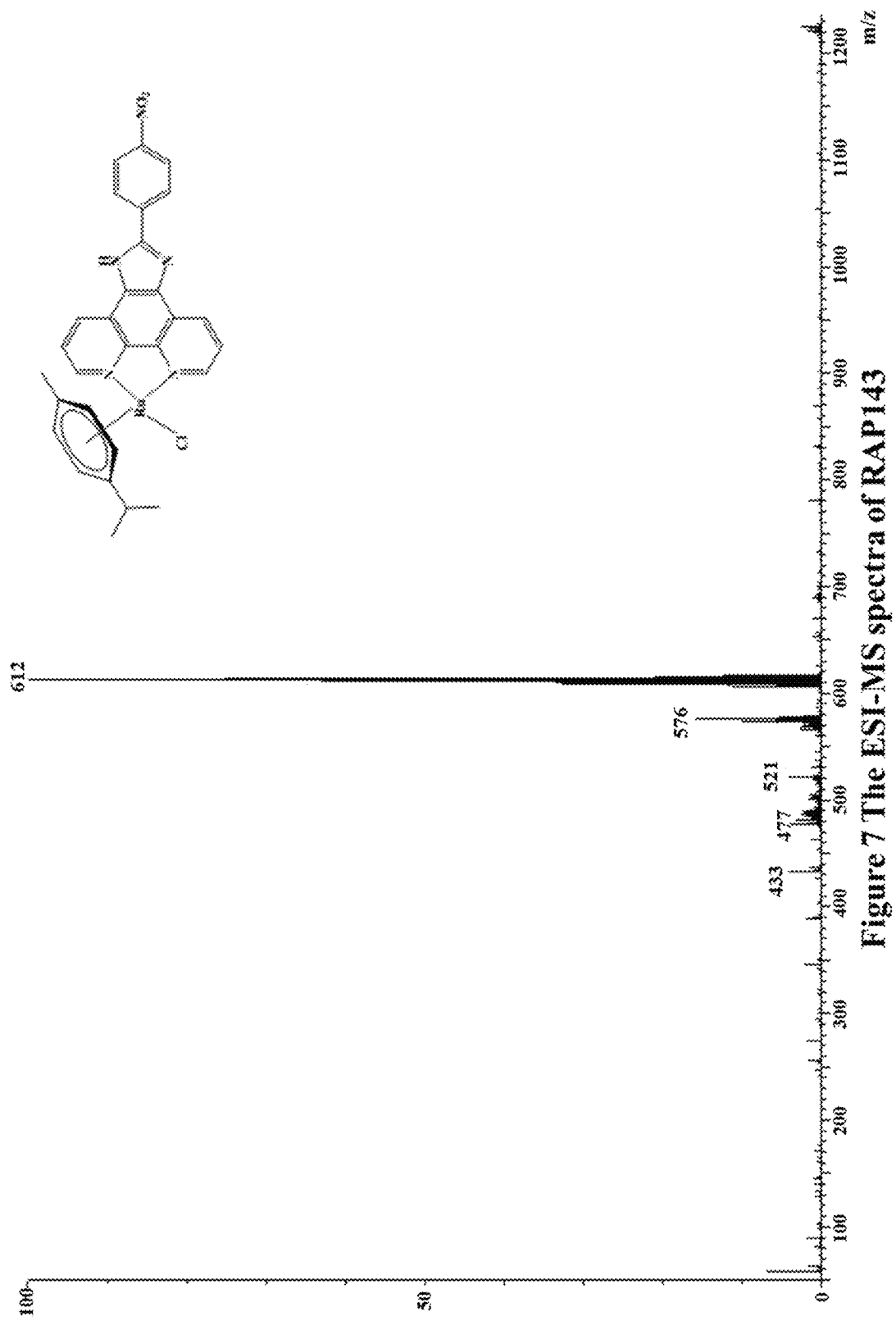
Figure 7 The ESI-MS spectra of RAP143

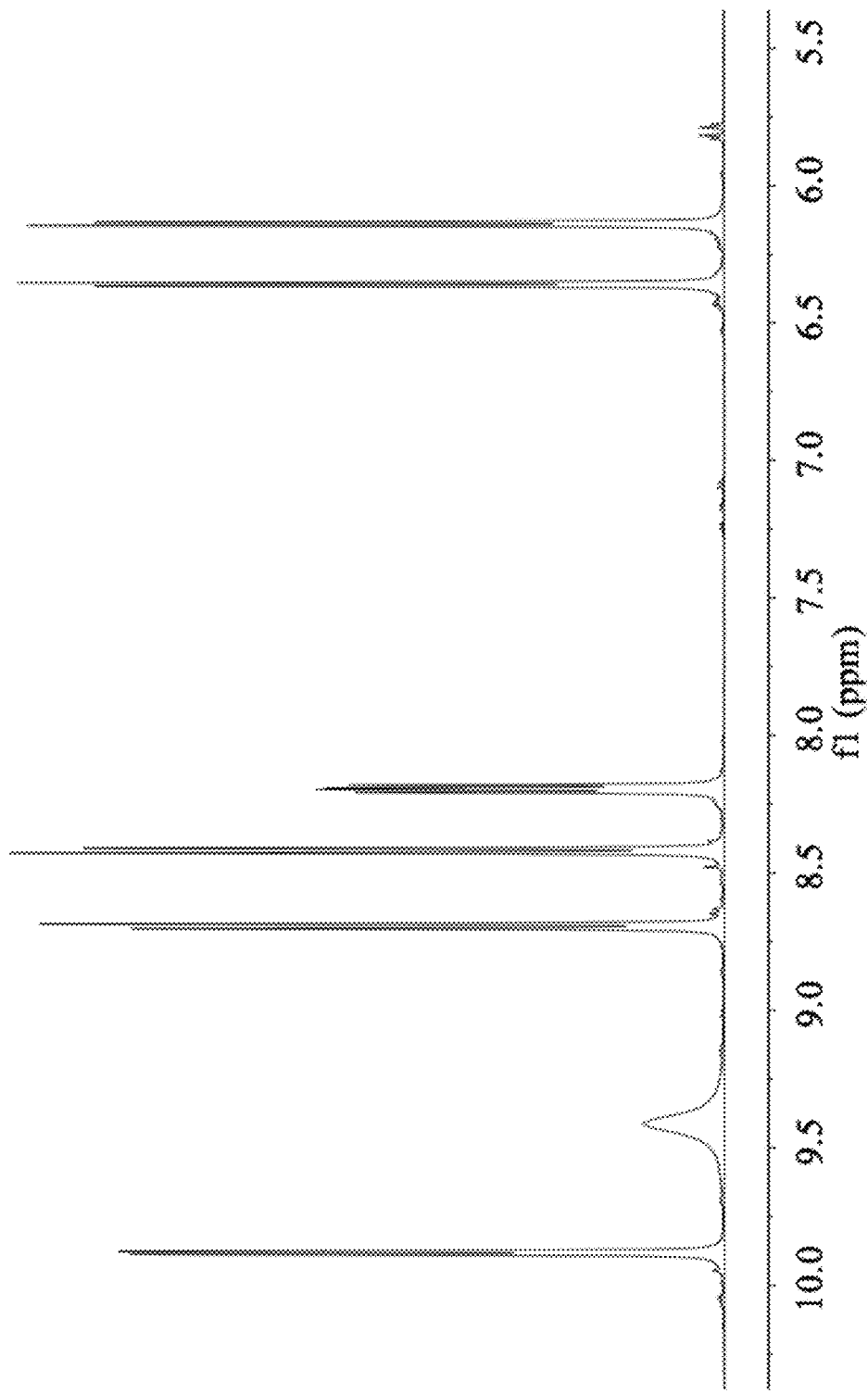
Figure 8 The $^1$H NMR spectra of RAP143

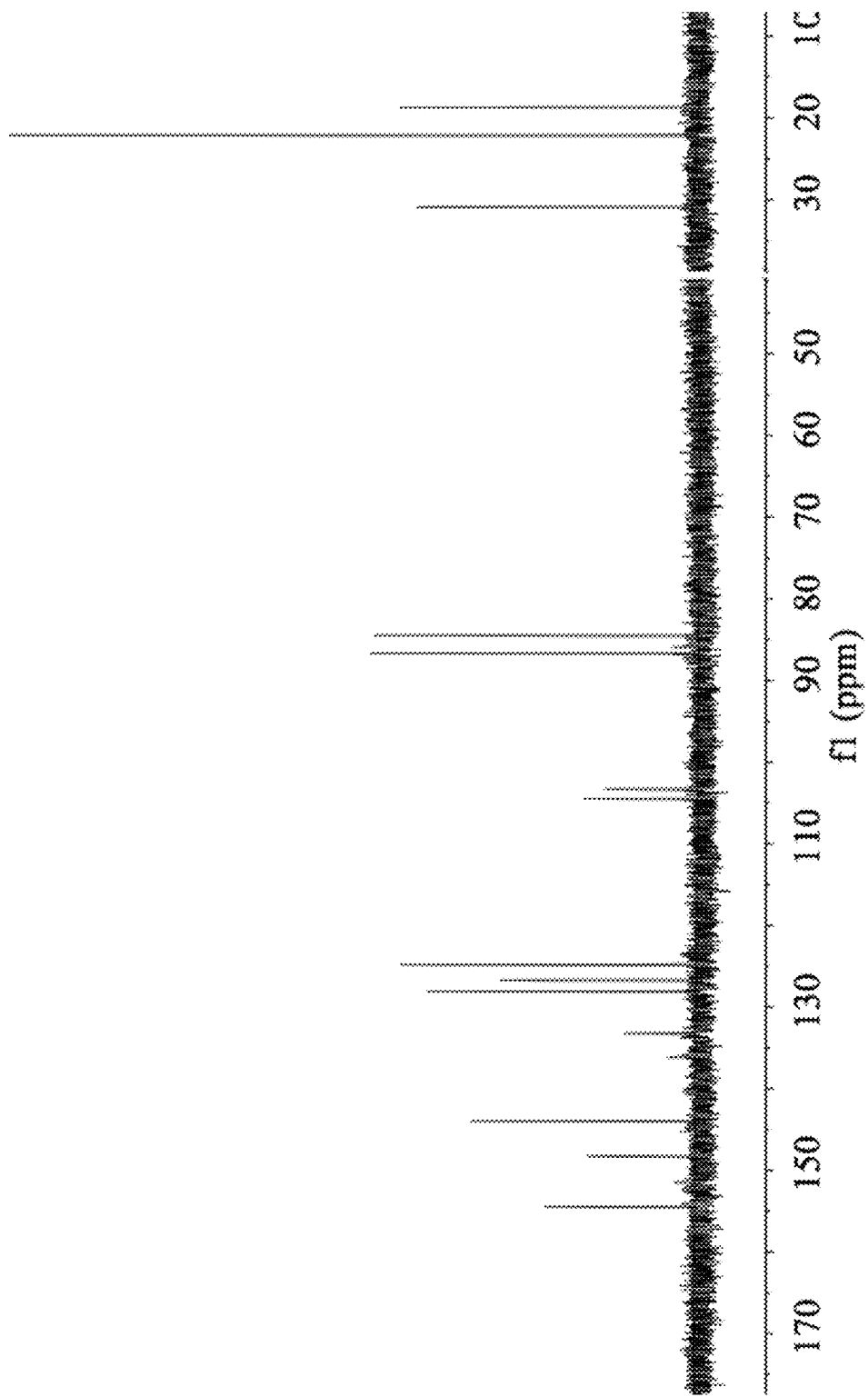
Figure 9 The ¹³C NMR spectra of RAP143

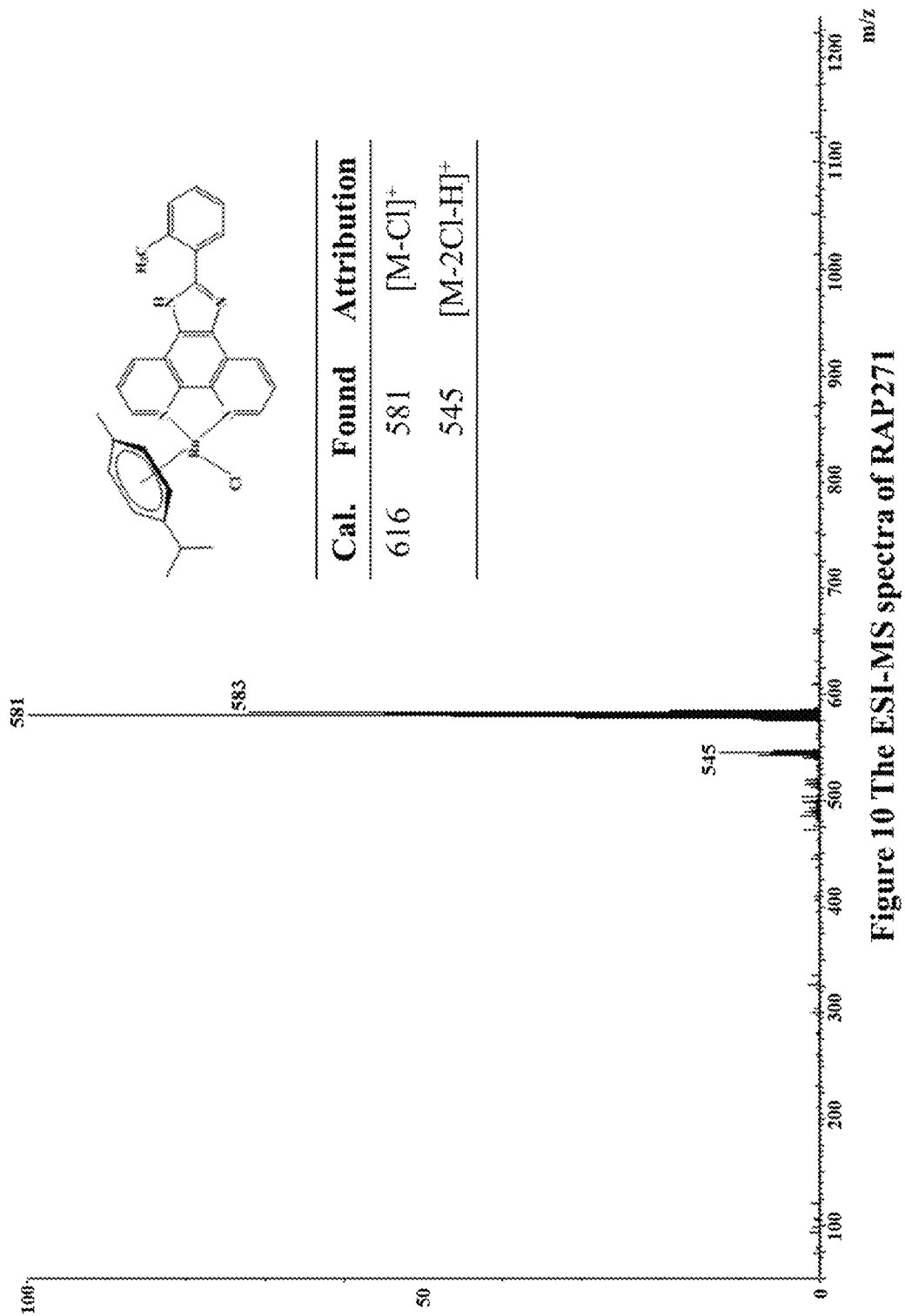
Figure 10 The ESI-MS spectra of RAP271

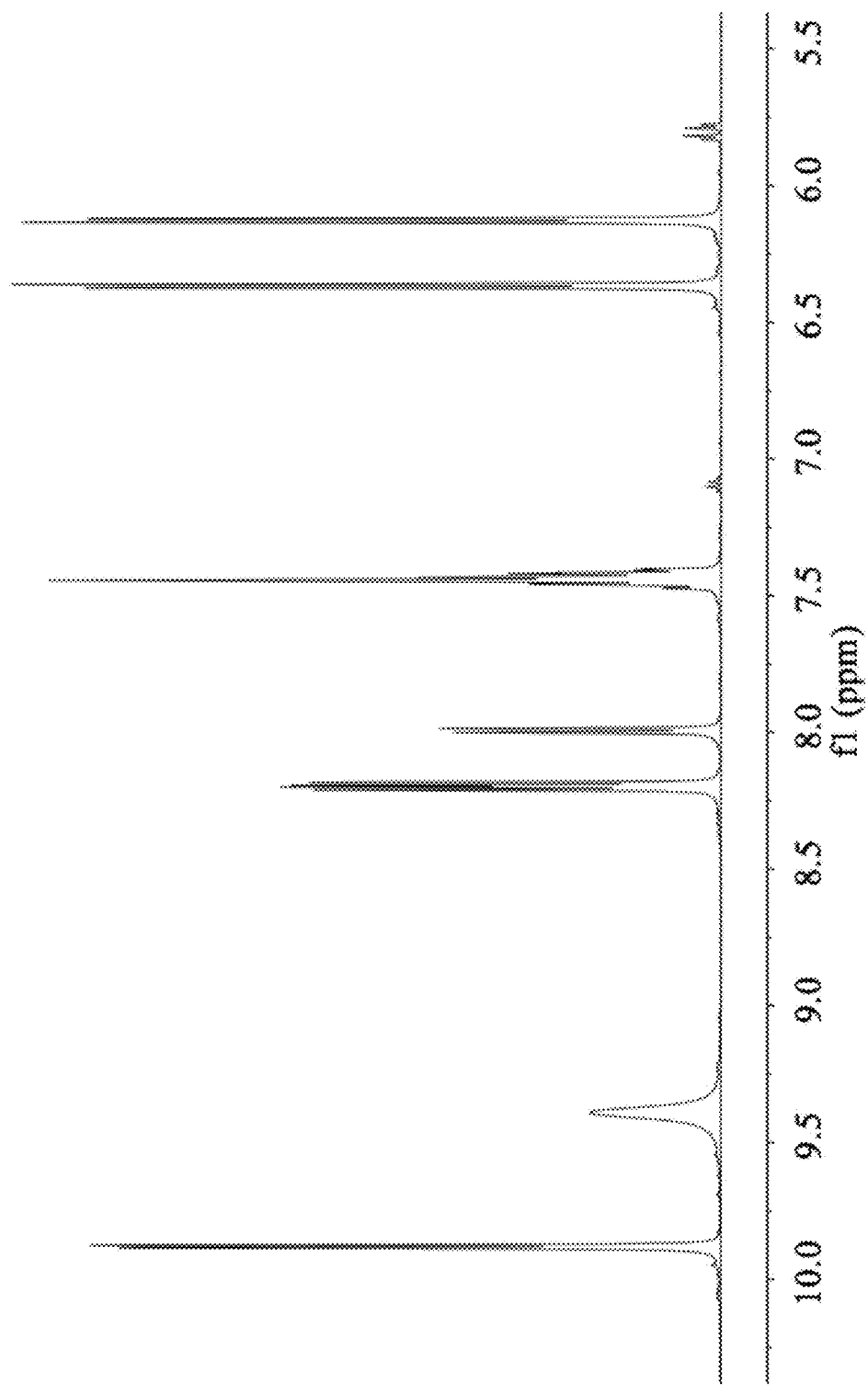
Figure 11 The $^1$H NMR spectra of RAP271

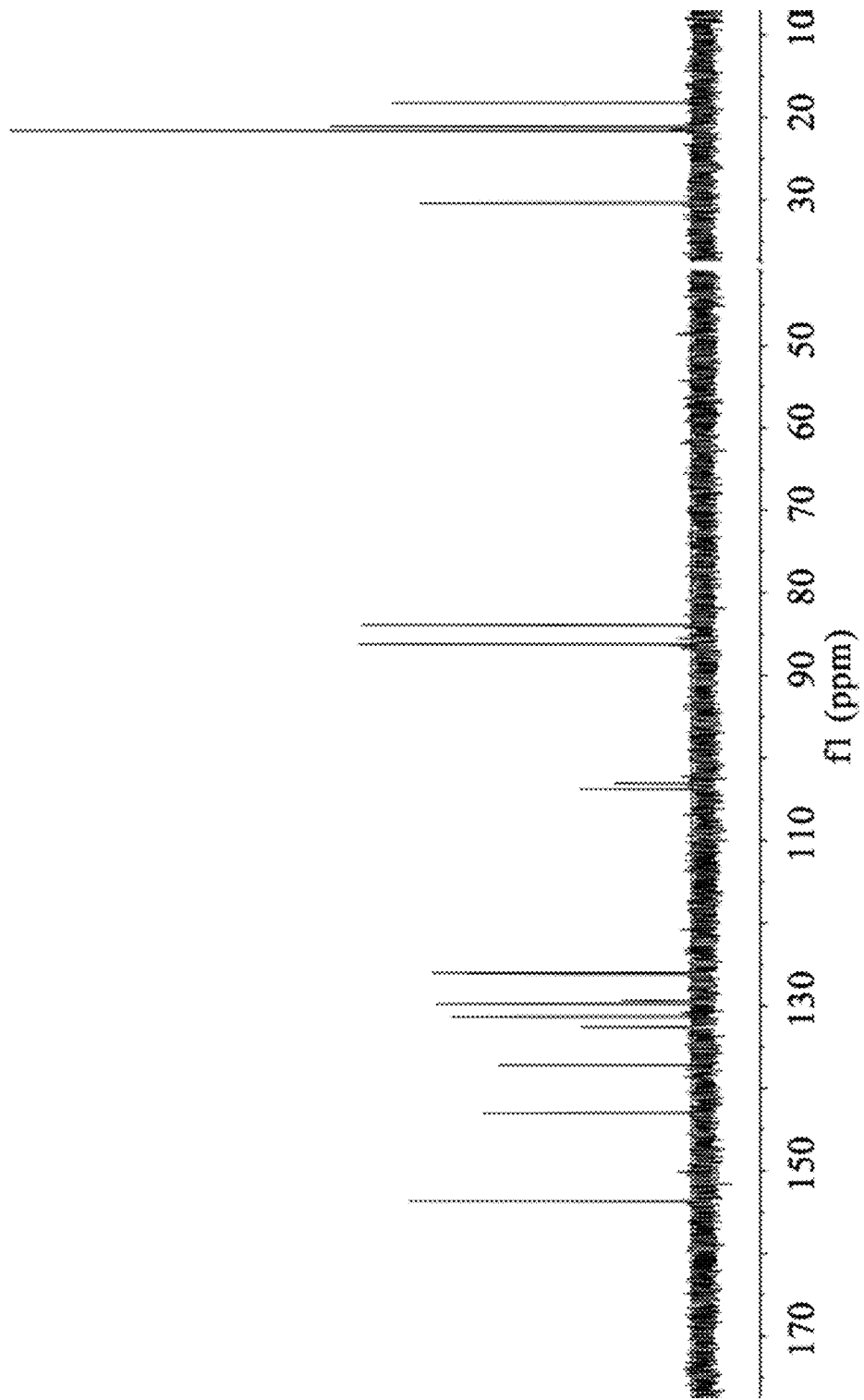
Figure 12 The $^{13}C$ NMR spectra of RAP271

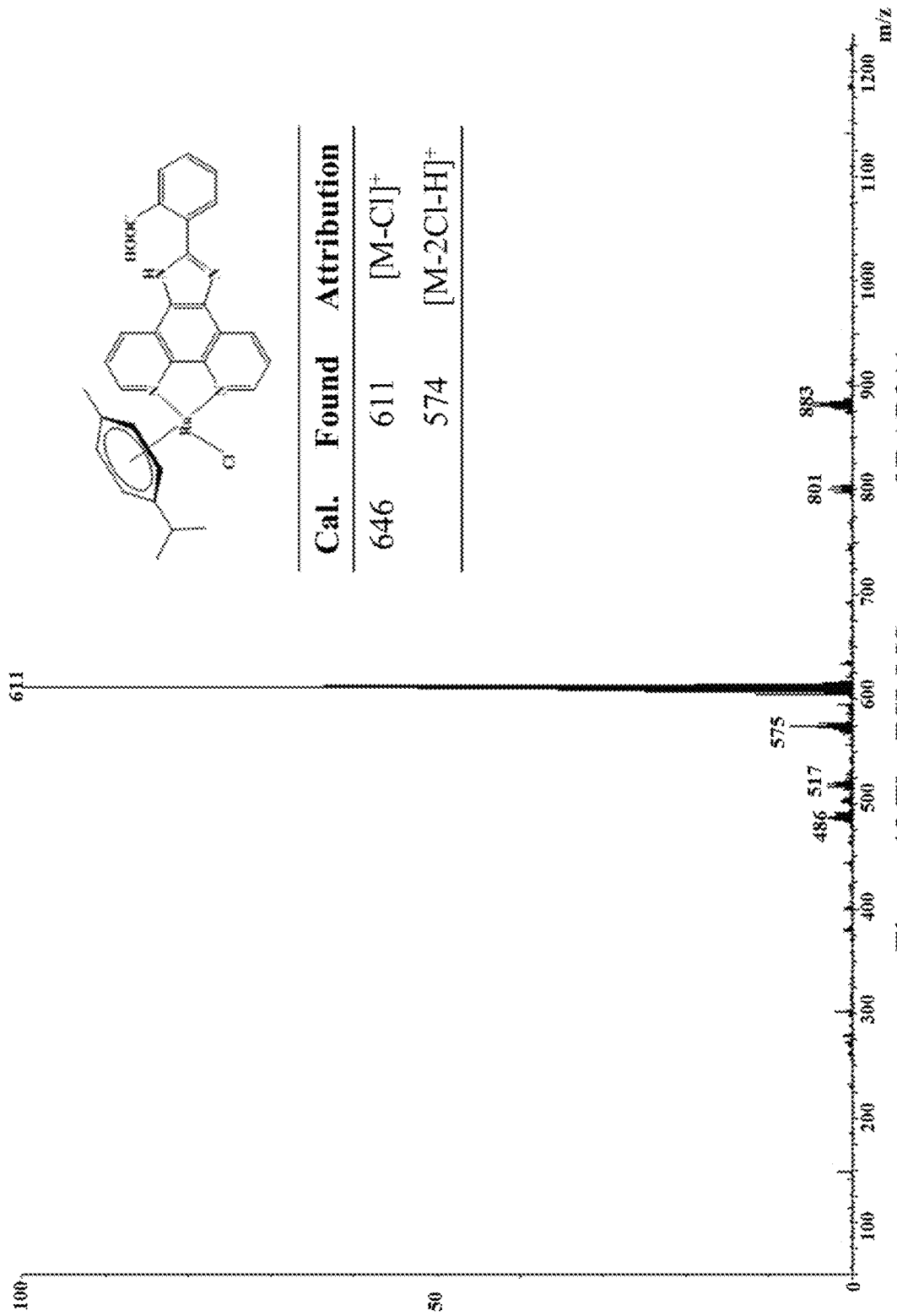
Figure 13 The ESI-MS spectra of RAP211

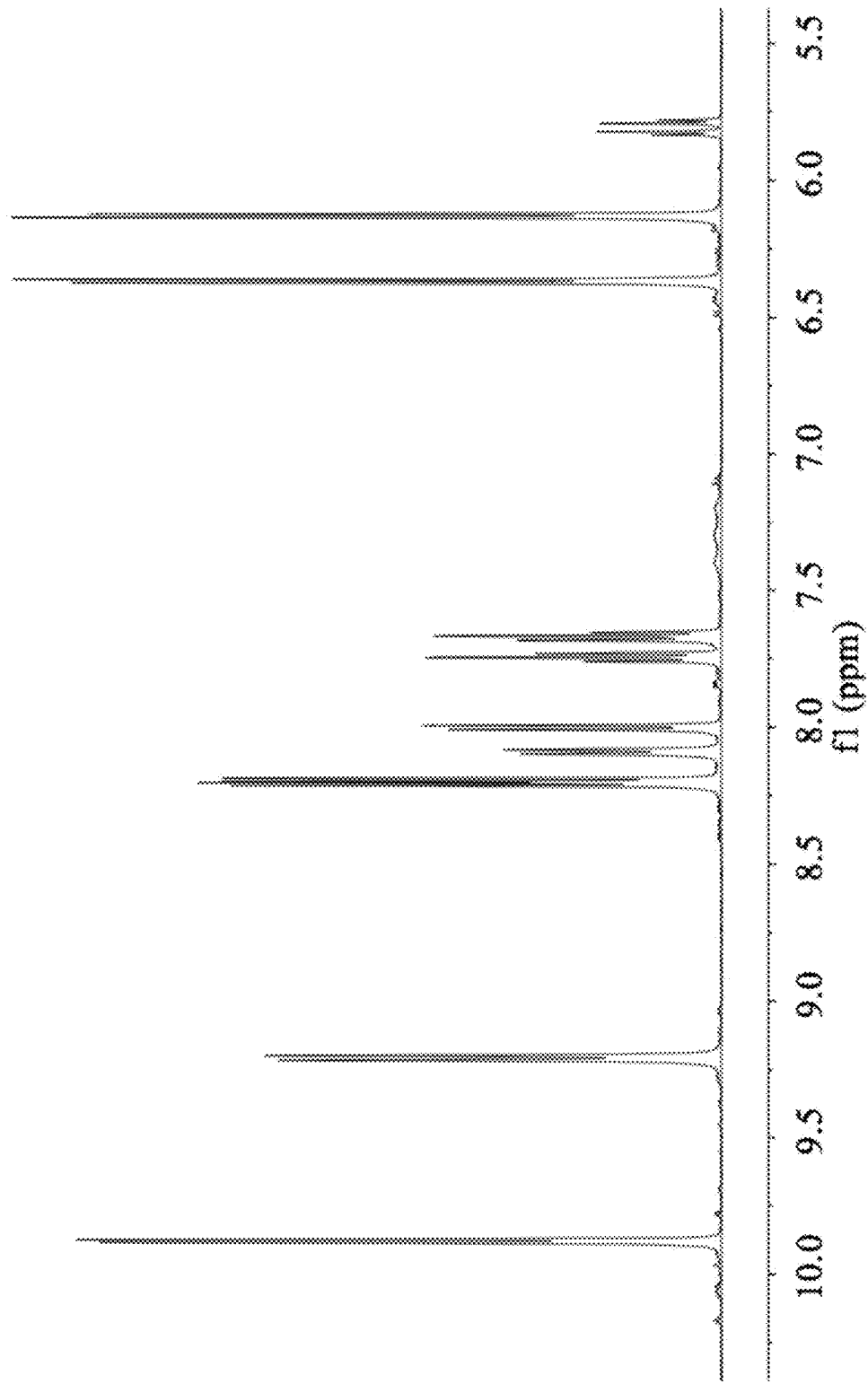
Figure 14 The $^1$H NMR spectra of RAP211

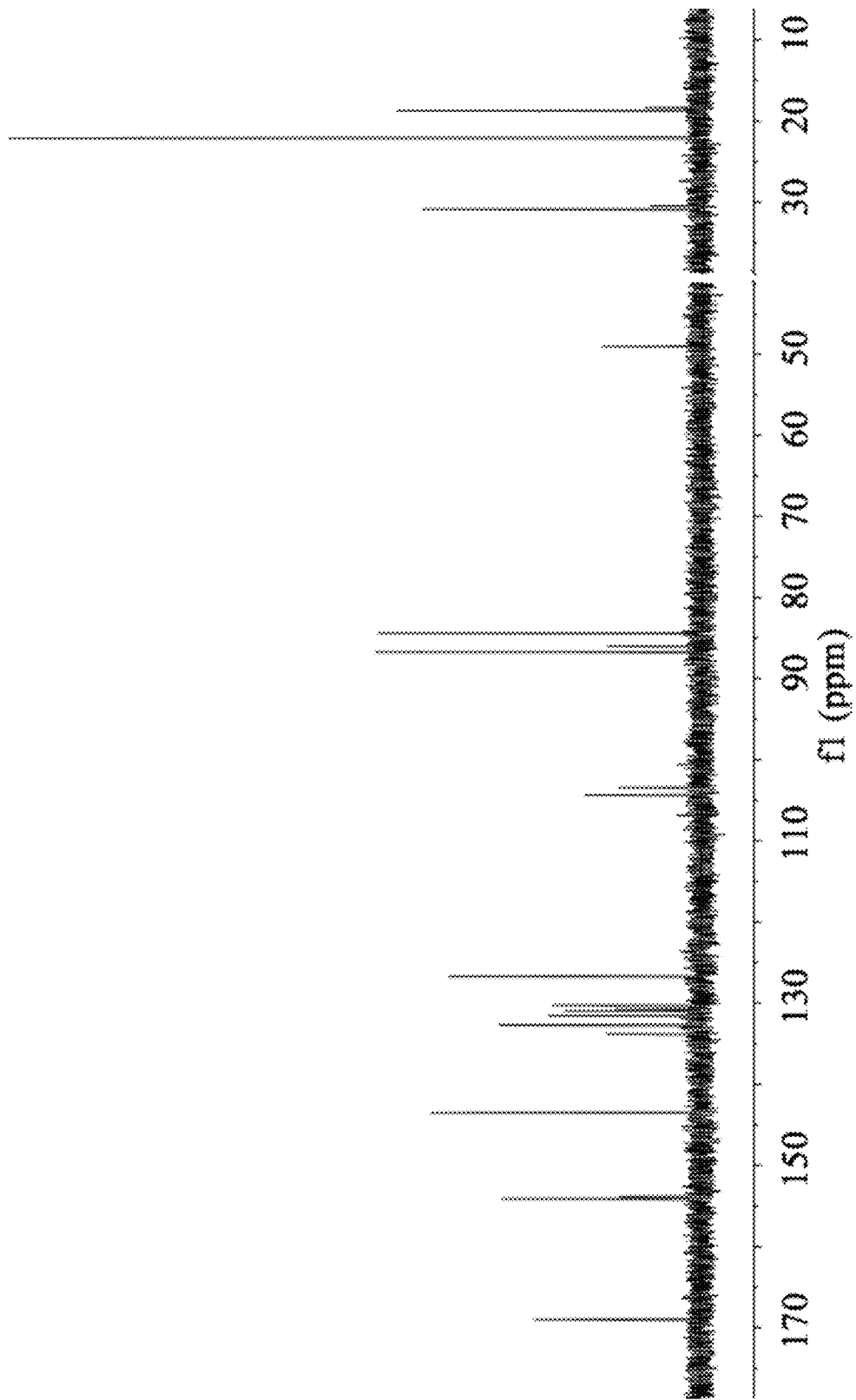
Figure 15 The $^{13}C$ NMR spectra of RAP211

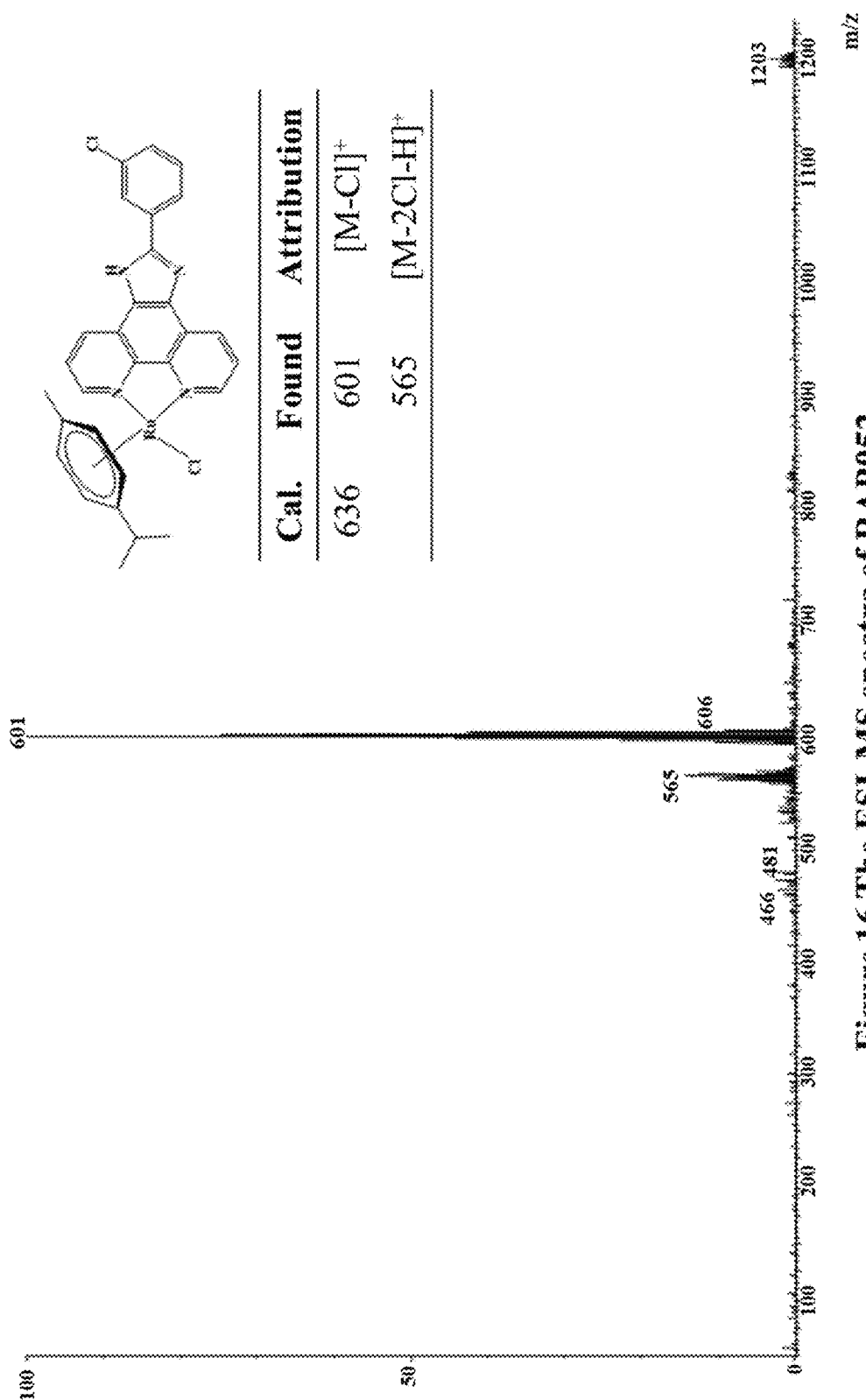
Figure 16 The ESI-MS spectra of RAP052

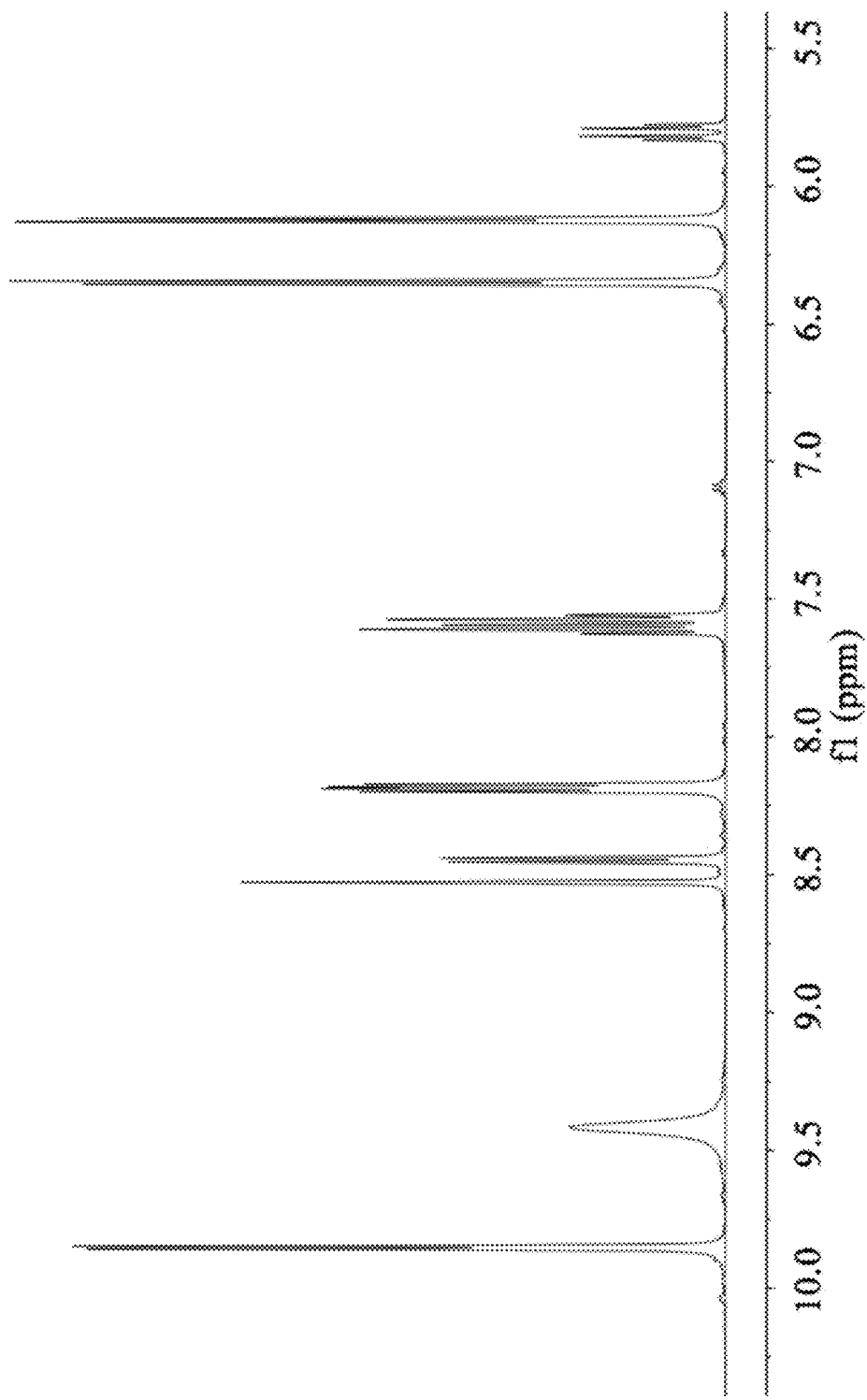
Figure 17 The $^1$H NMR spectra of RAP052

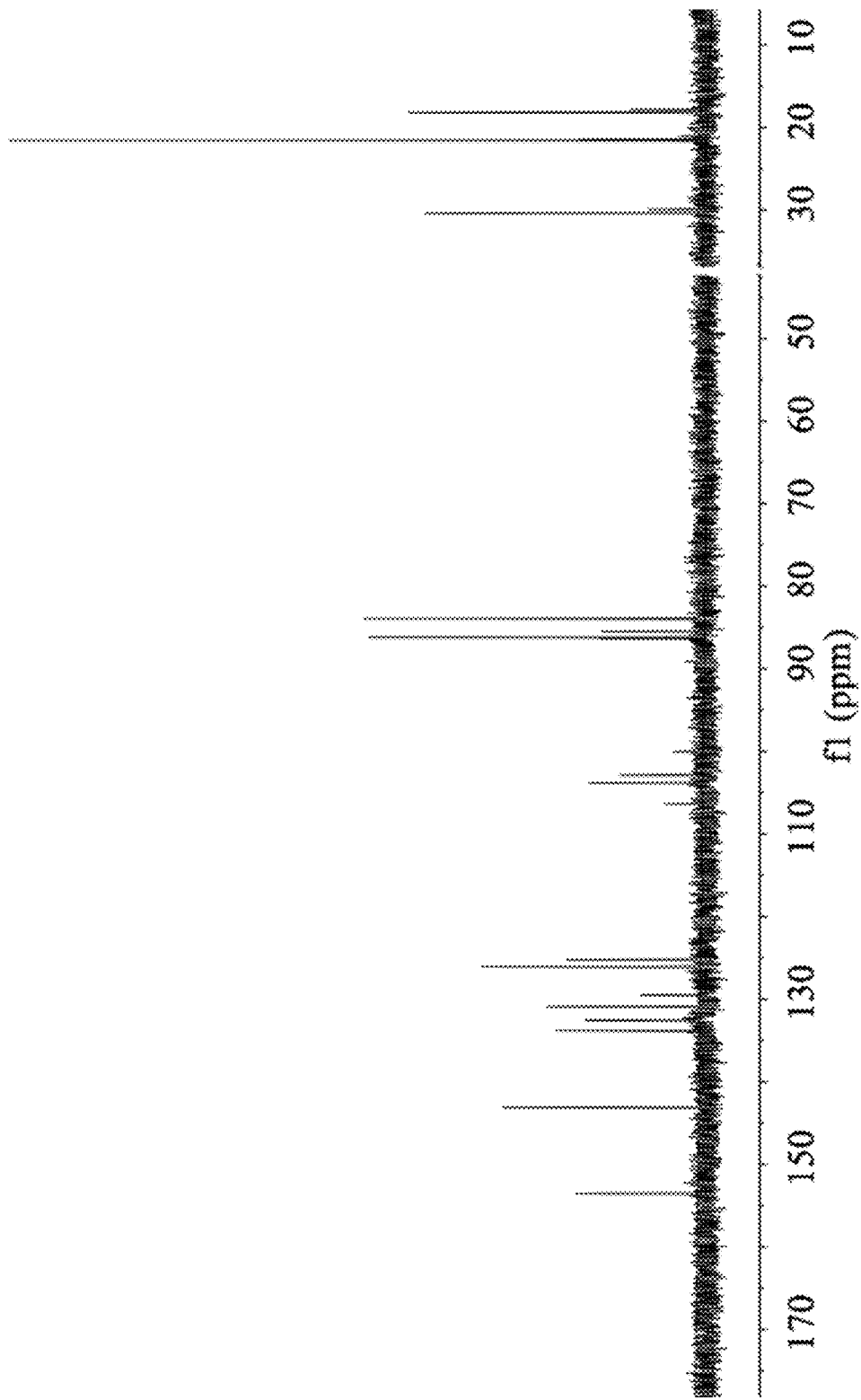
Figure 18 The $^{13}$C NMR spectra of RAP052

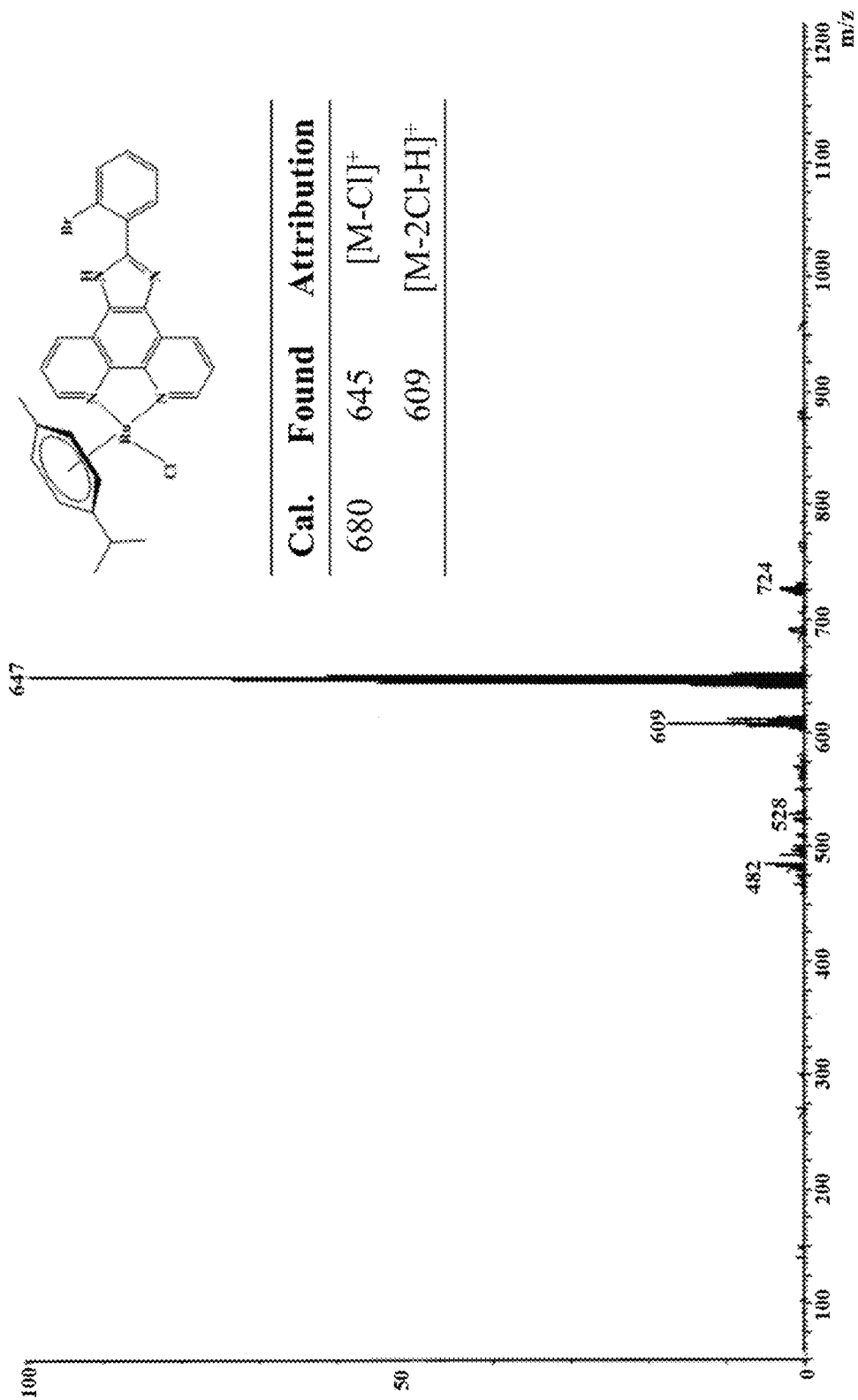
Figure 19 The ESI-MS spectra of RAP061

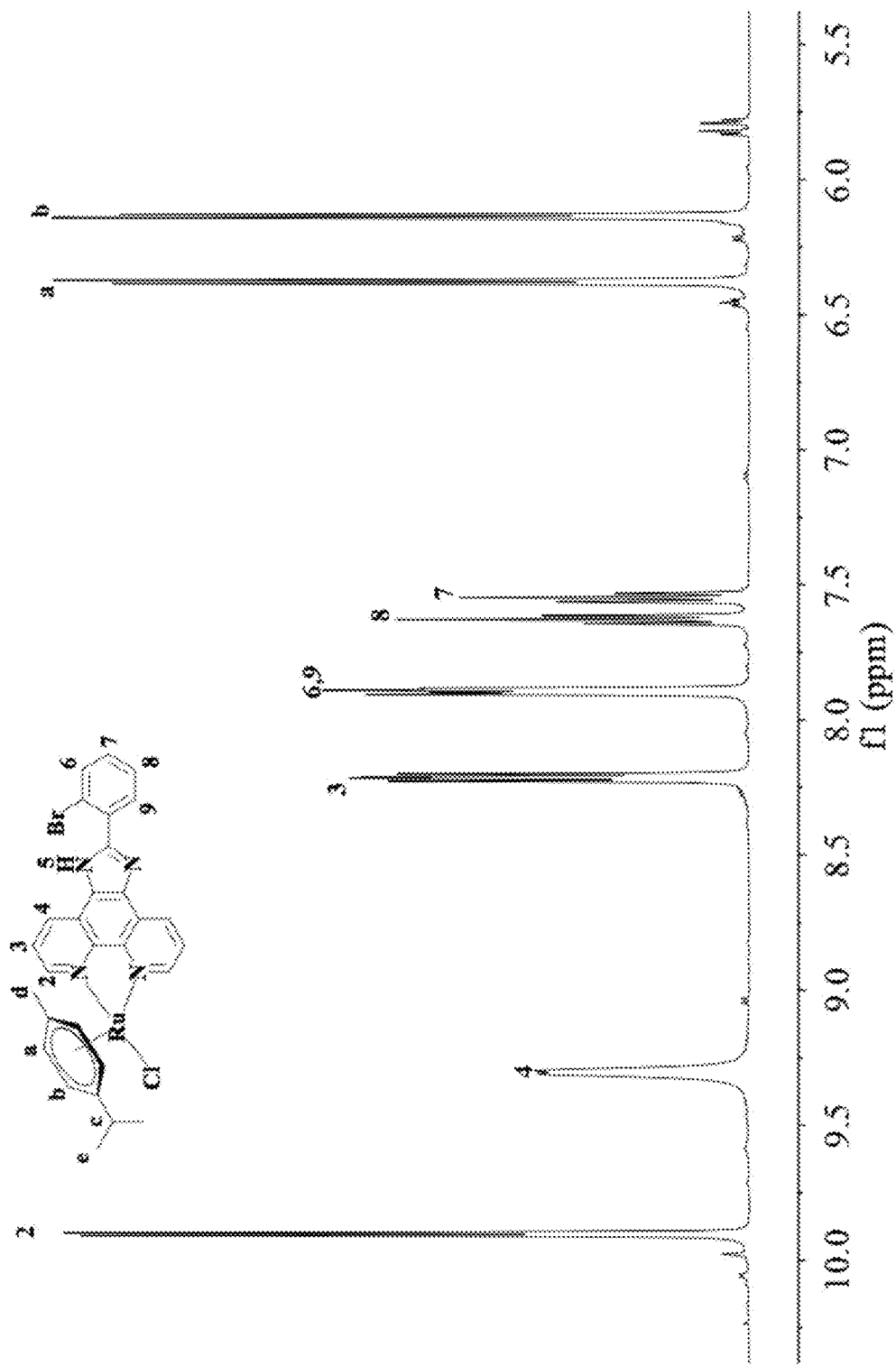
Figure 20 The $^1$H NMR spectra of RAP061

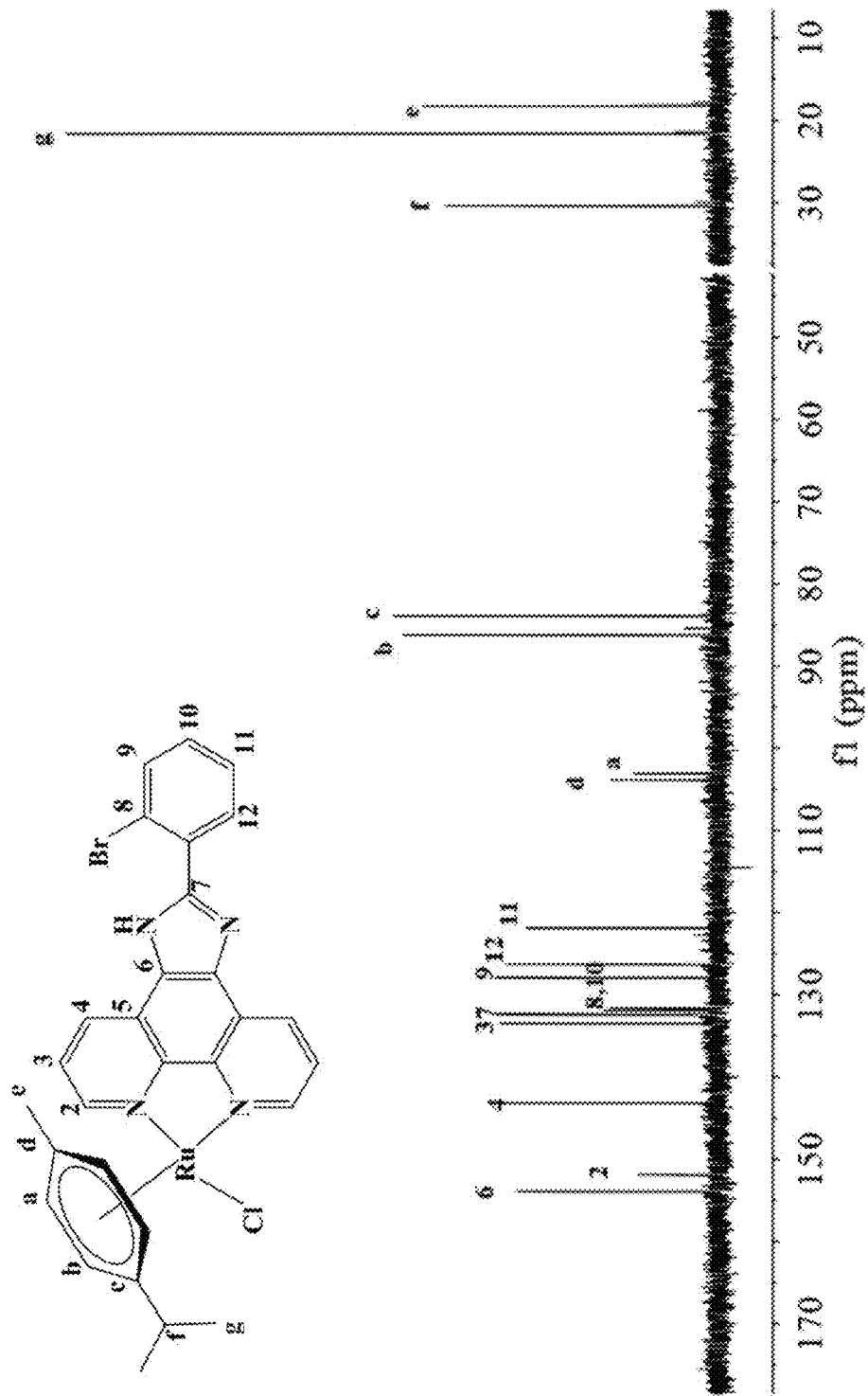
Figure 21 The $^{13}$C NMR spectra of RAP061

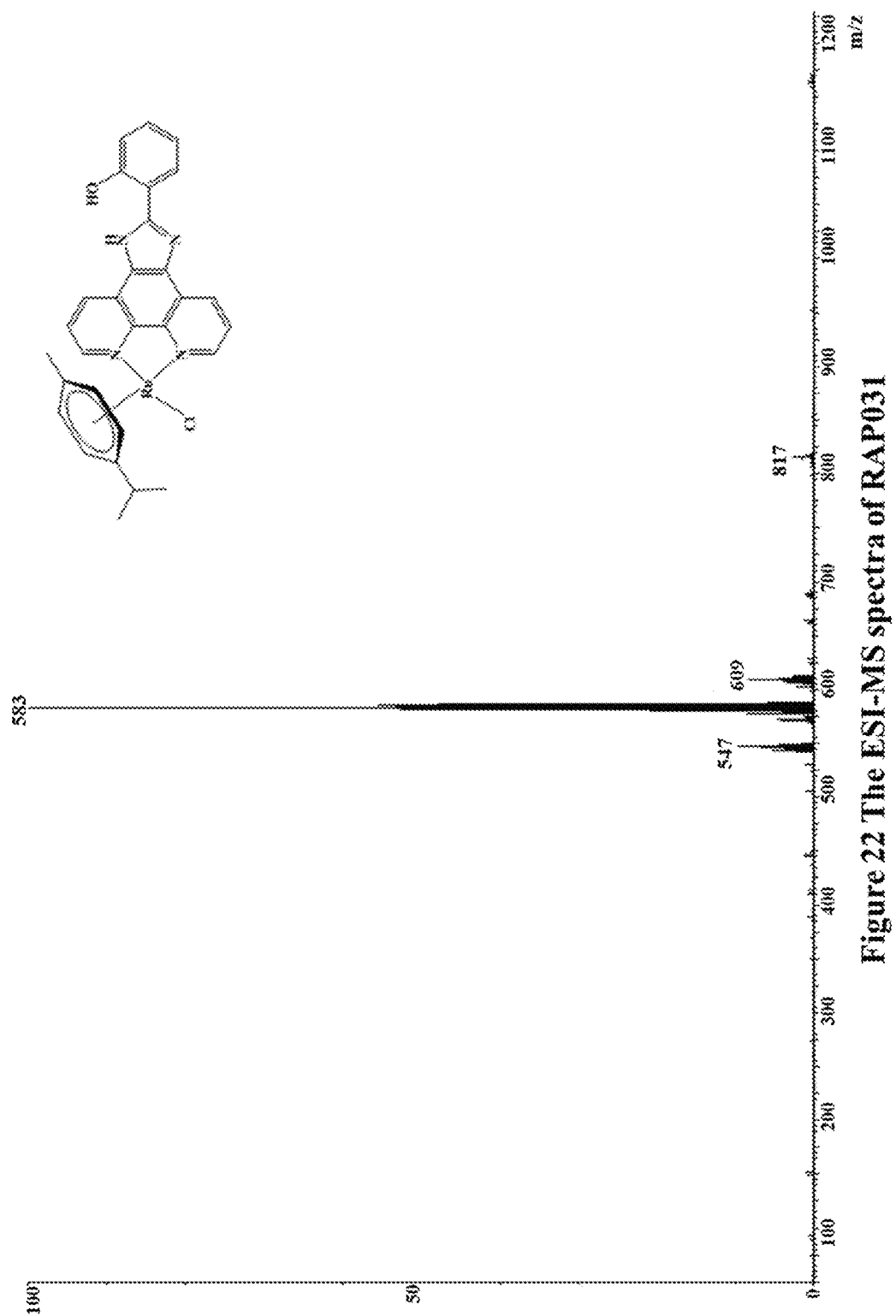
Figure 22 The ESI-MS spectra of RAP031

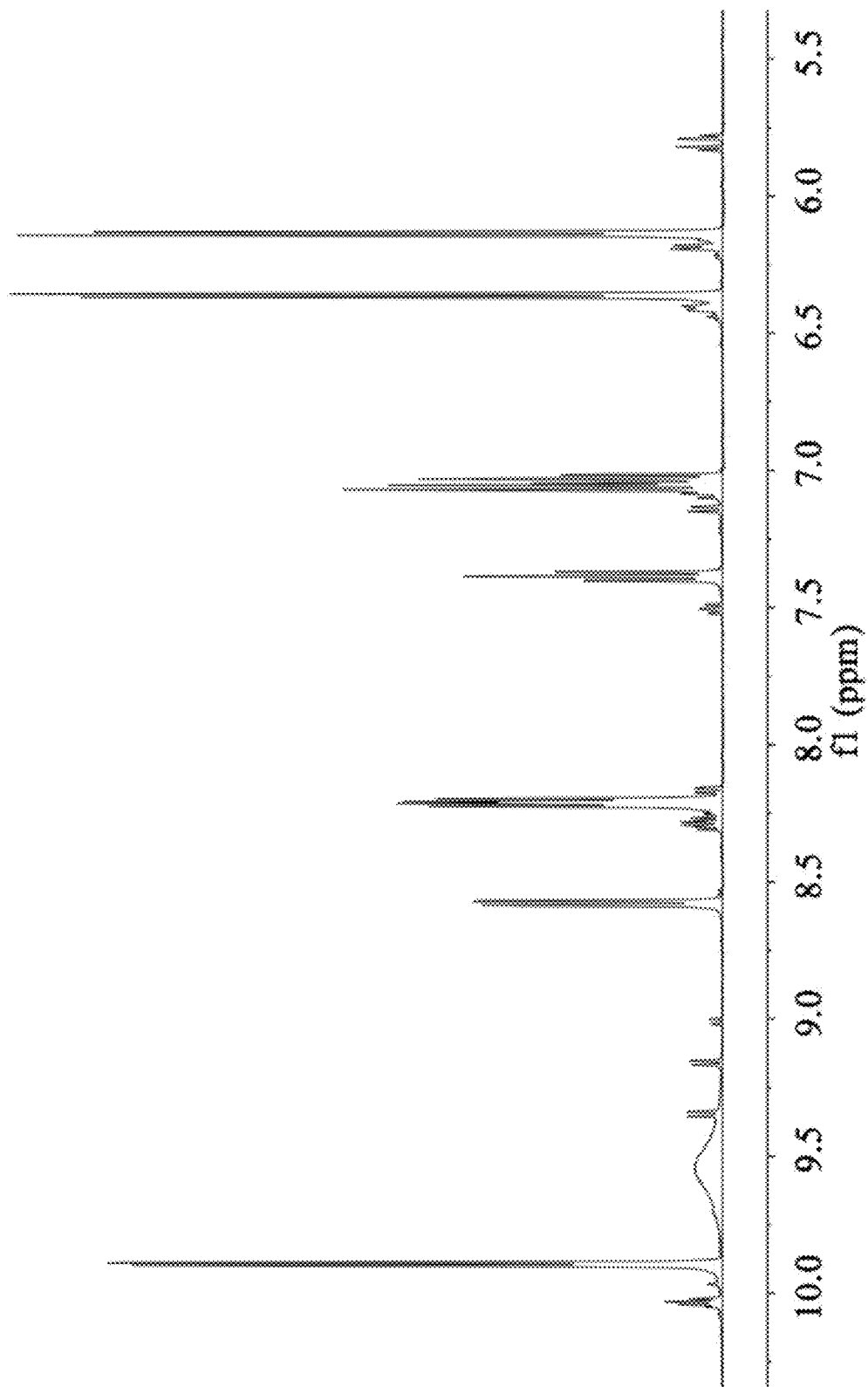
Figure 23 The $^1$H NMR spectra of RAP031

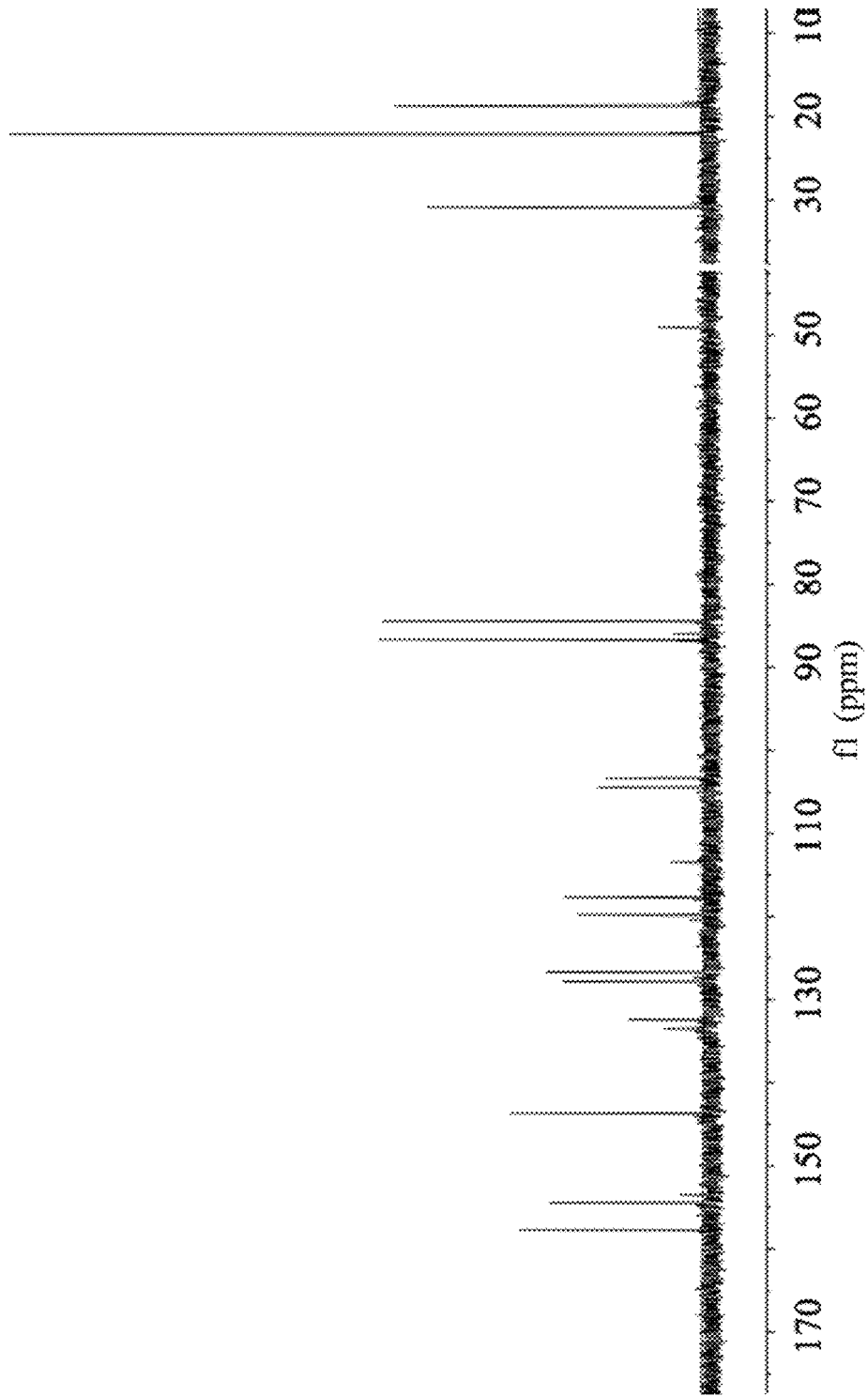

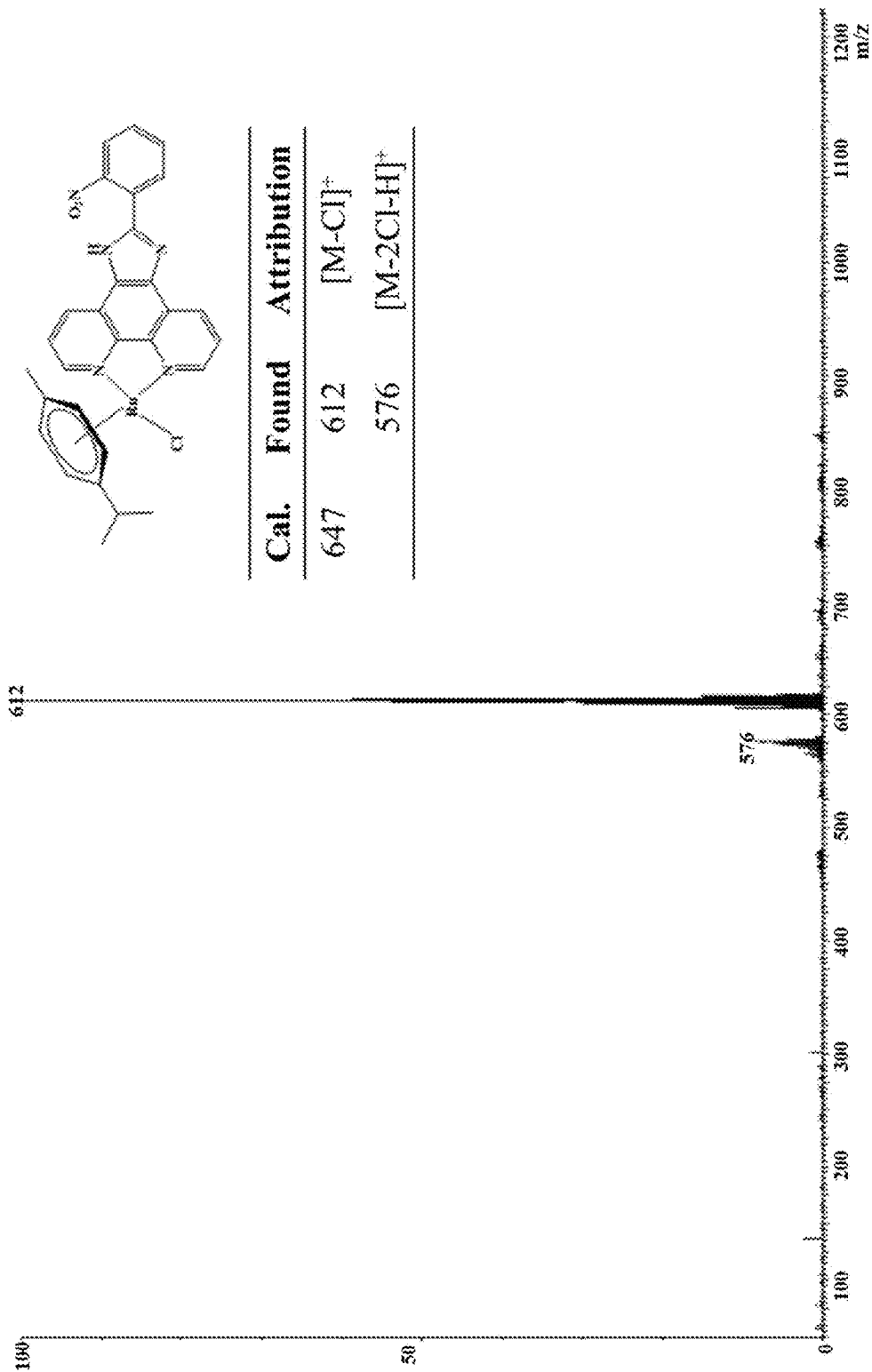
Figure 25 The ESI-MS spectra of RAP141

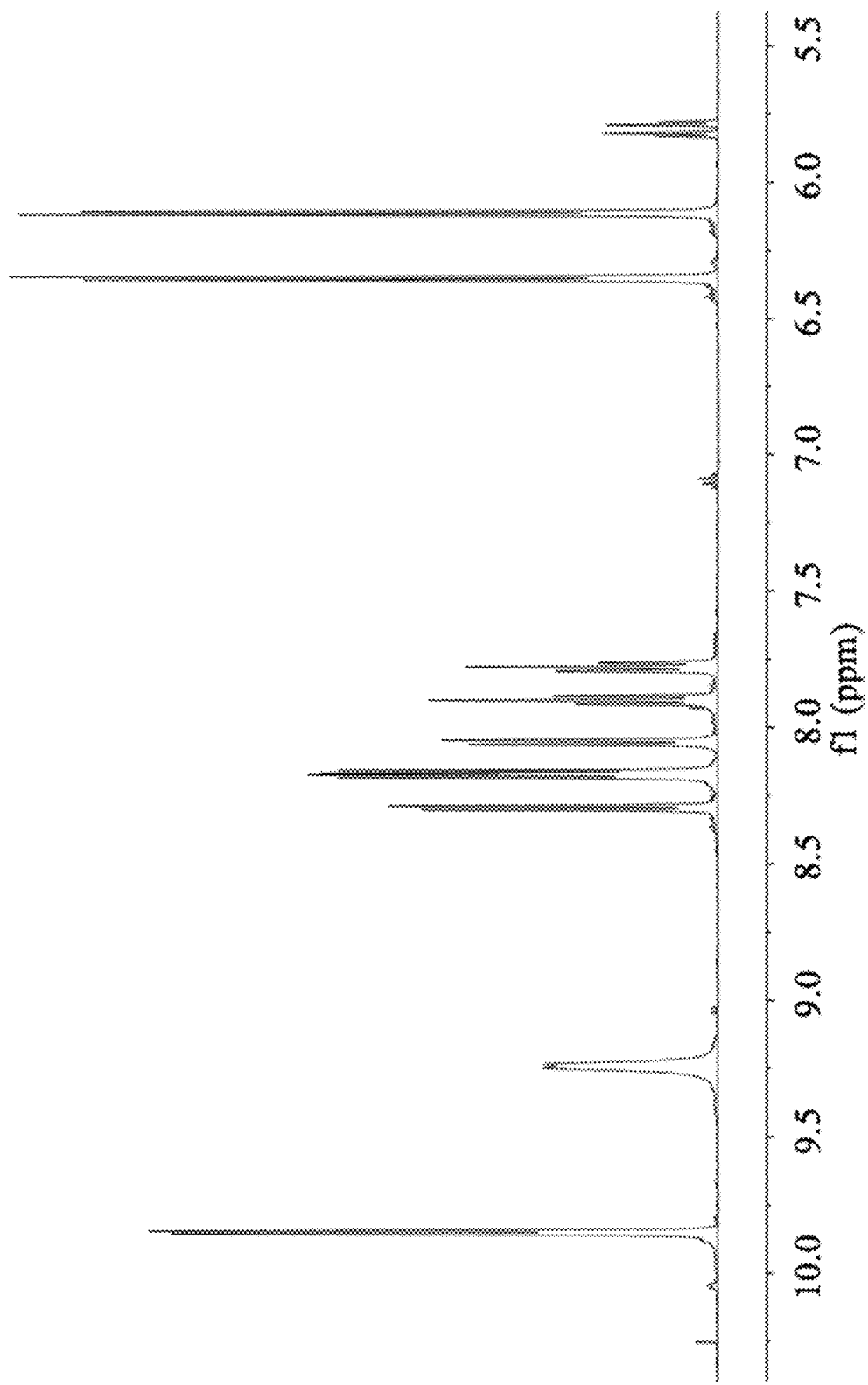
Figure 26 The ¹H NMR spectra of RAP141

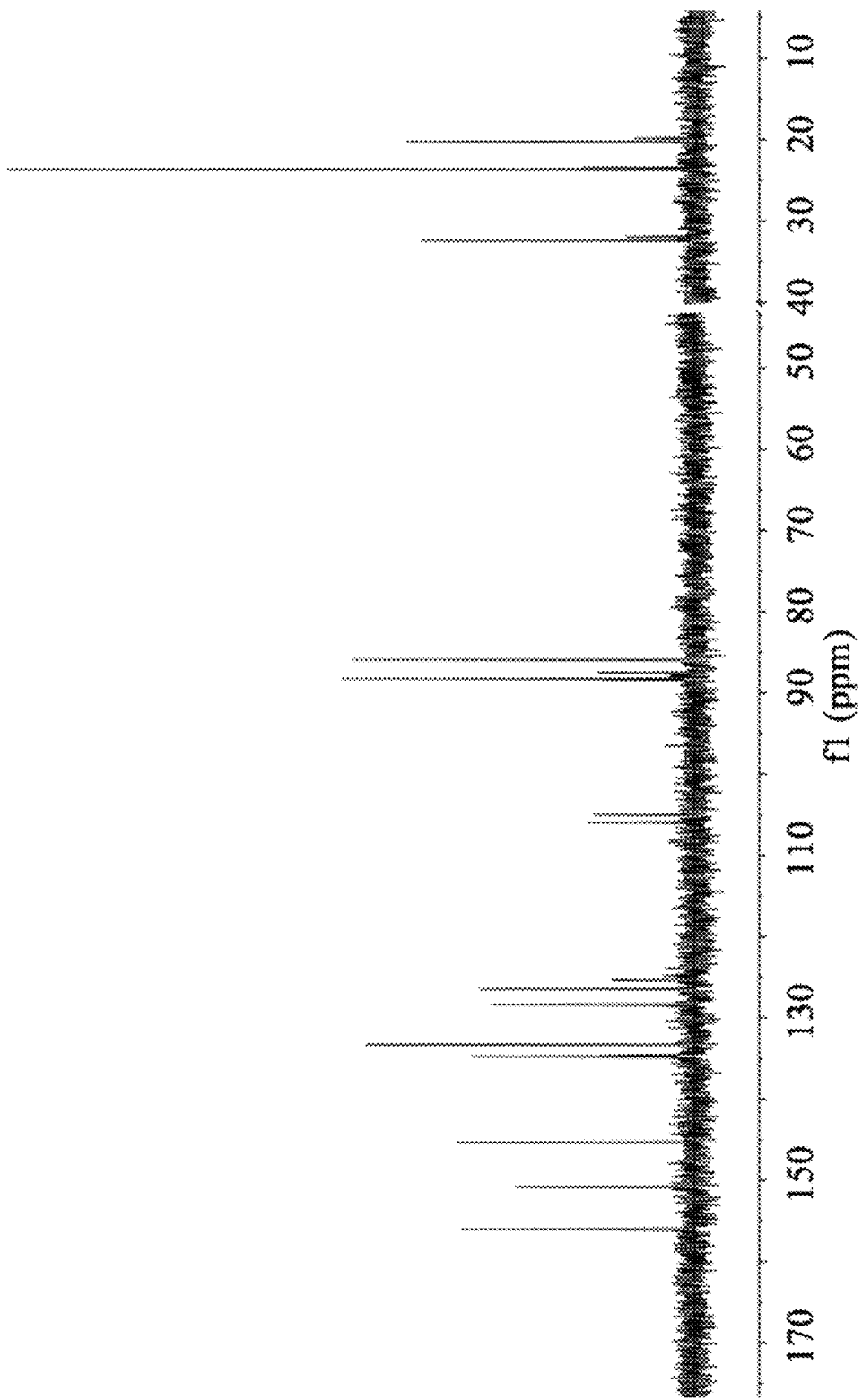

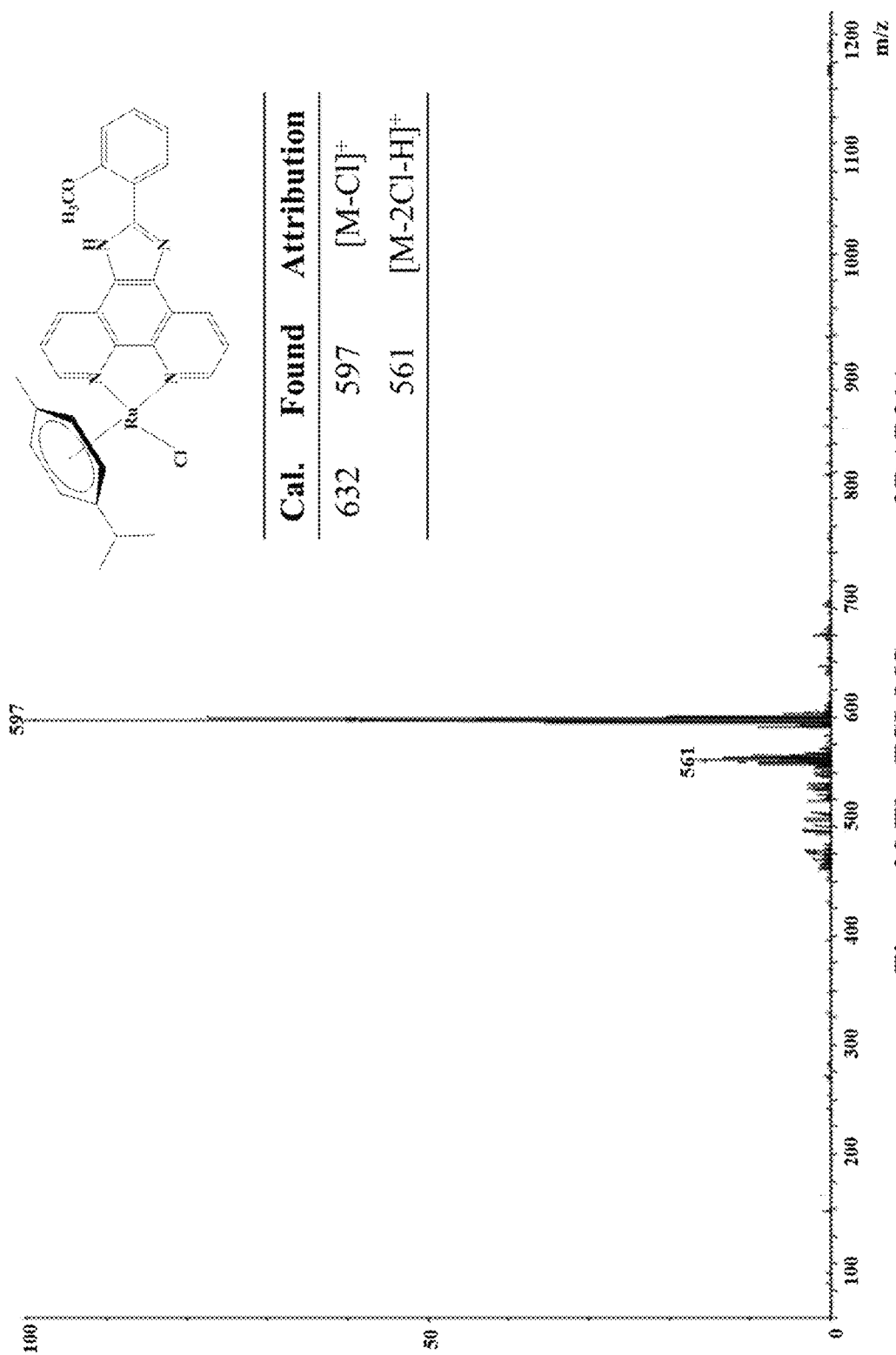
Figure 28 The ESI-MS spectra of RAP201

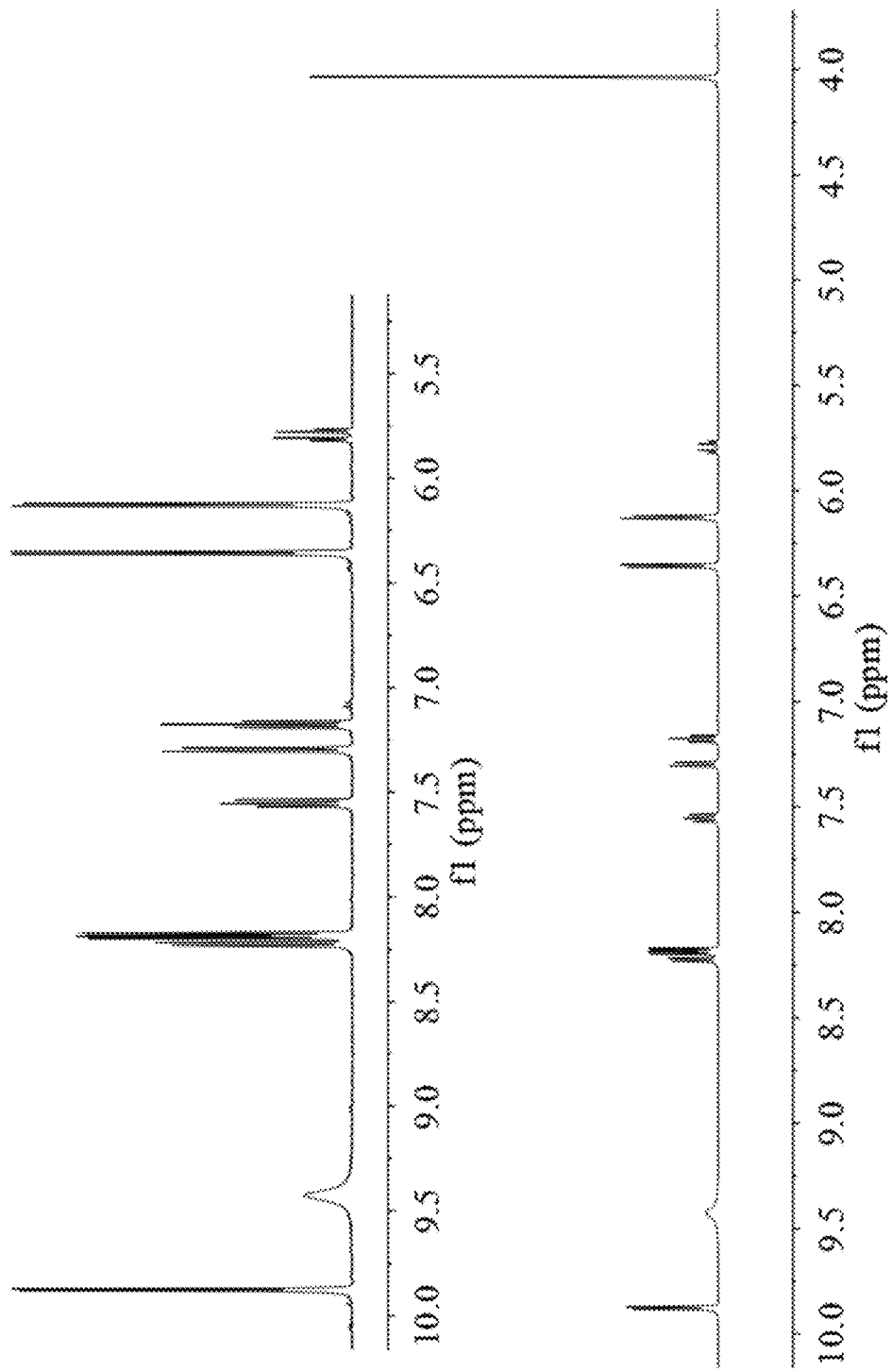
Figure 29 The $^1$H NMR spectra of RAP201

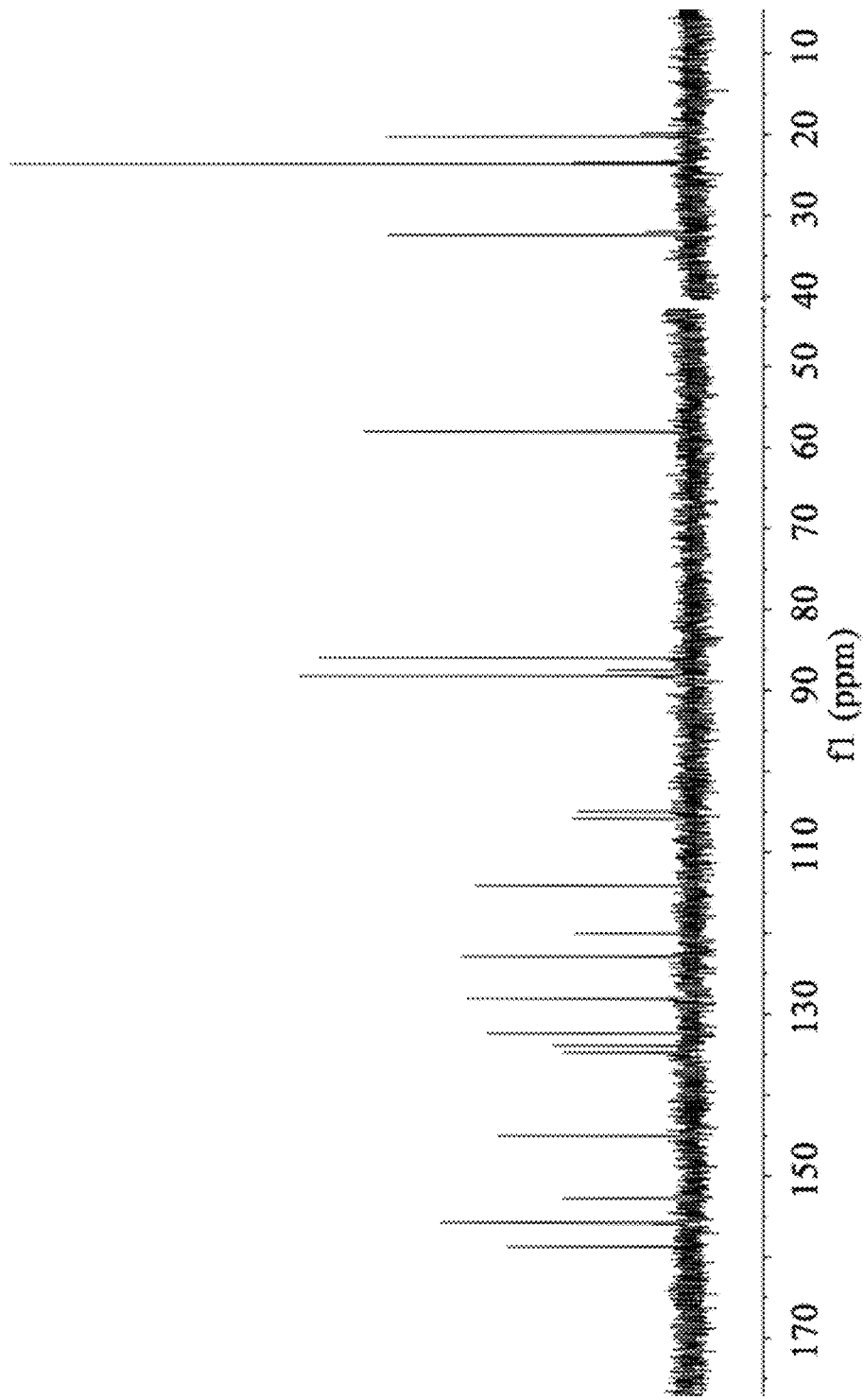
Figure 30 The $^{13}$C NMR spectra of RAP201

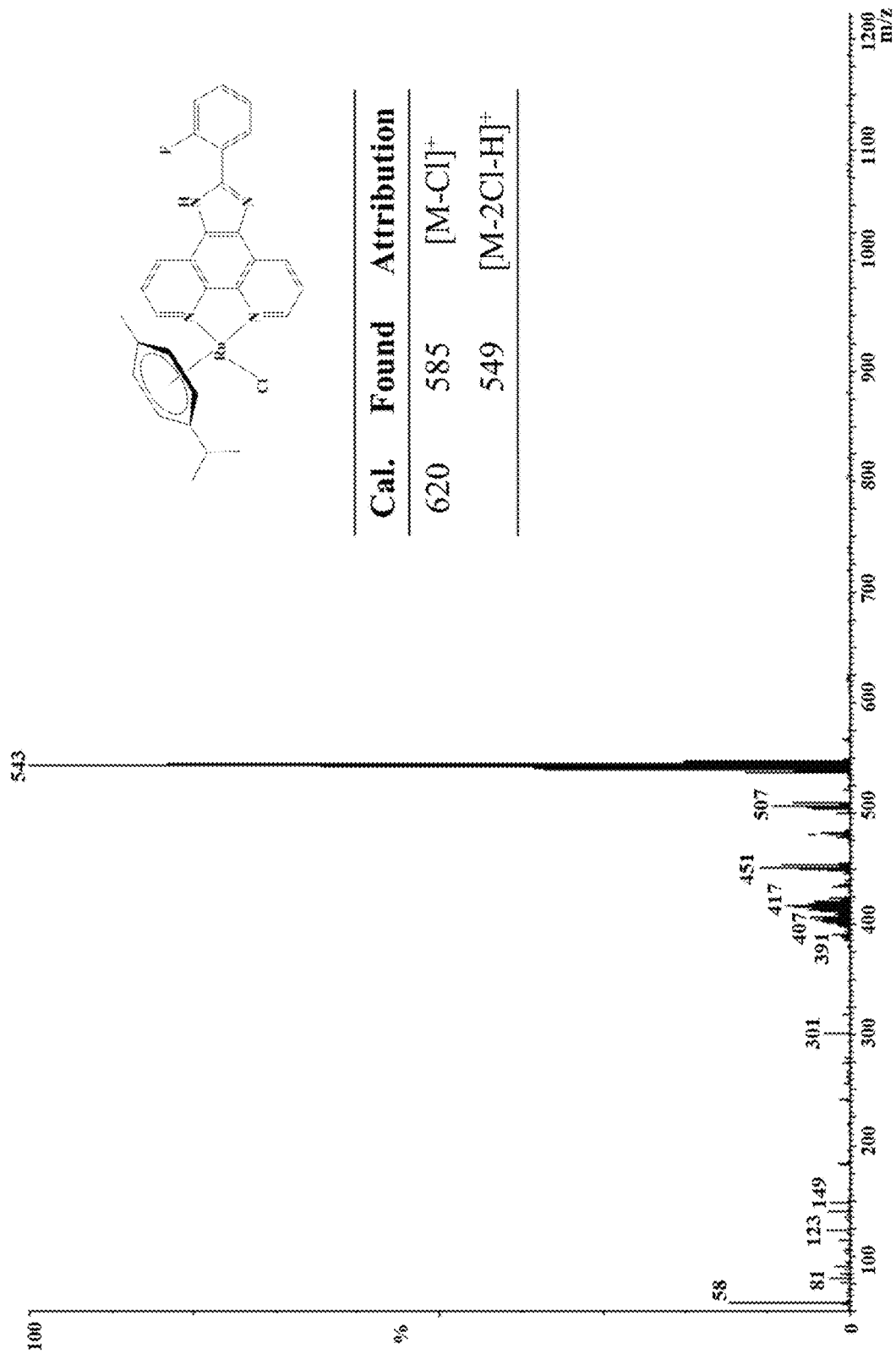
Figure 31 The ESI-MS spectra of RAP041

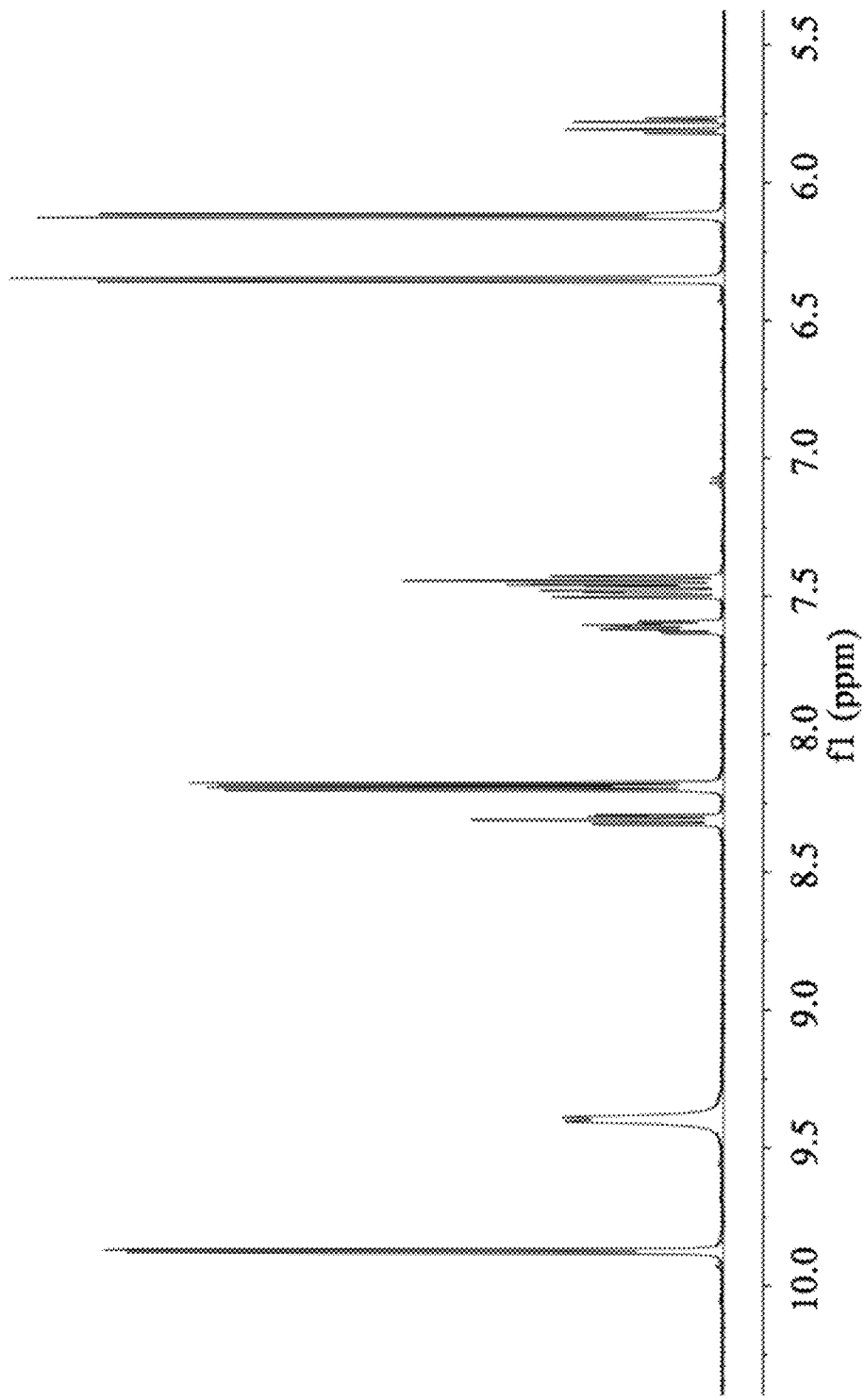
Figure 32 The $^1$H NMR spectra of RAP041

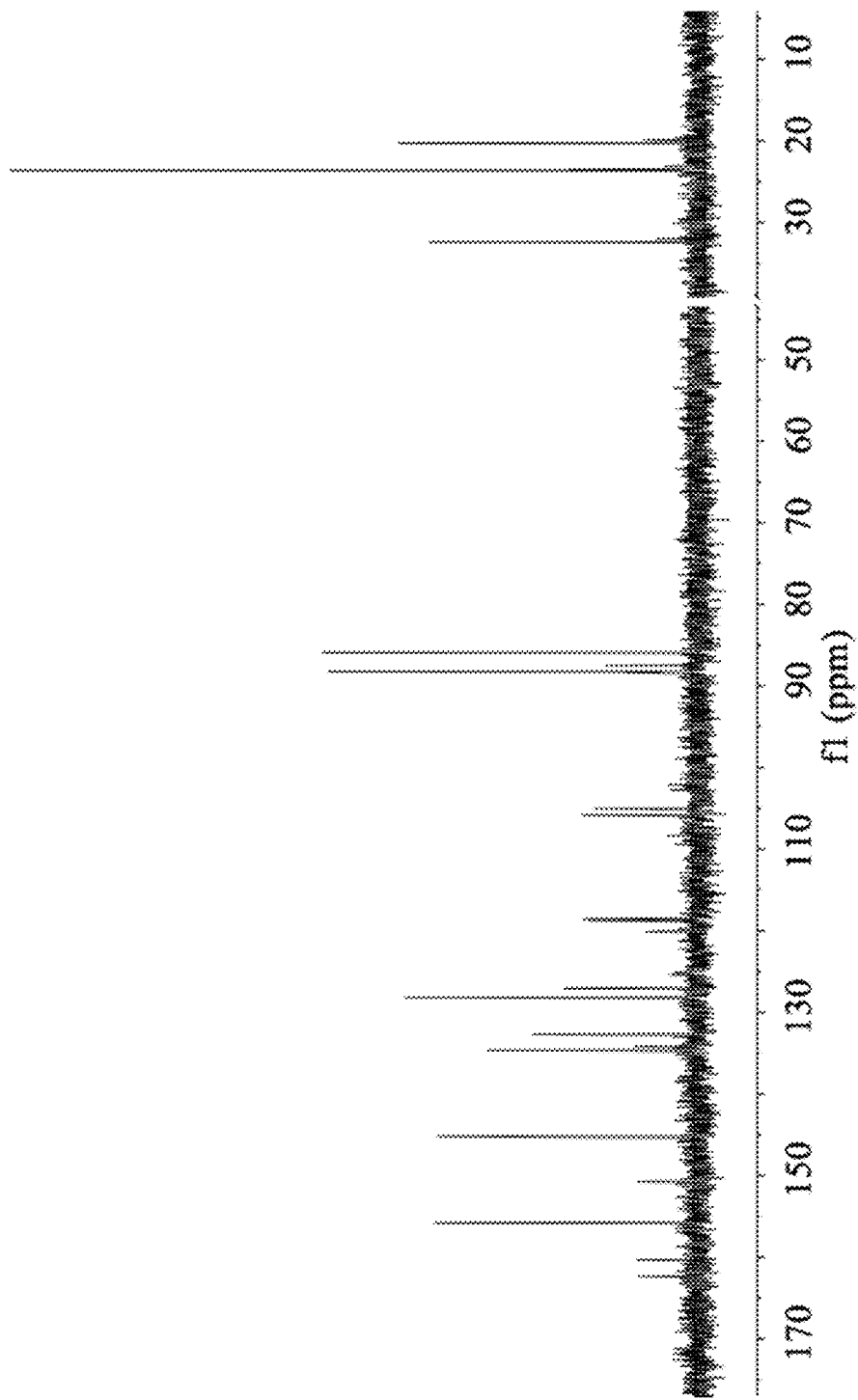
Figure 33 The $^{13}$C NMR spectra of RAP041

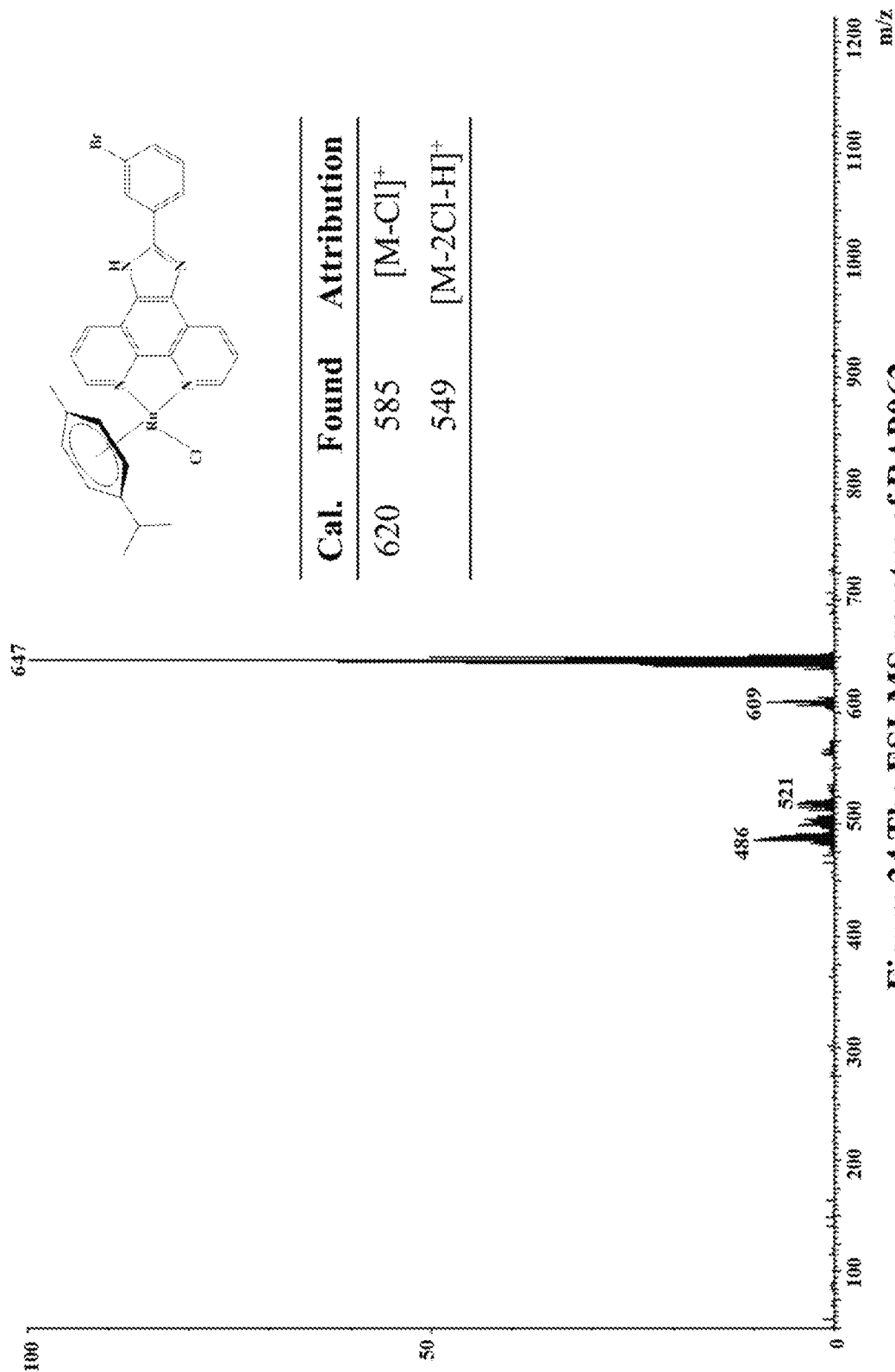
Figure 34 The ESI-MS spectra of RAP062

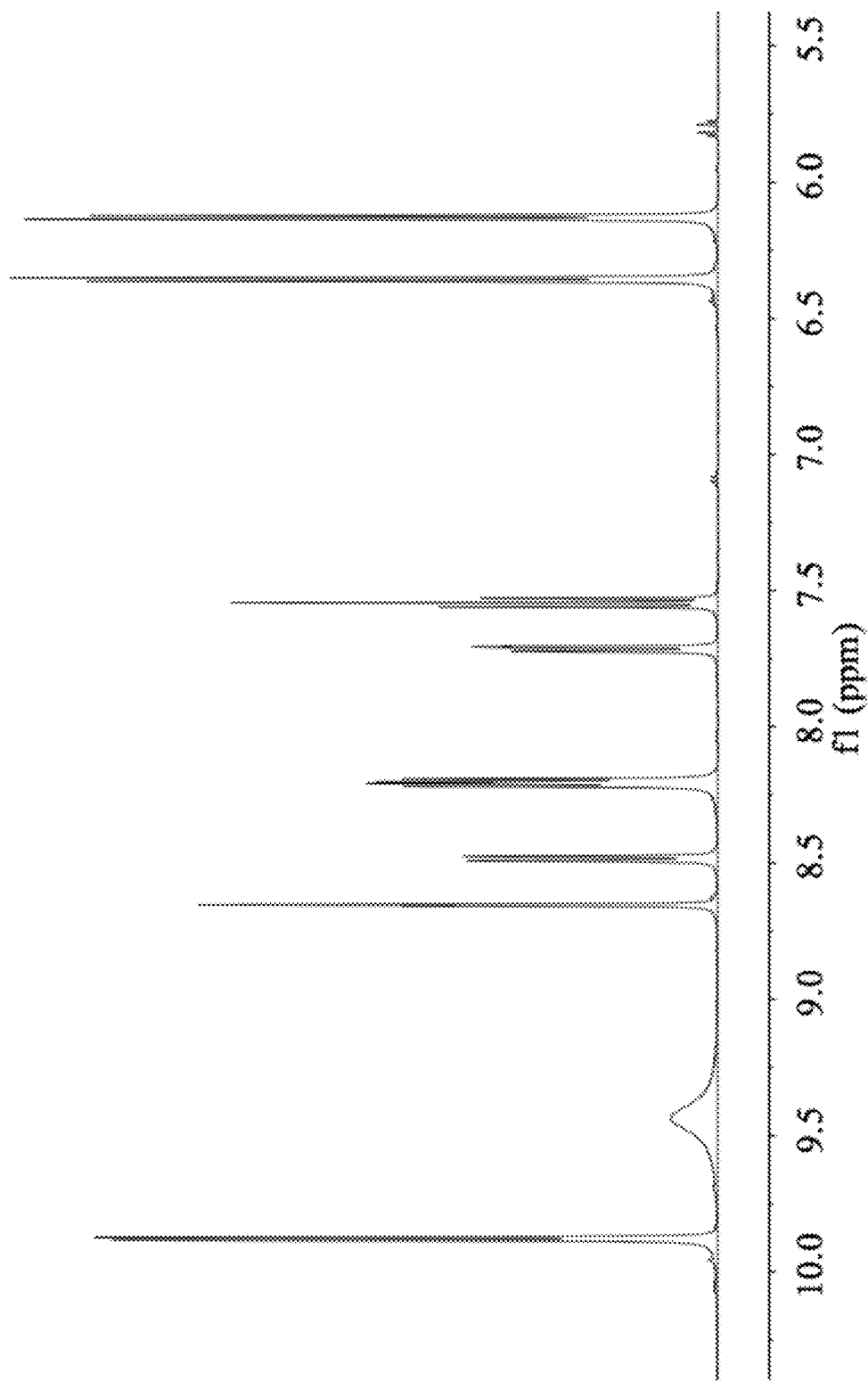
Figure 35 The $^1$H NMR spectra of RAP062

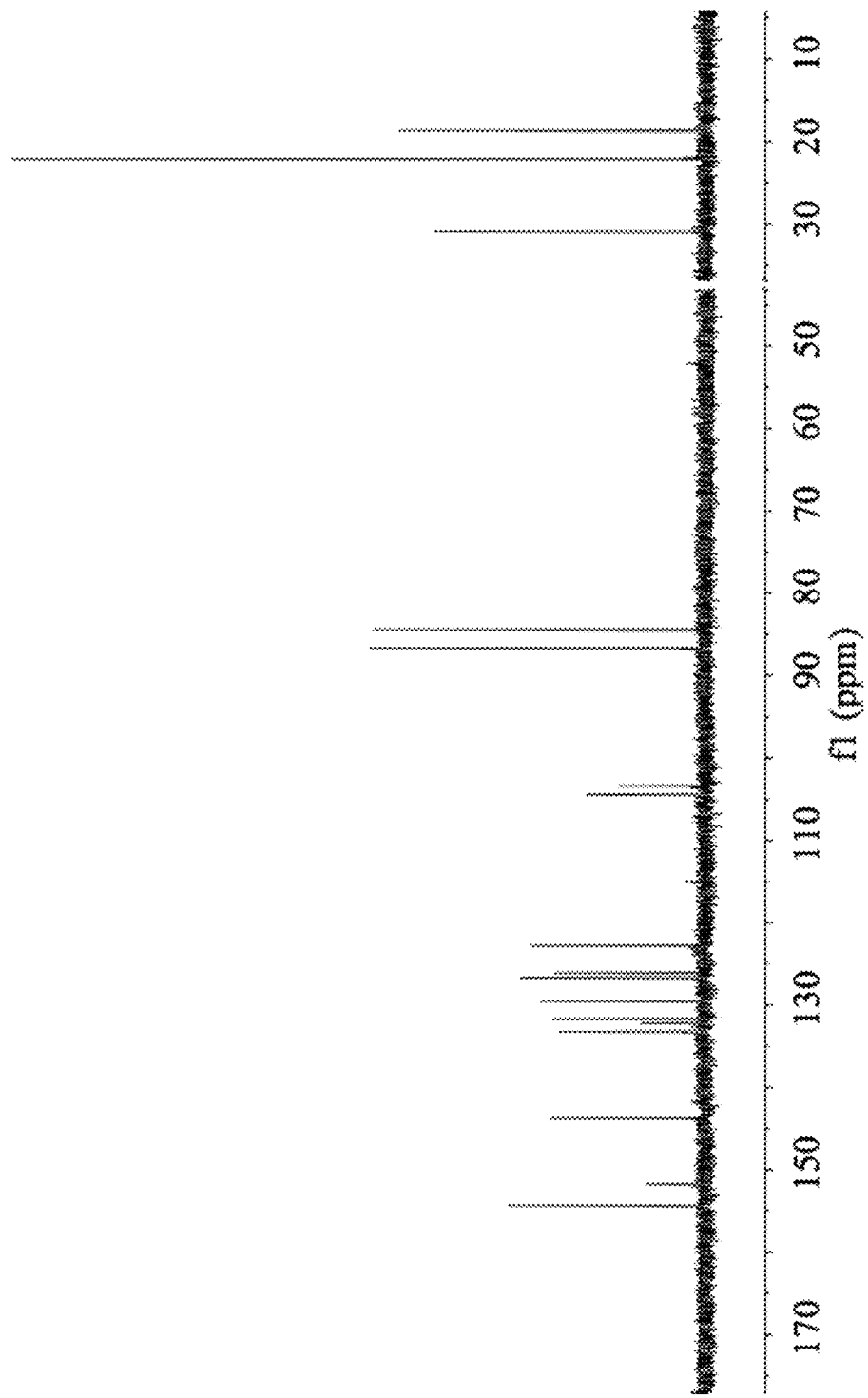
Figure 36 The $^{13}$C NMR spectra of RAP062

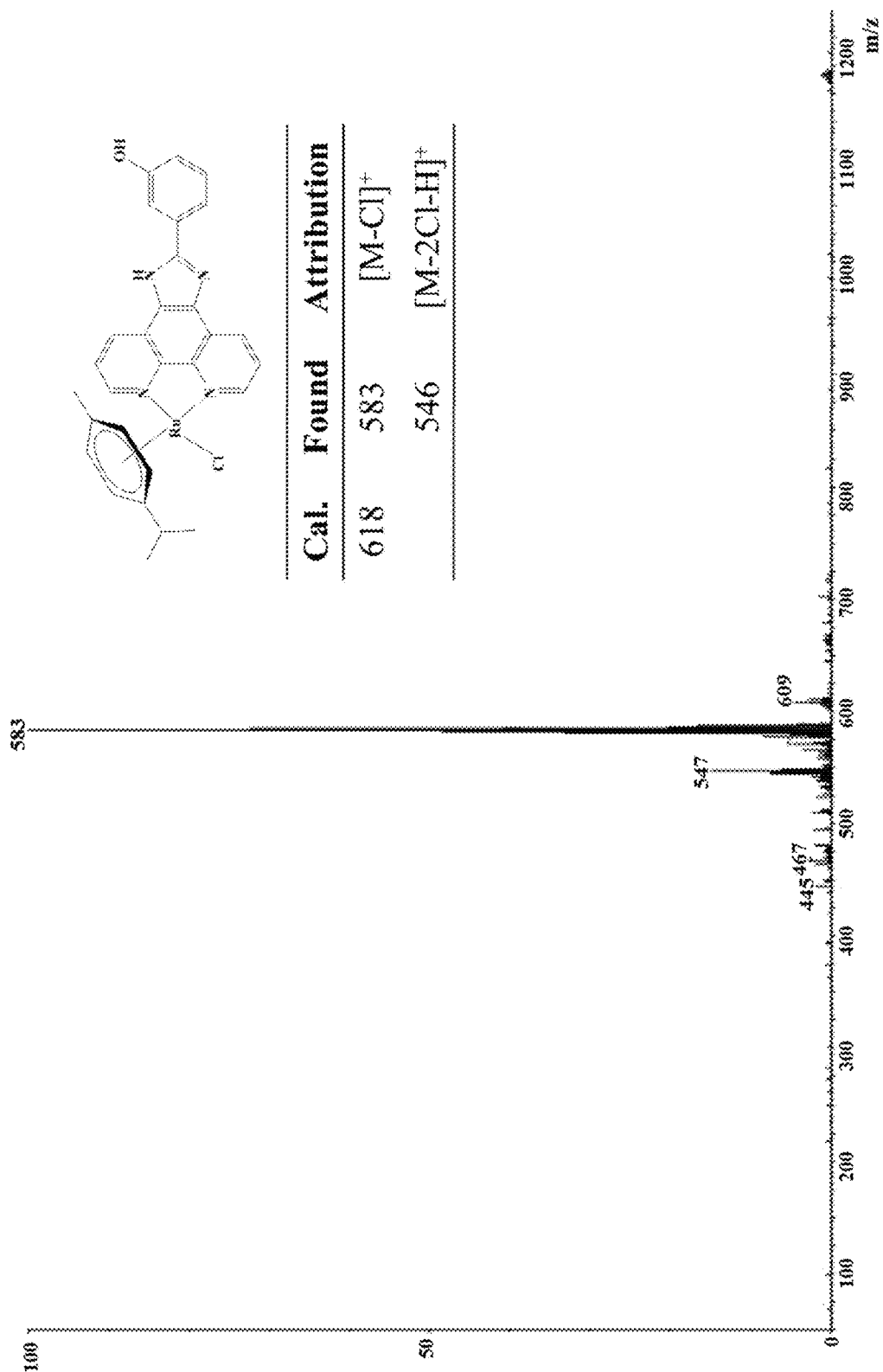
Figure 37 The ESI-MS spectra of RAP032

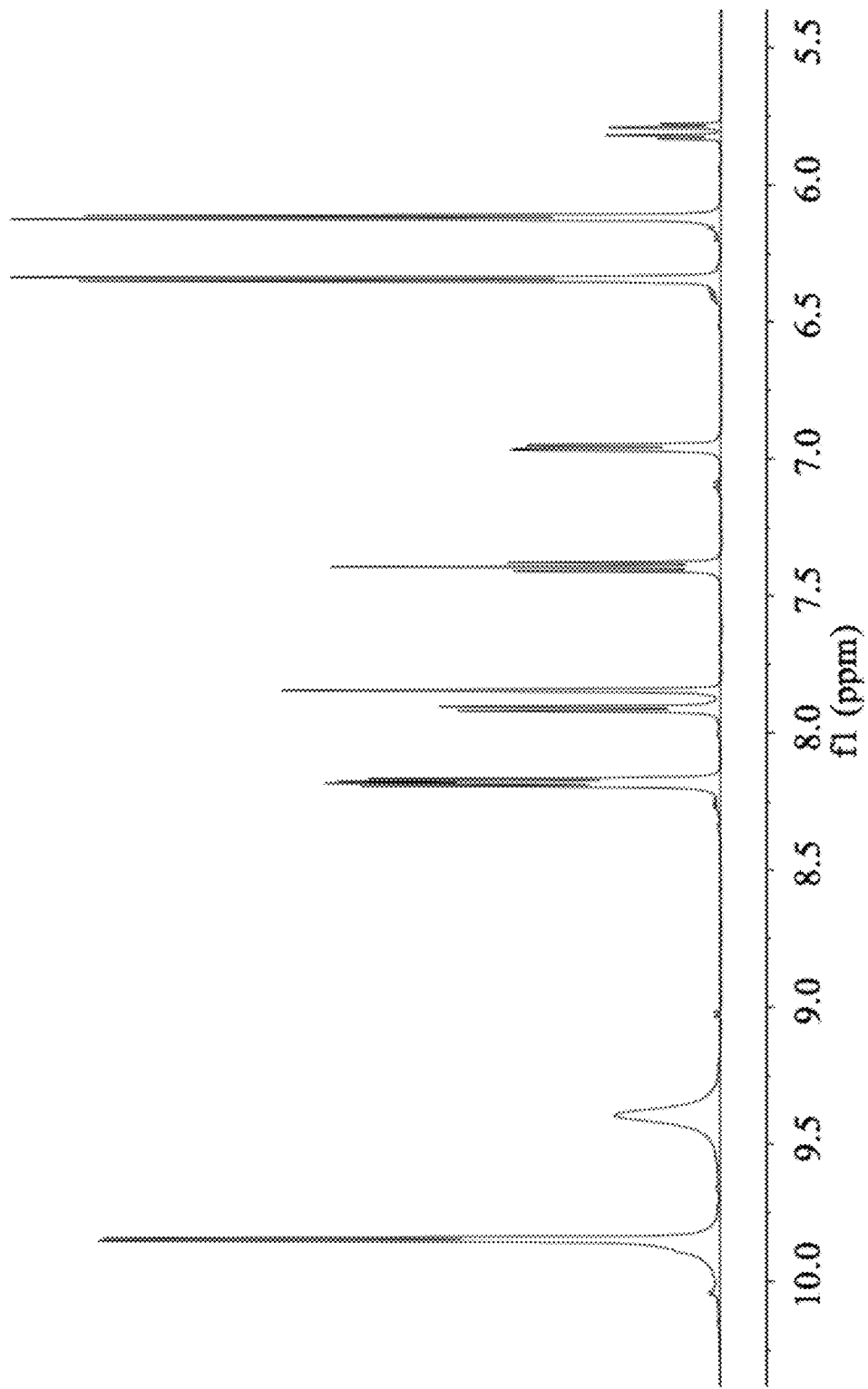
Figure 38 The $^1$H NMR spectra of RAP032

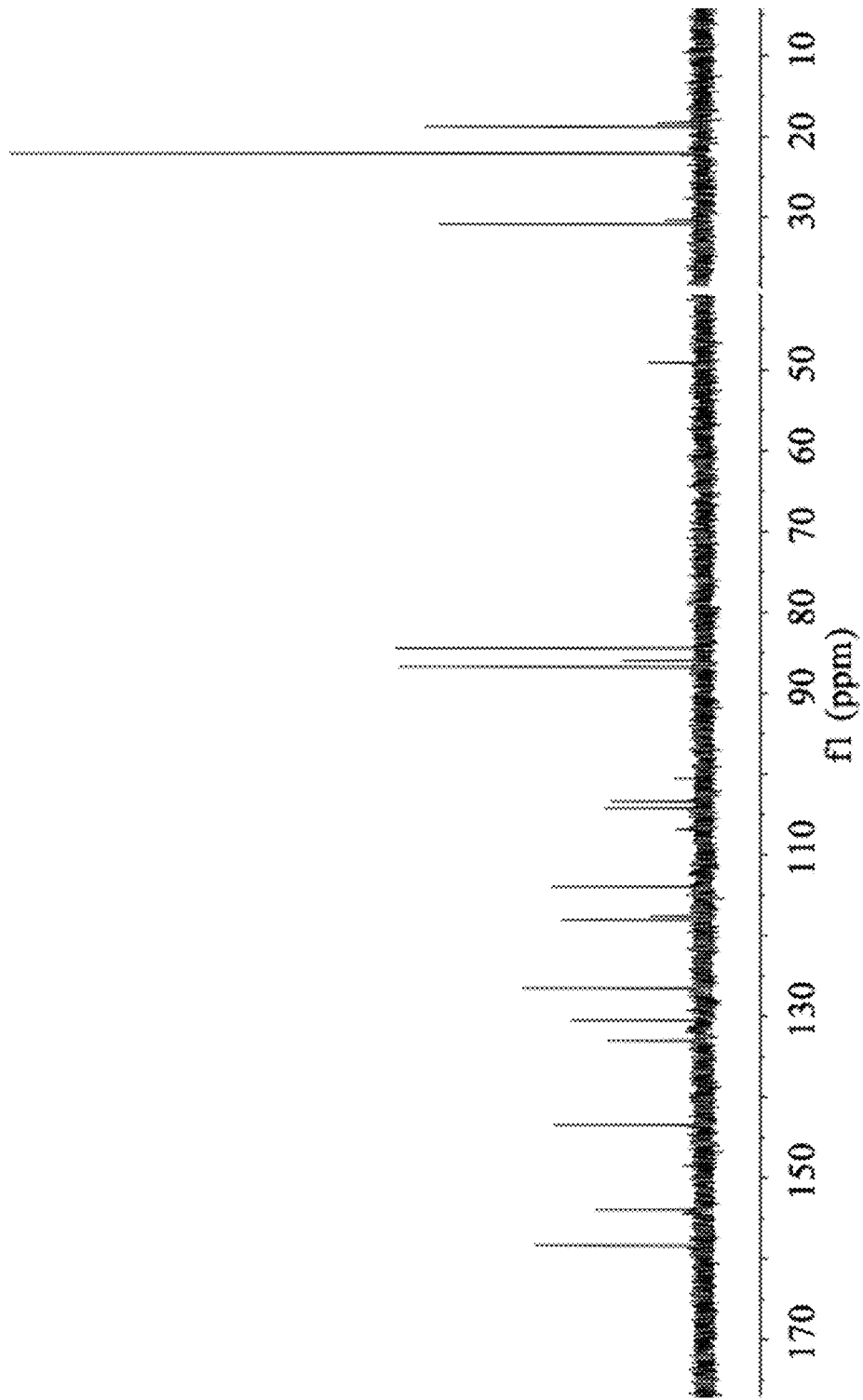
Figure 39 The $^{13}$C NMR spectra of RAP032

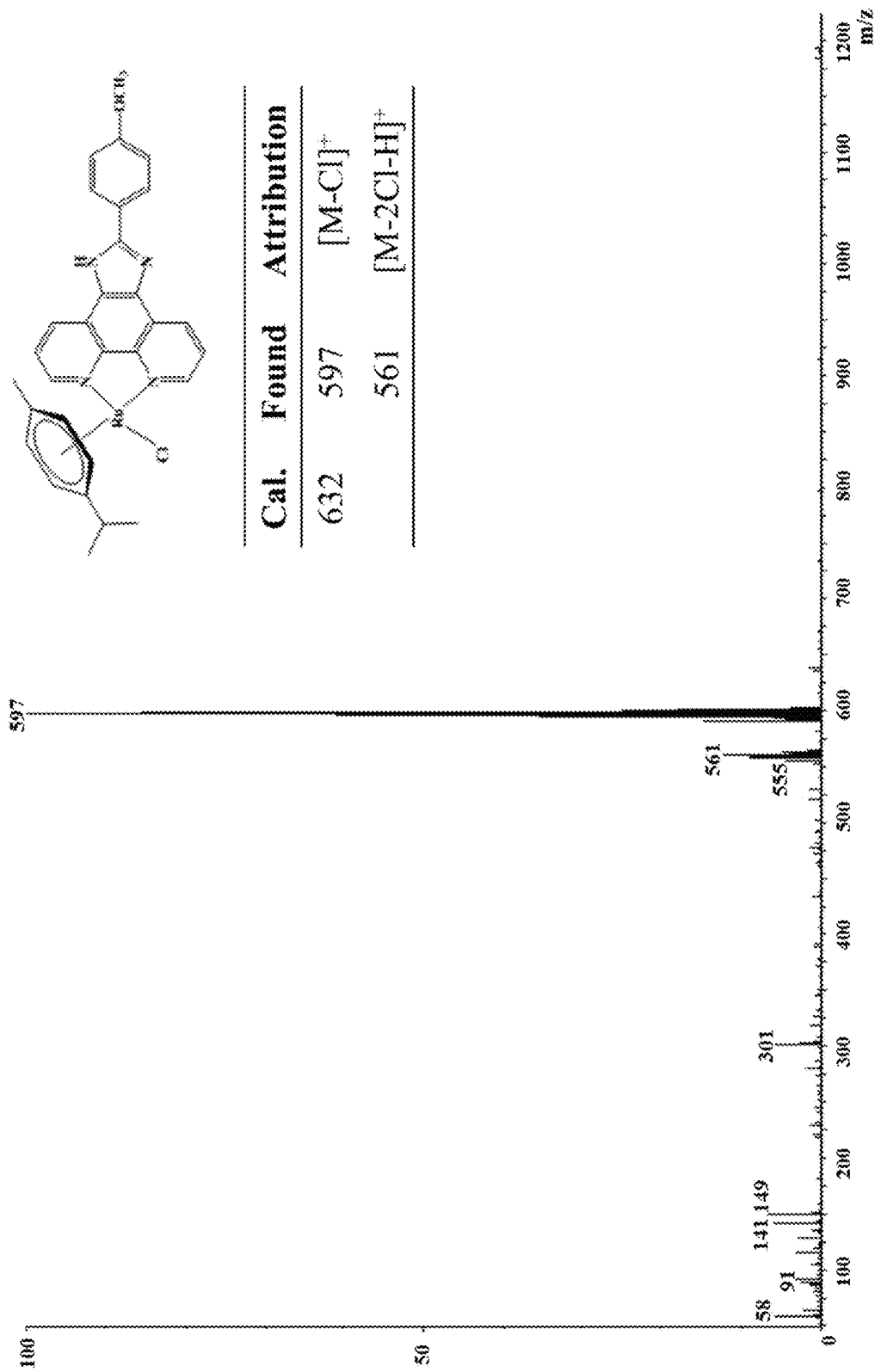
Figure 40 The ESI-MS spectra of RAP203

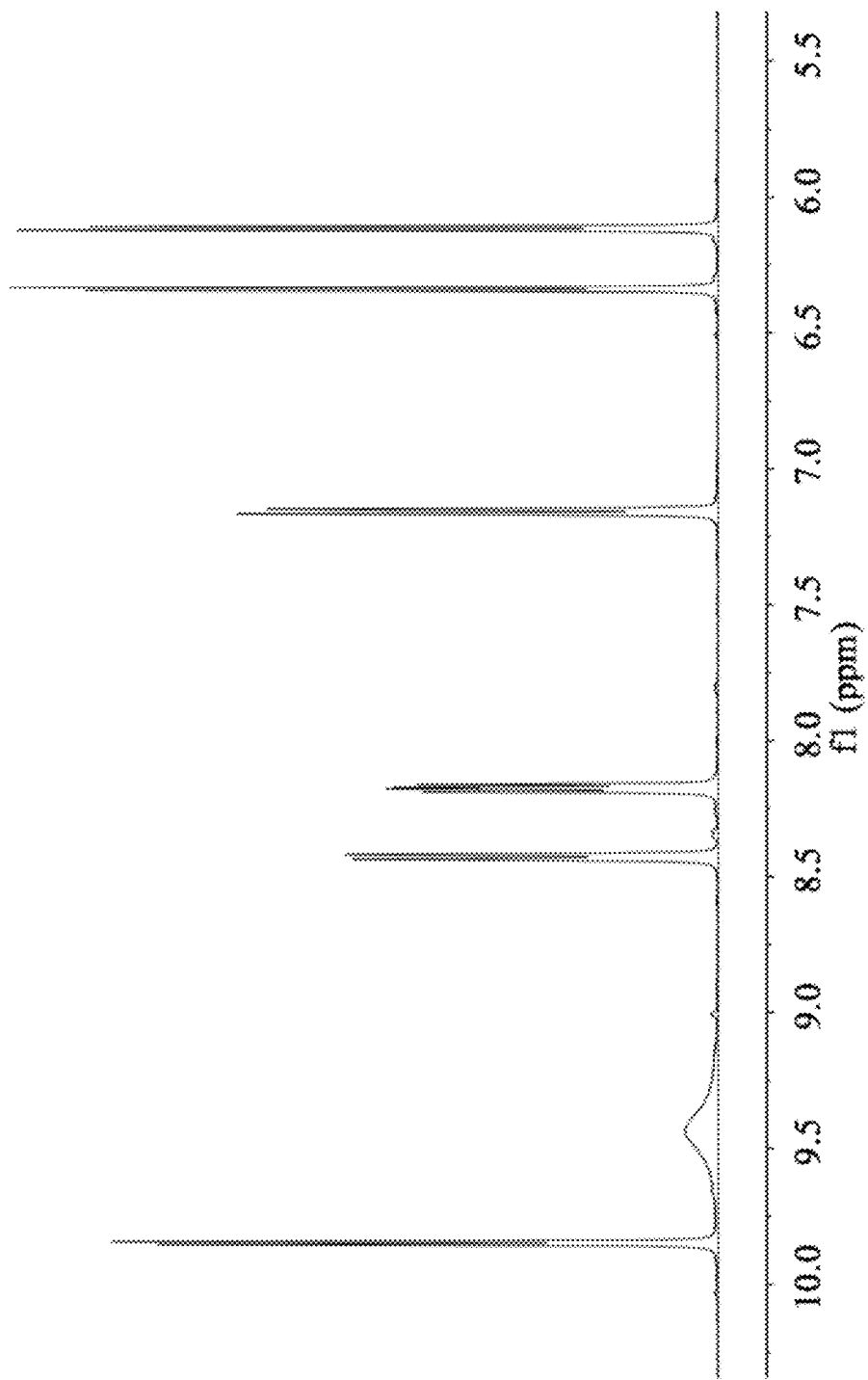

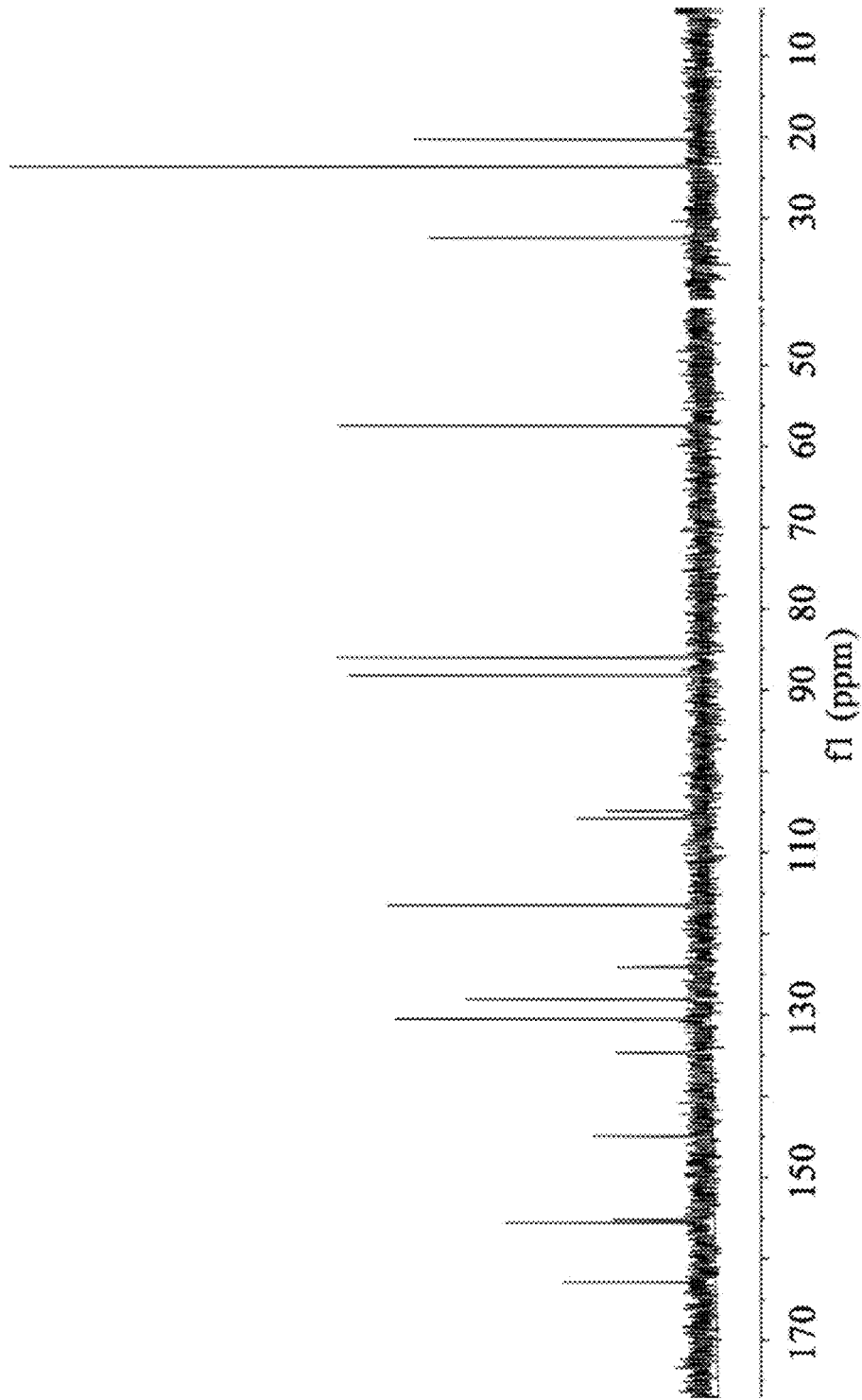
Figure 42 The $^{13}$C NMR spectra of RAP203

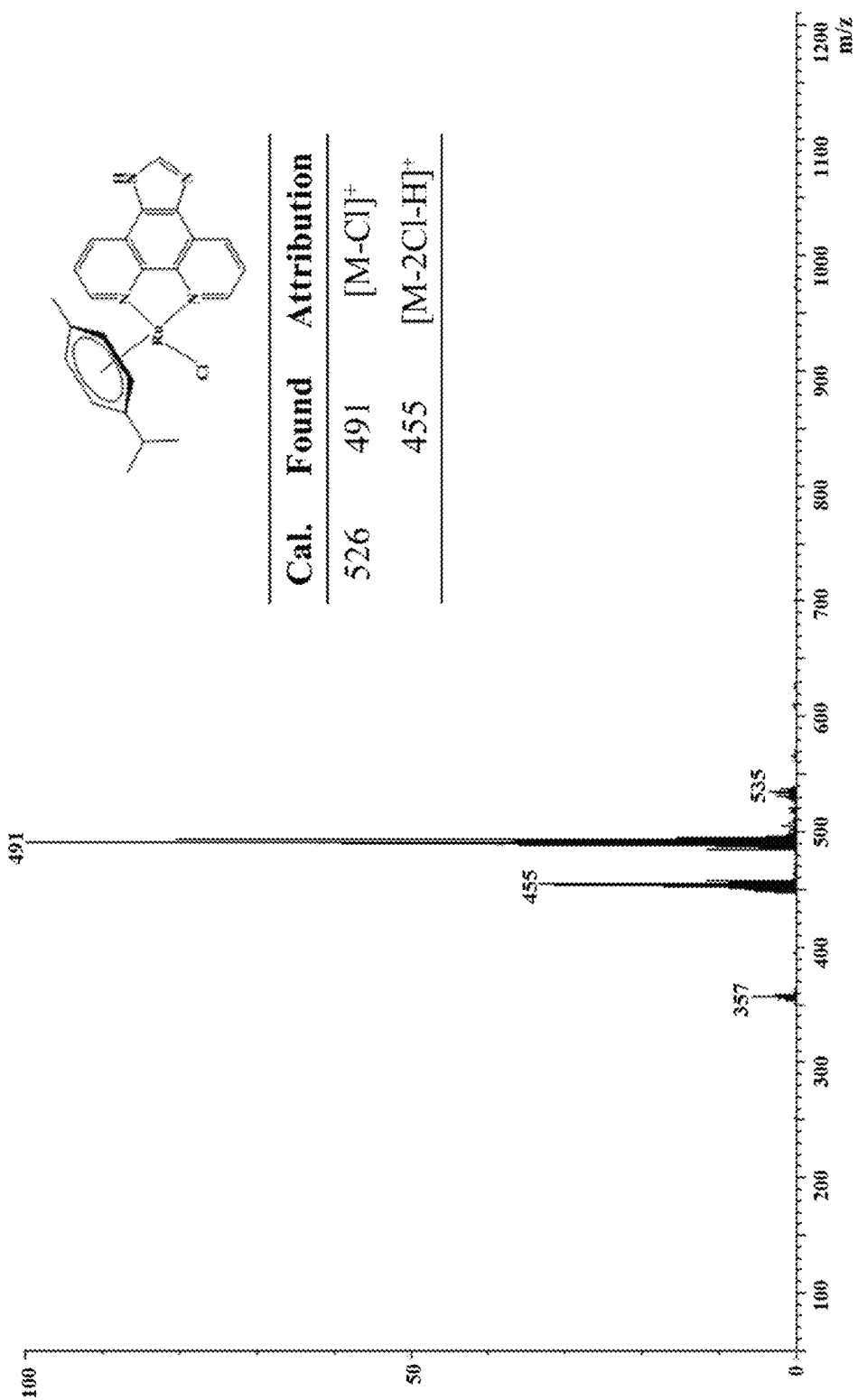
Figure 43 The ESI-MS spectra of RAP01

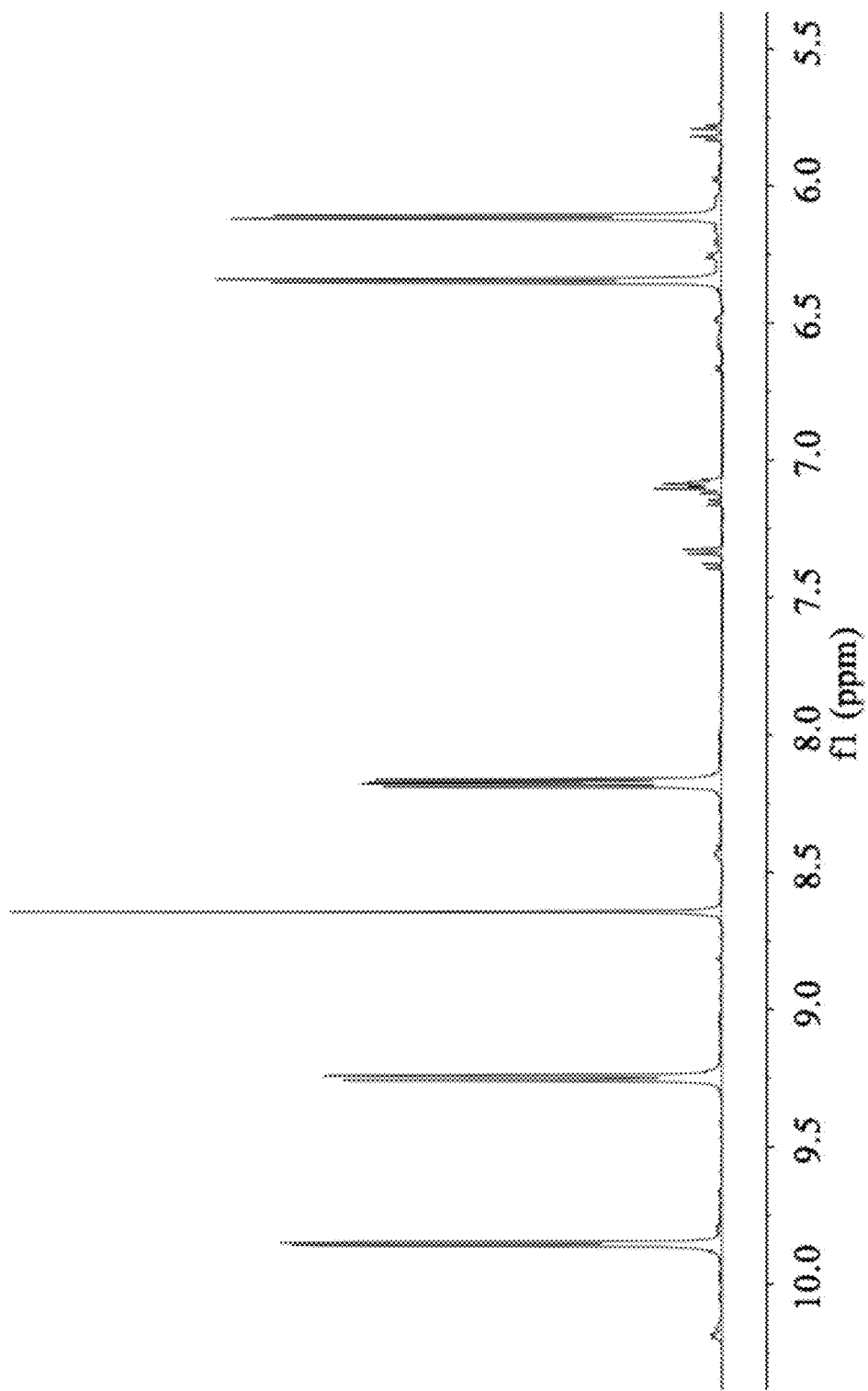
Figure 44 The $^1$H NMR spectra of RAP01

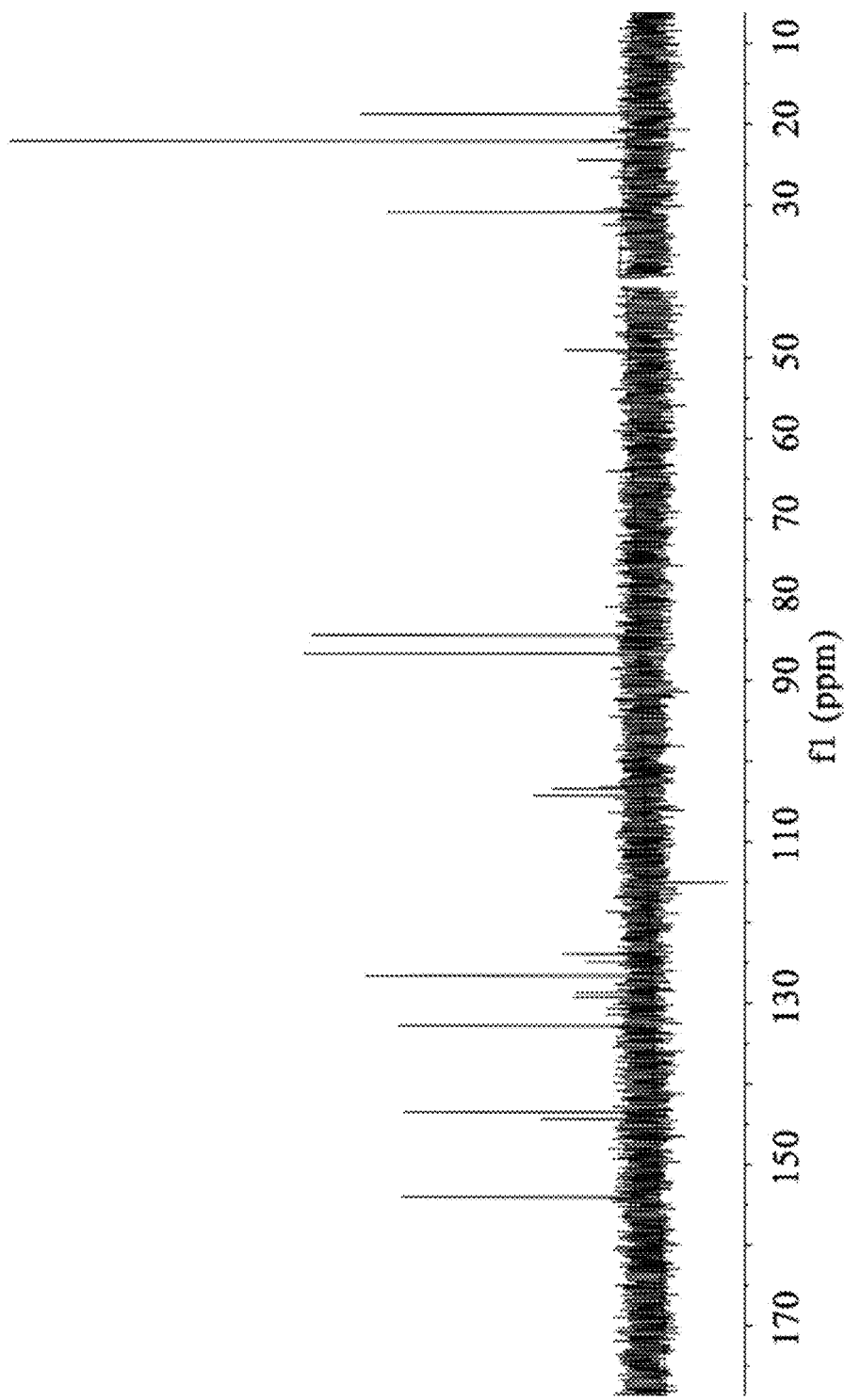
Figure 45 The $^{13}C$ NMR spectra of RAP01

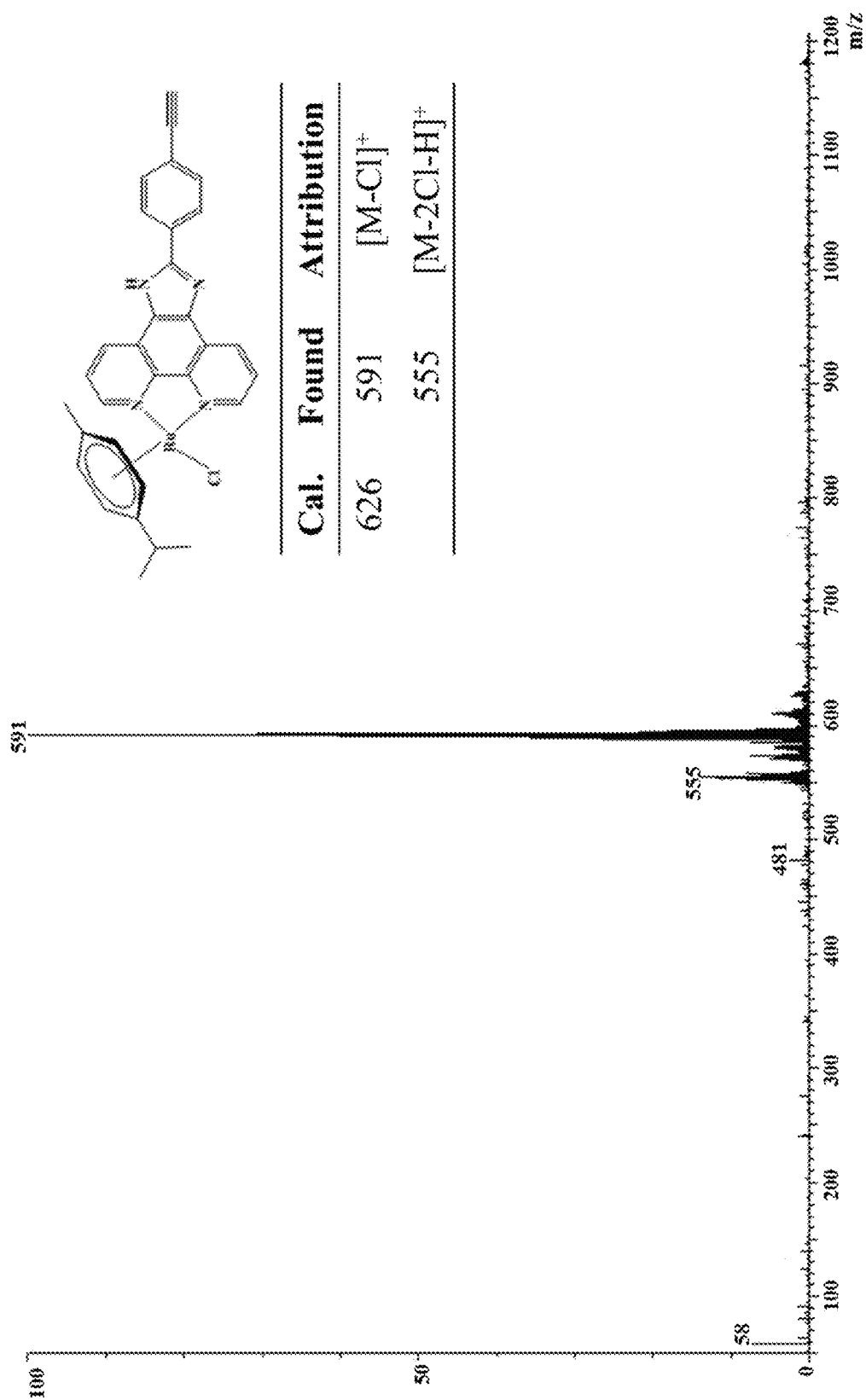
Figure 46 The ESI-MS spectra of RAP13

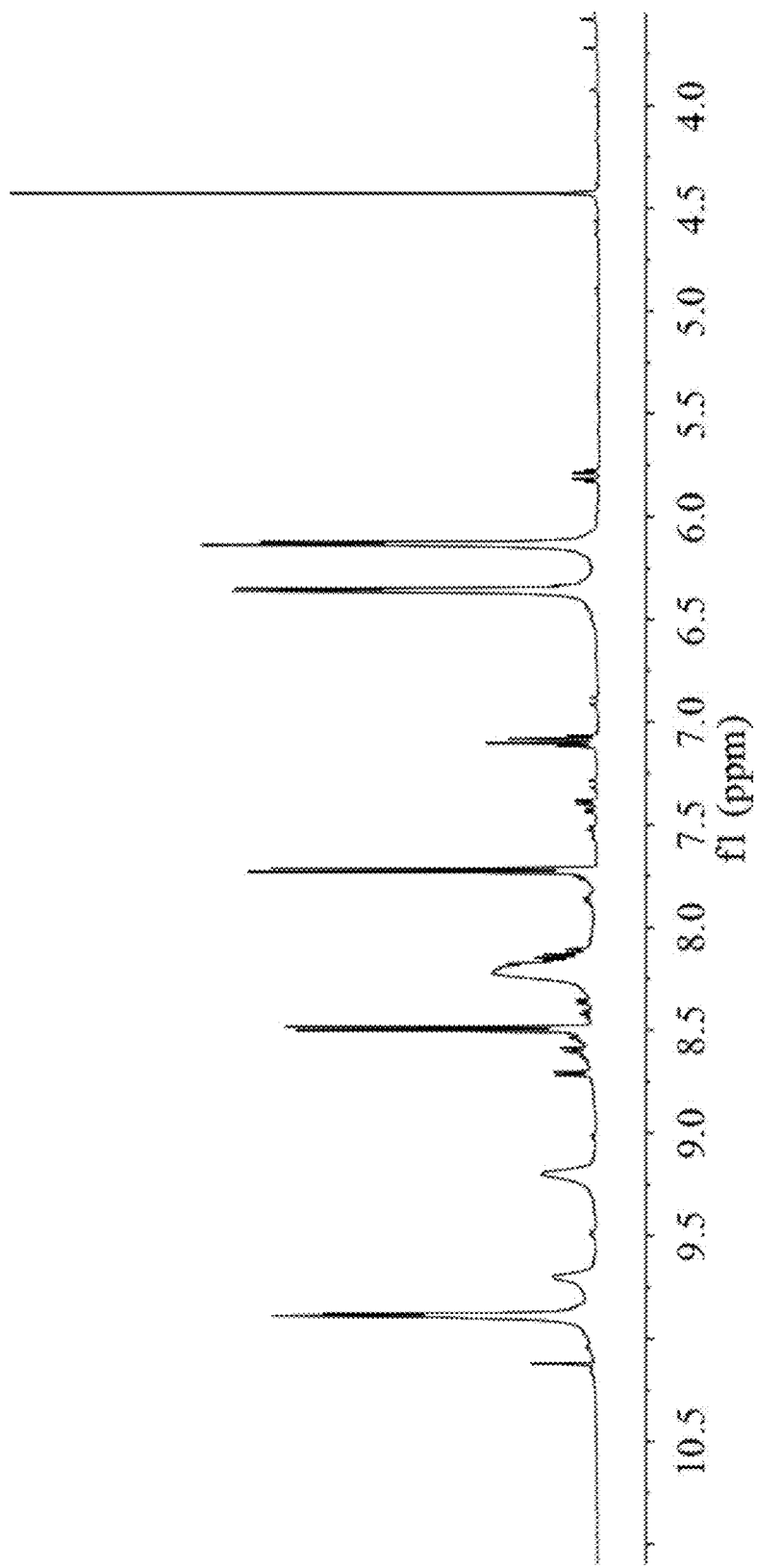
Figure 47 The $^1$H NMR spectra of RAP13

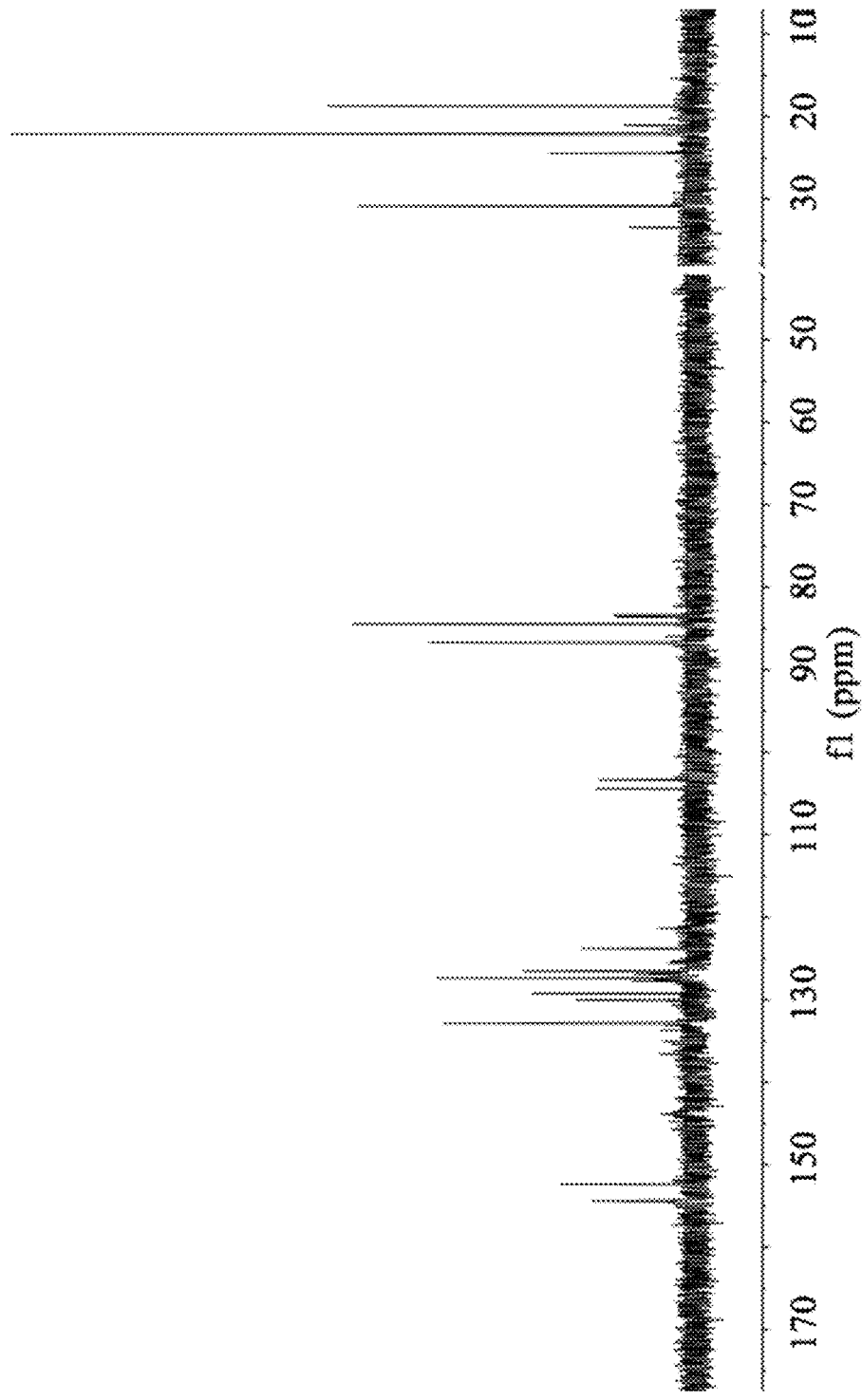
Figure 48 The 13C NMR spectra of RAP13

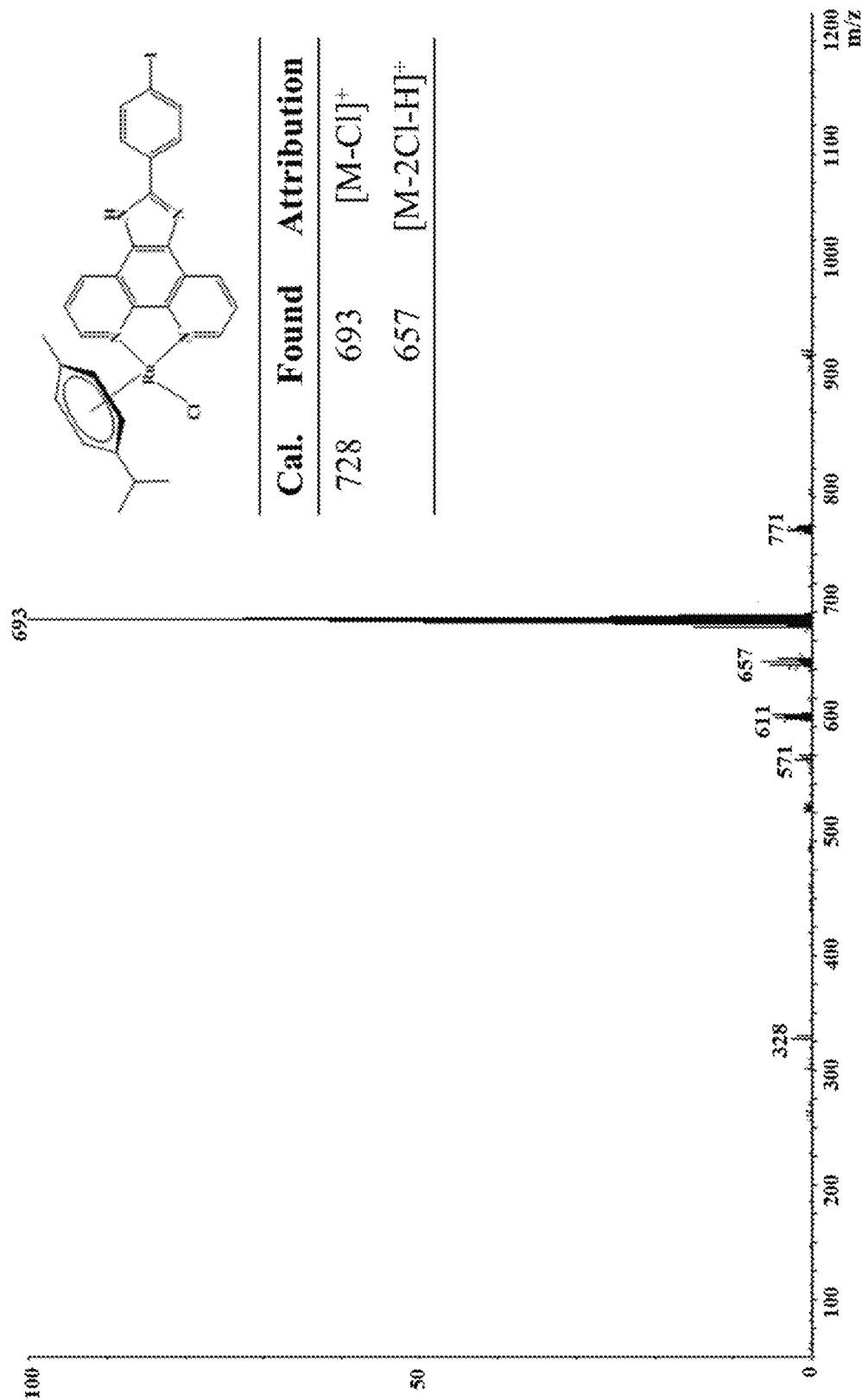
Figure 49 The ESI-MS spectra of RAP073

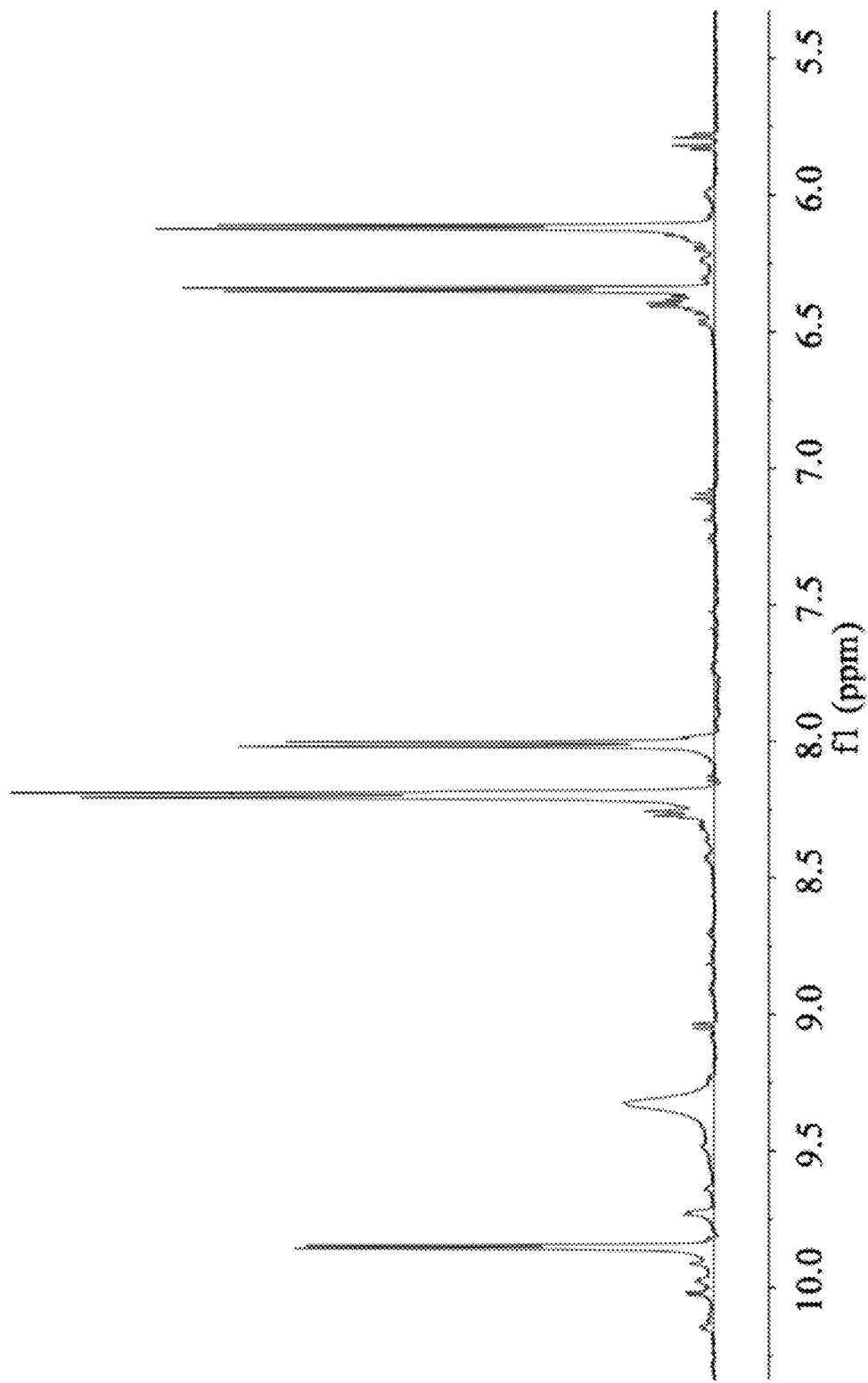
Figure 50 The $^1$H NMR spectra of RAP073

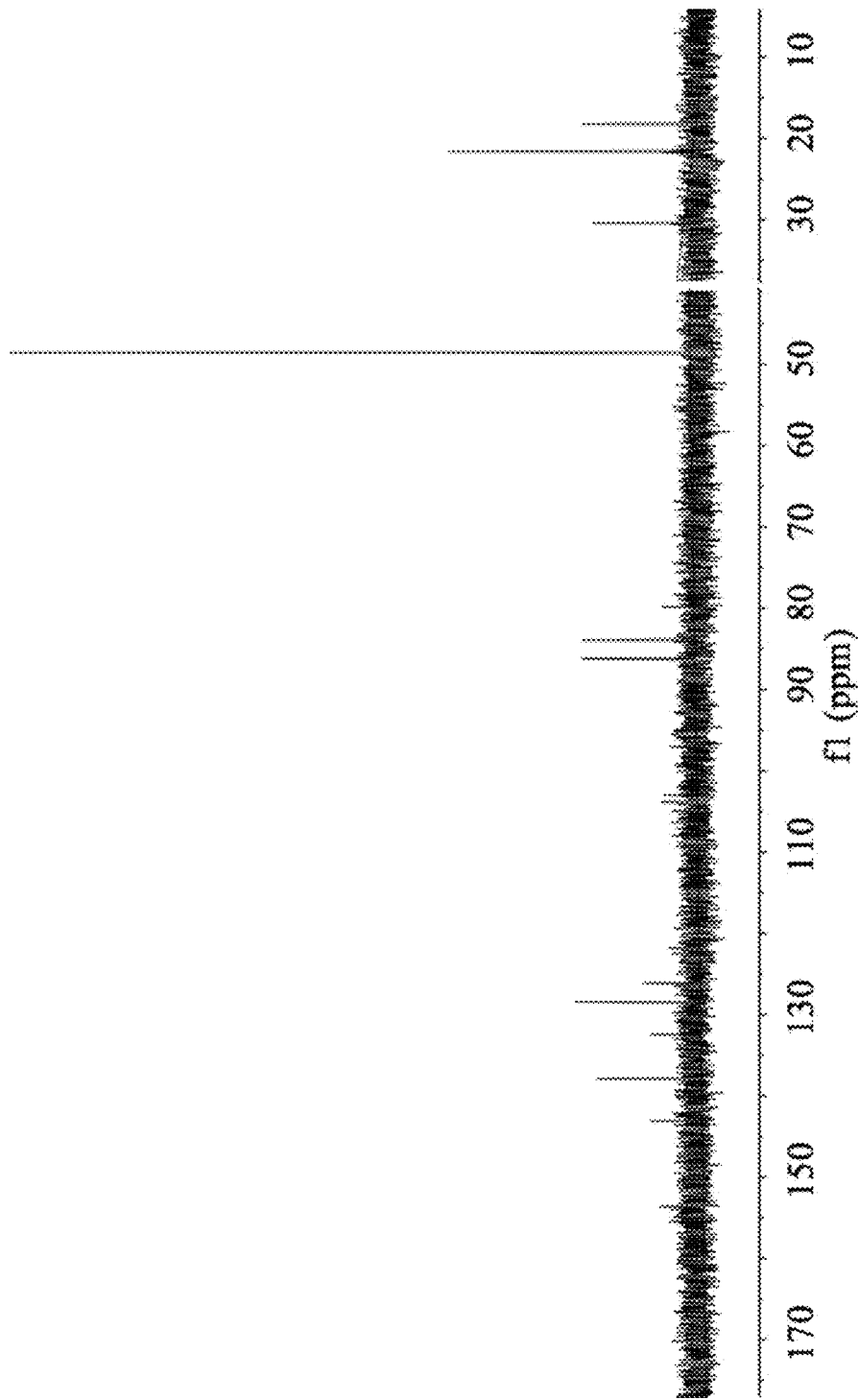
Figure 51 The $^{13}$C NMR spectra of RAP073

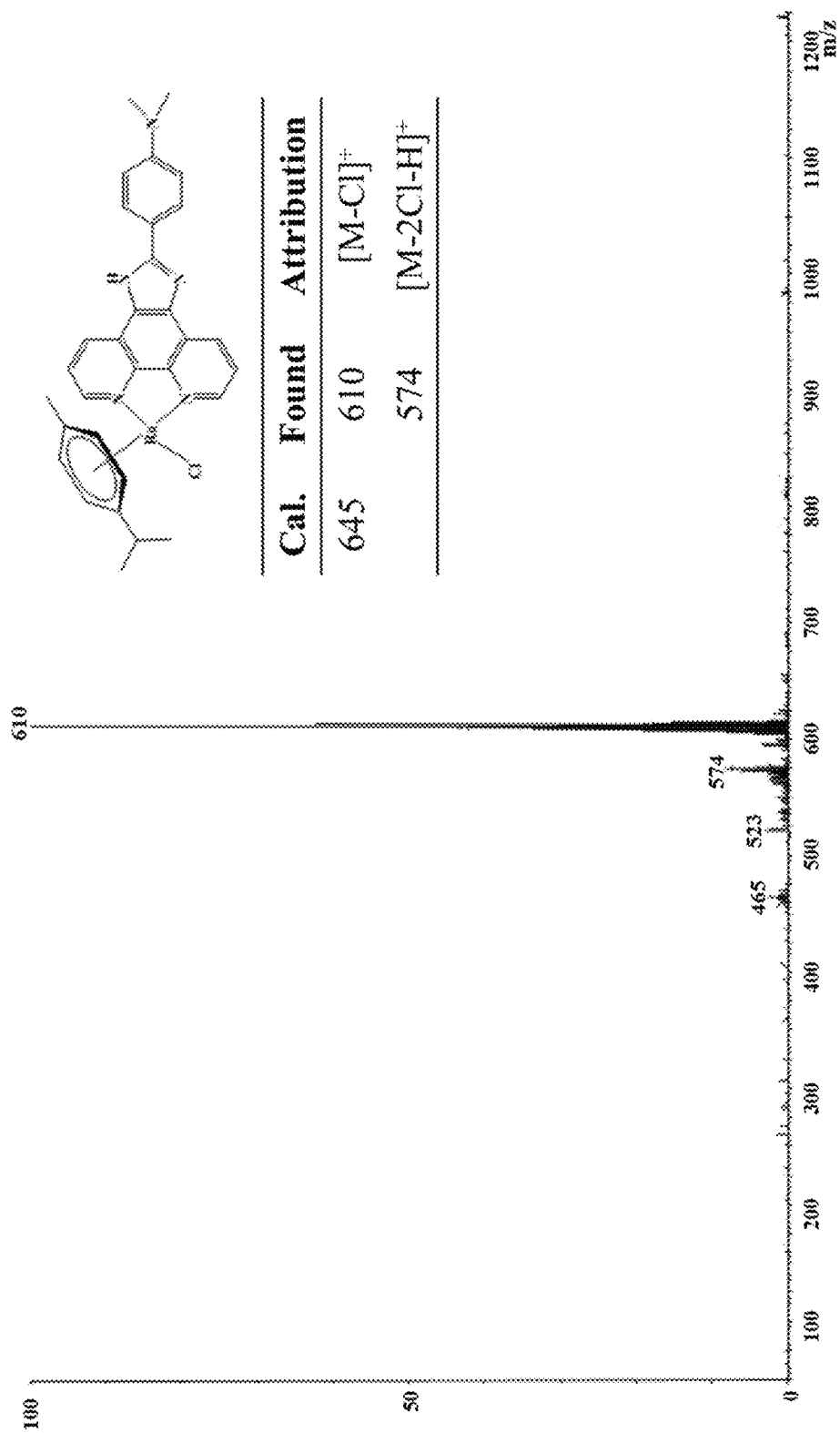
Figure 52 The ESI-MS spectra of RAP093

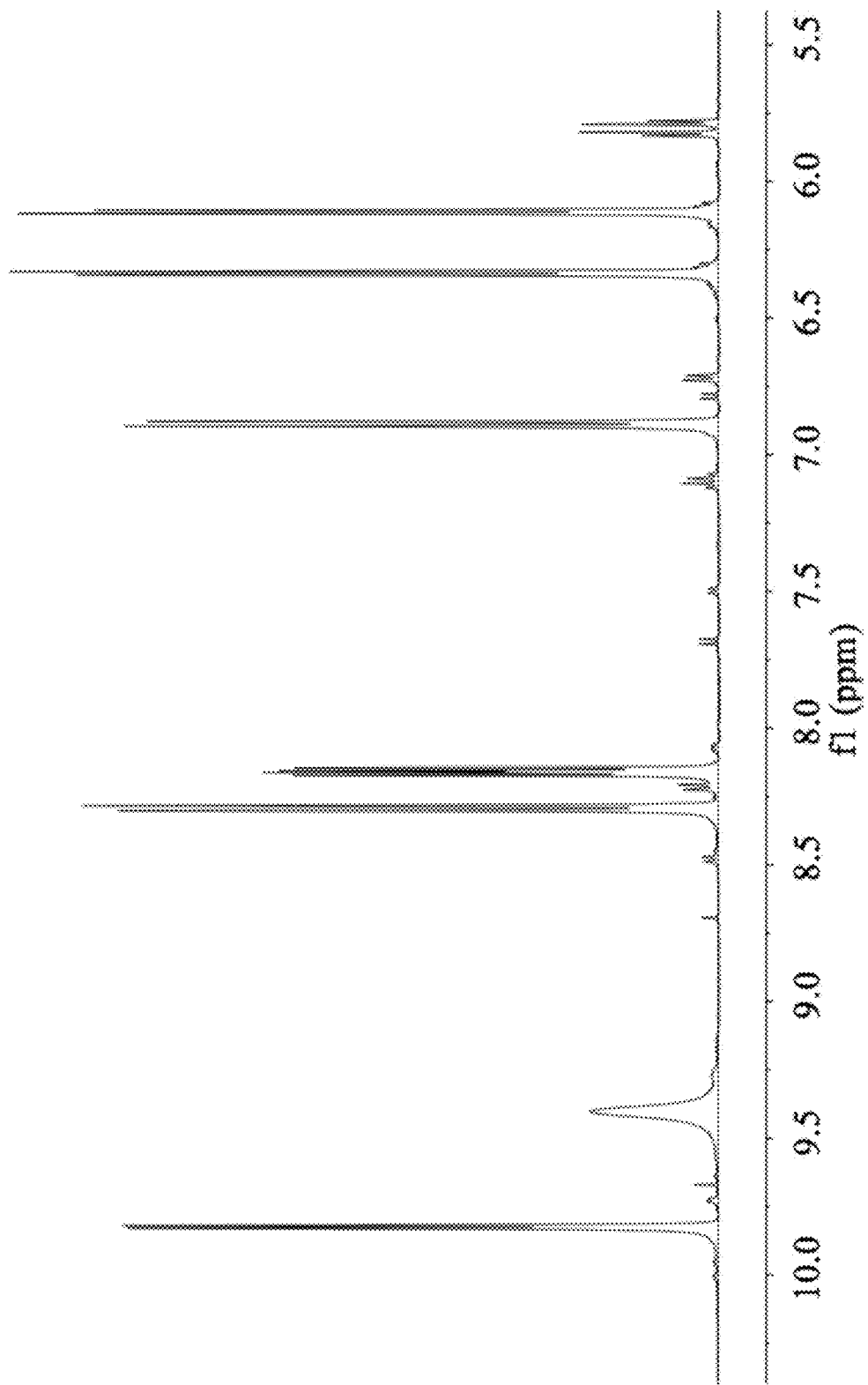
Figure 53 The $^1$H NMR spectra of RAP093

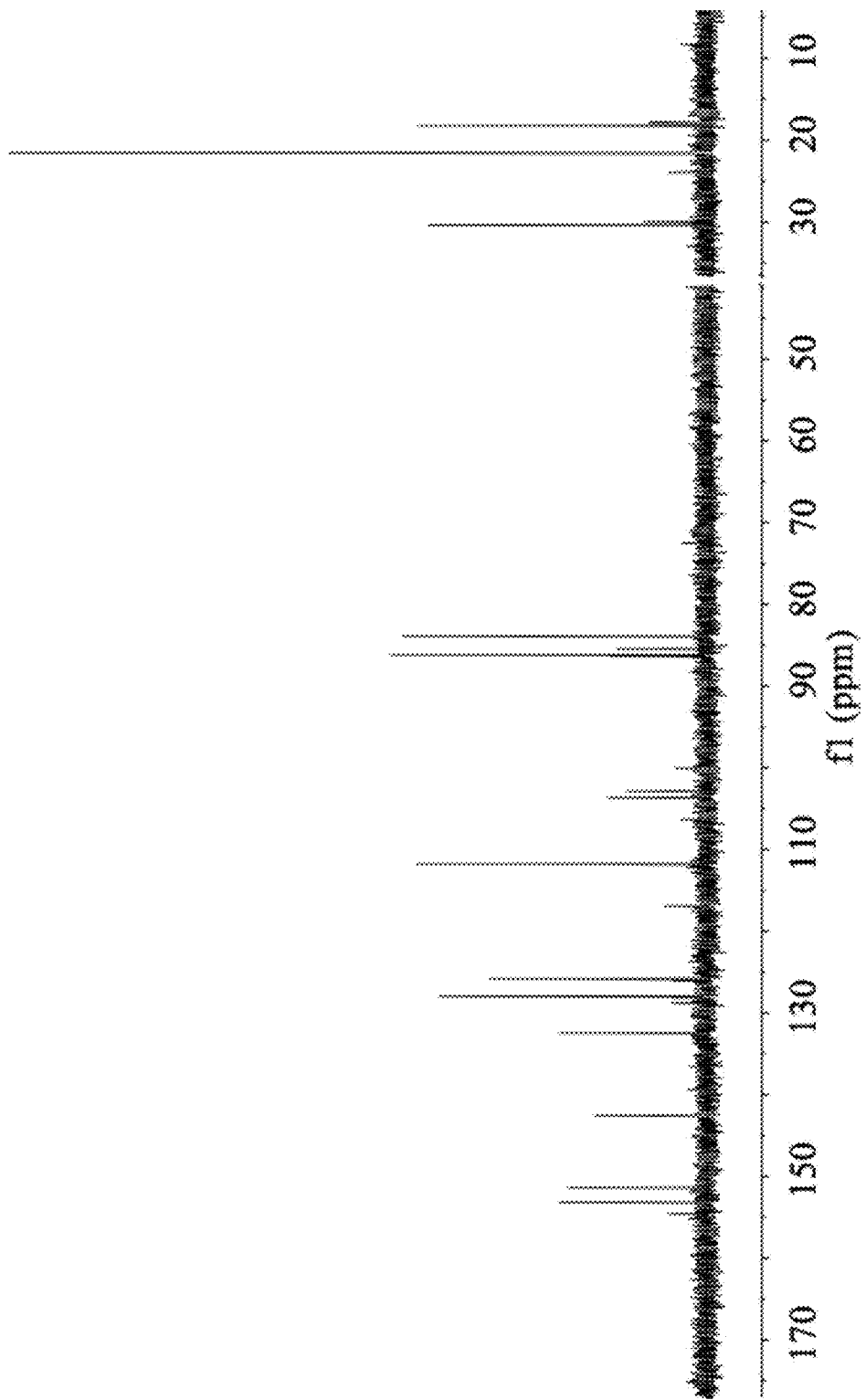
Figure 54 The $^{13}C$ NMR spectra of RAP093

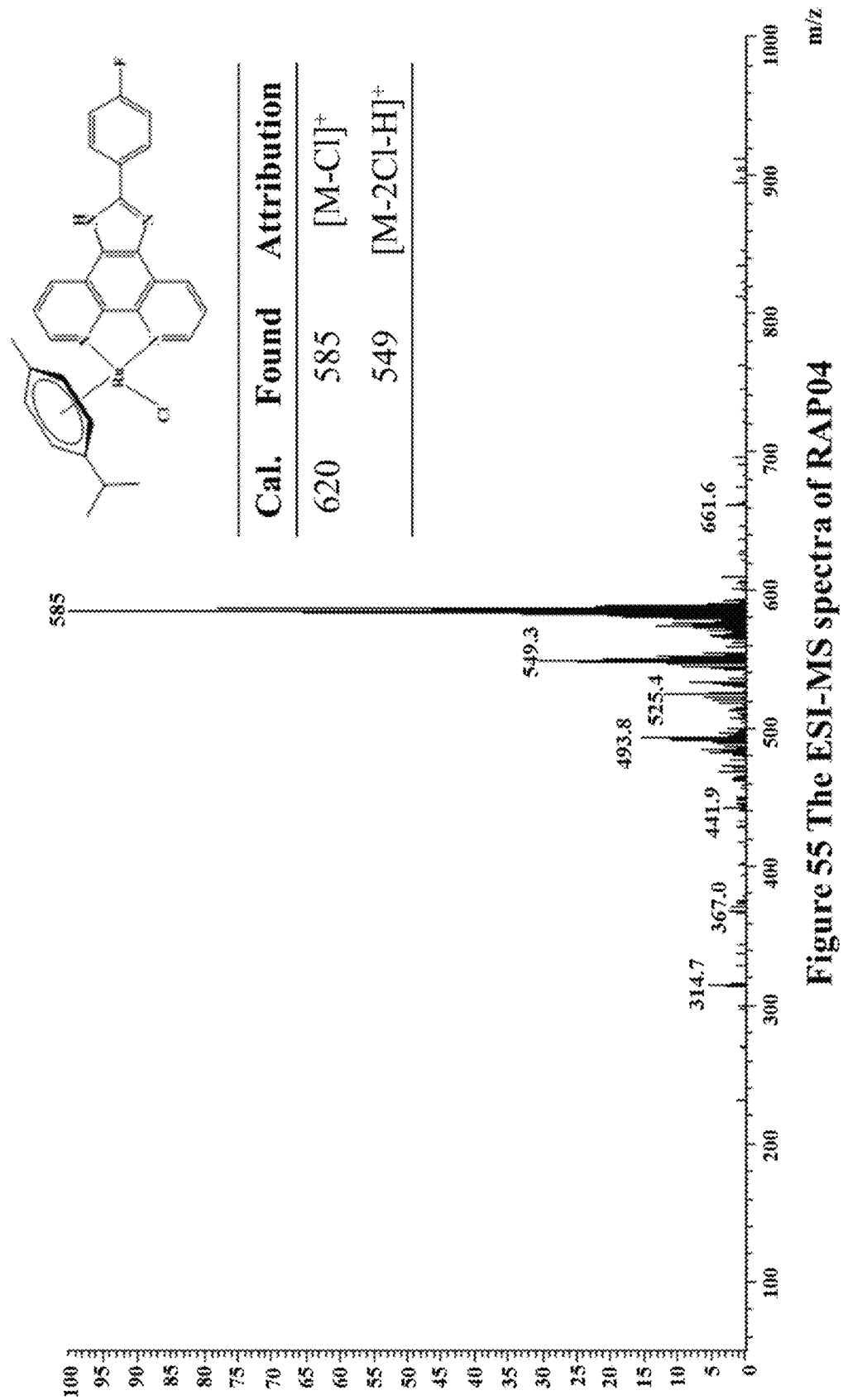
Figure 55 The ESI-MS spectra of RAP04

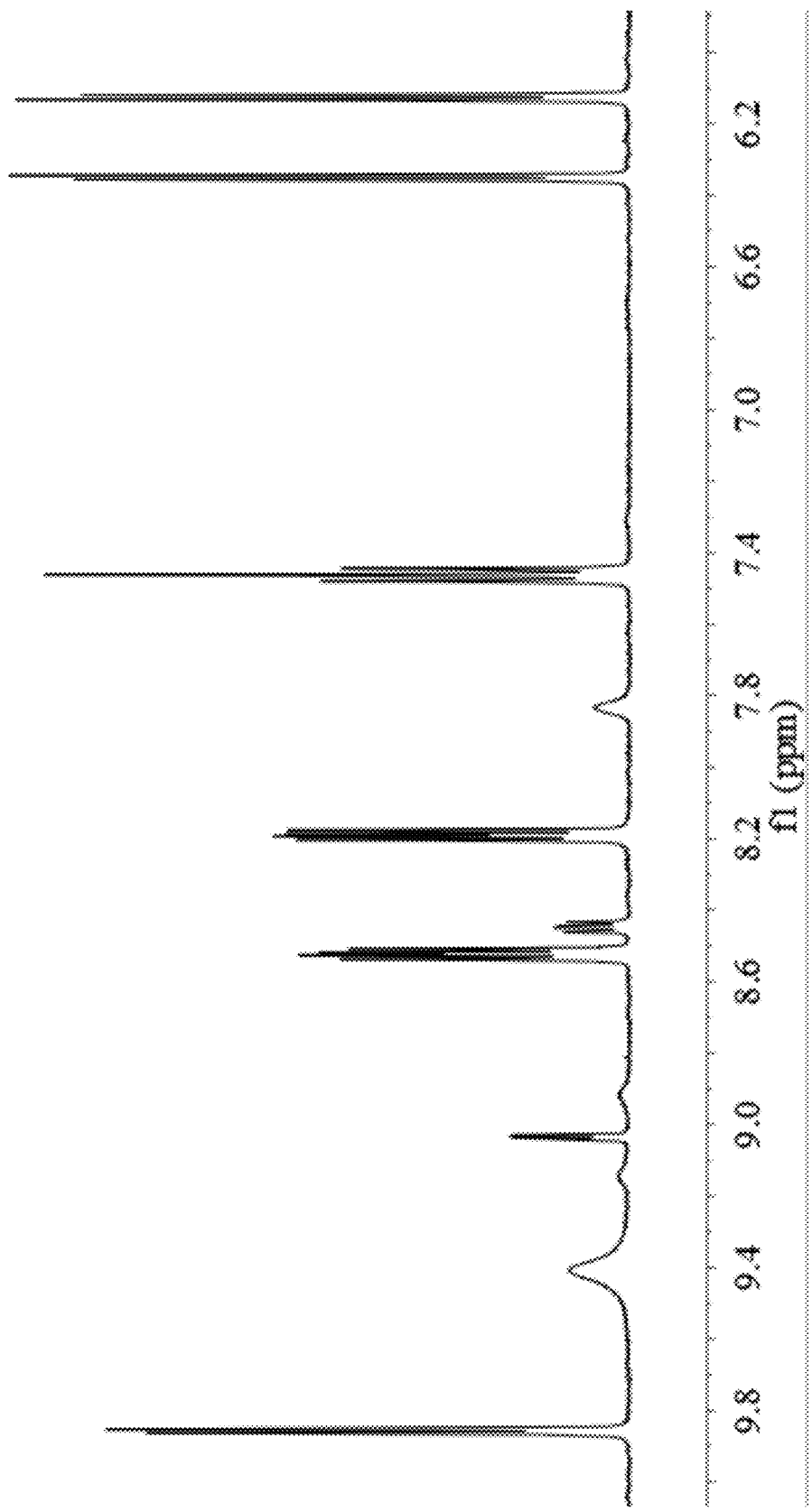

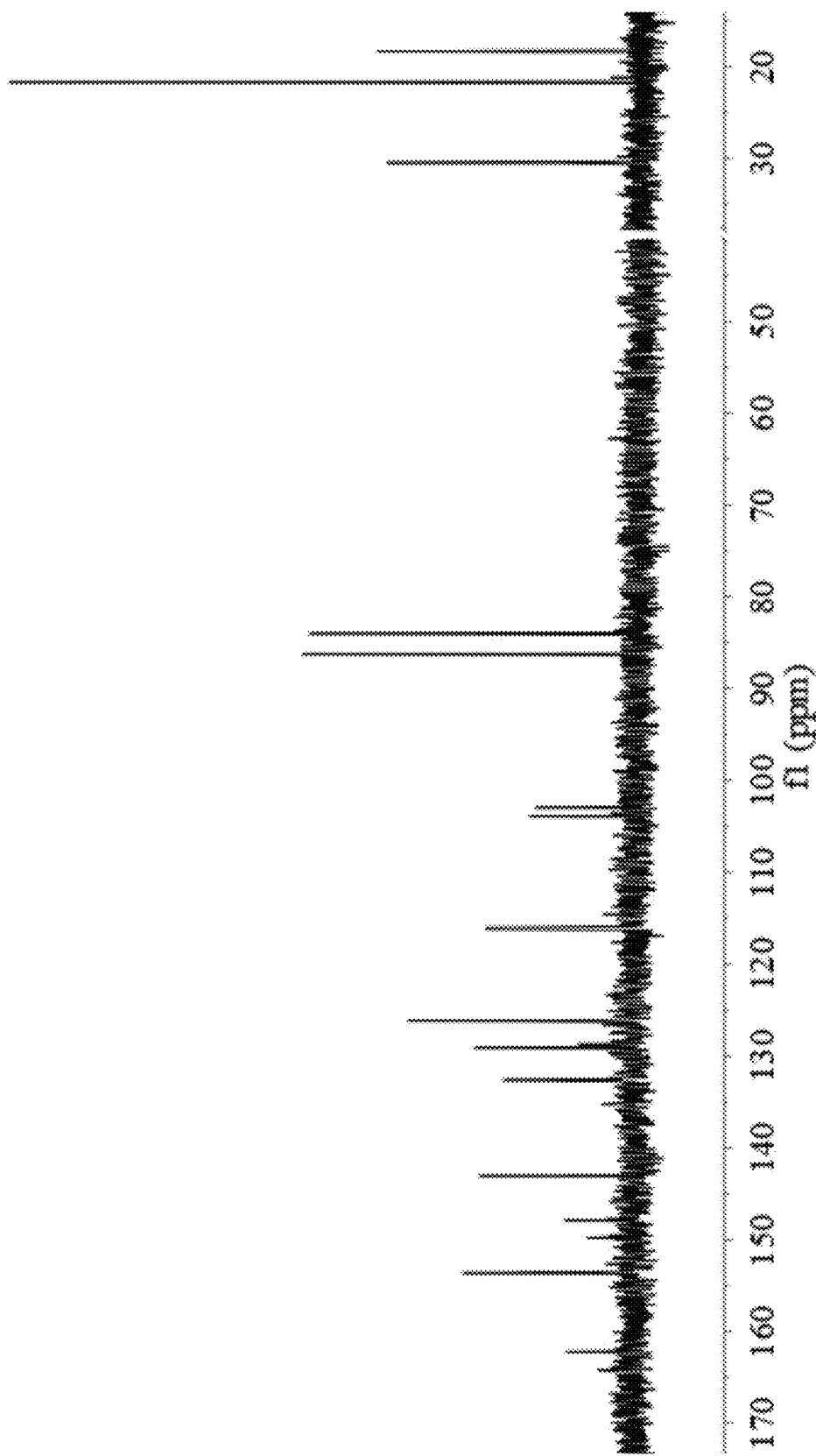
Figure 57 The $^{13}$C NMR spectra of RAP04

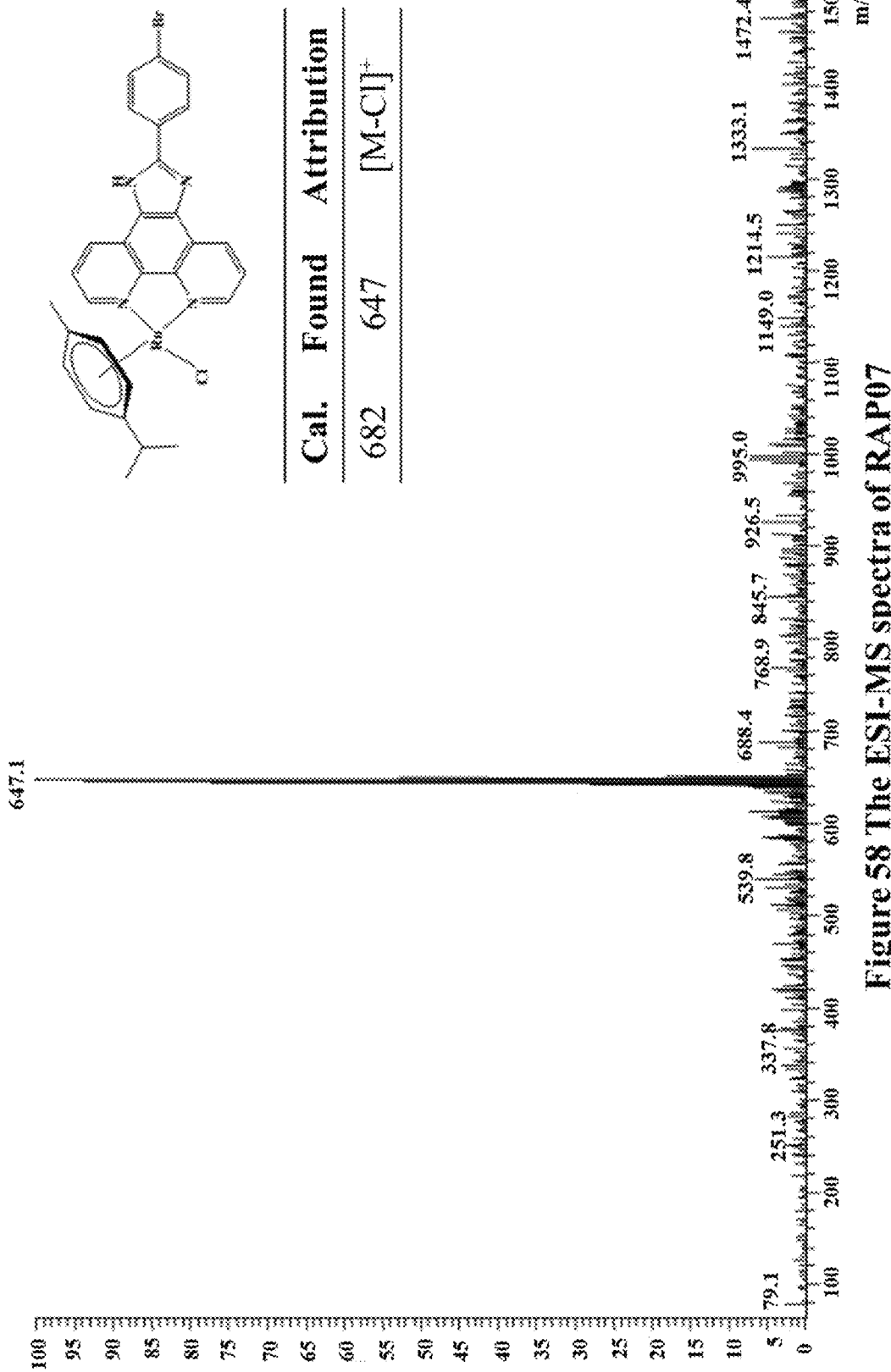
Figure 58 The ESI-MS spectra of RAP07

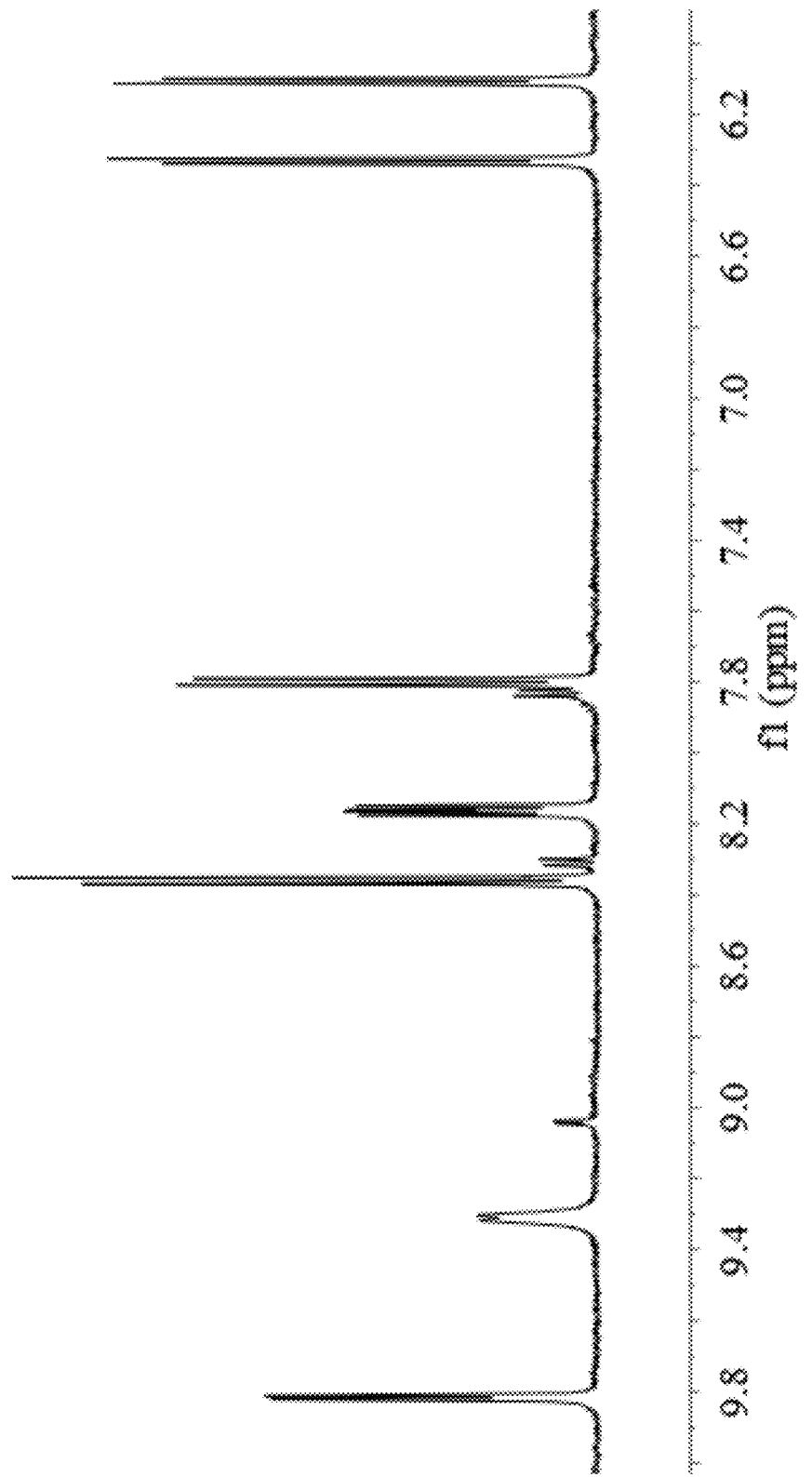
Figure 59 The $^1$H NMR spectra of RAP07

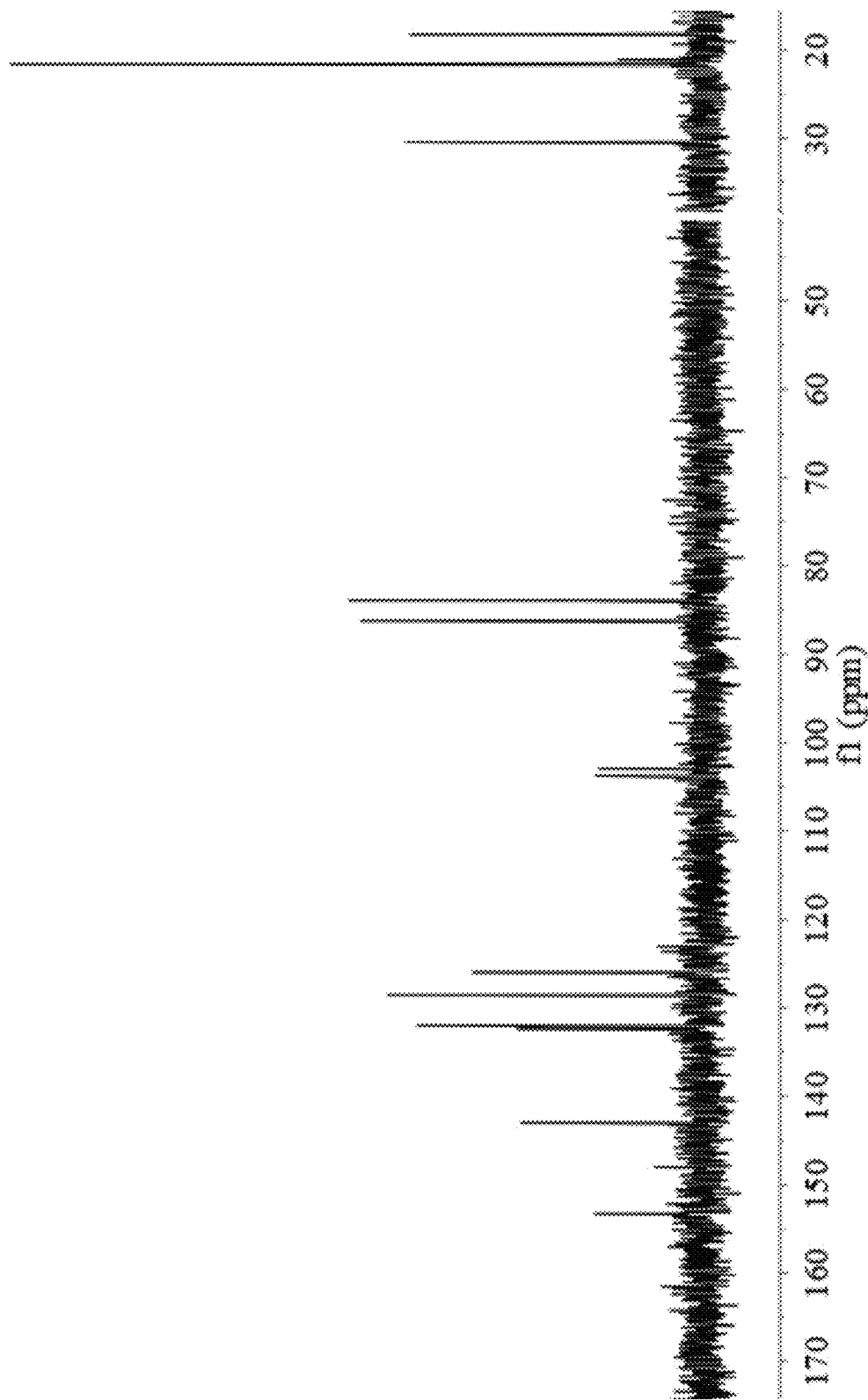
Figure 60 The $^{13}$C NMR spectra of RAP07

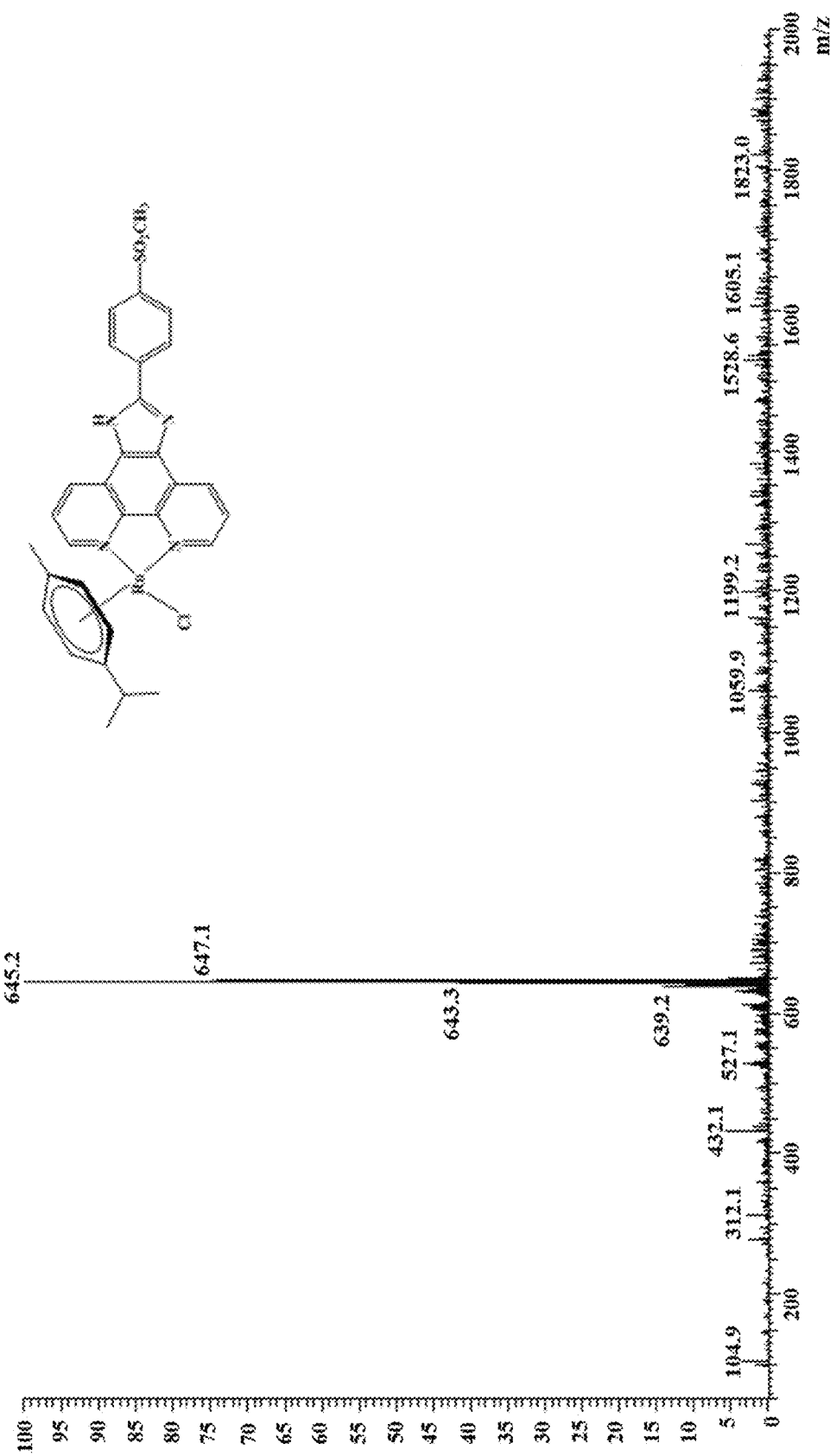
Figure 61 The ESI-MS spectra of RAP22

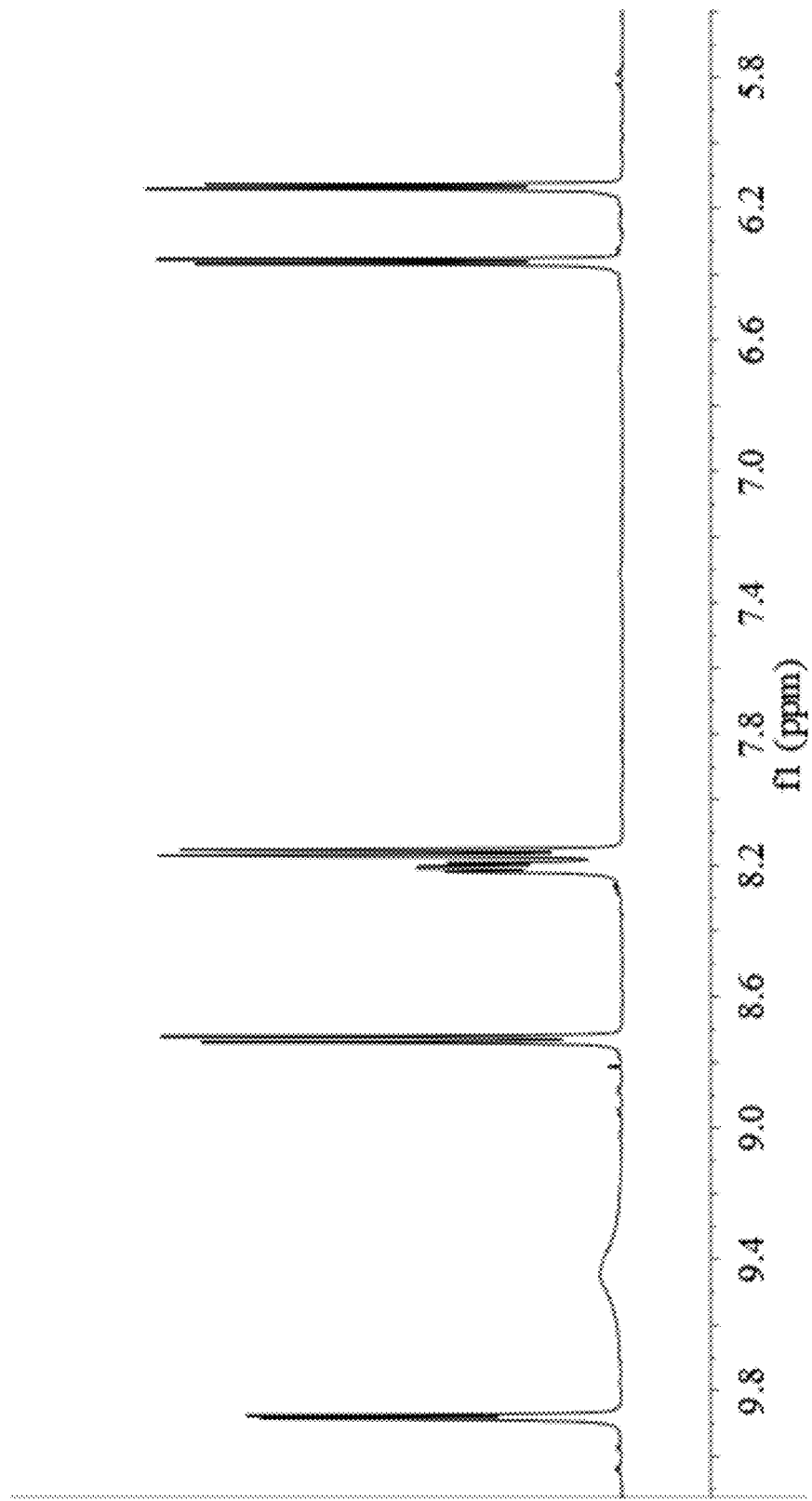
Figure 62 The $^1$H NMR spectra of RAP22

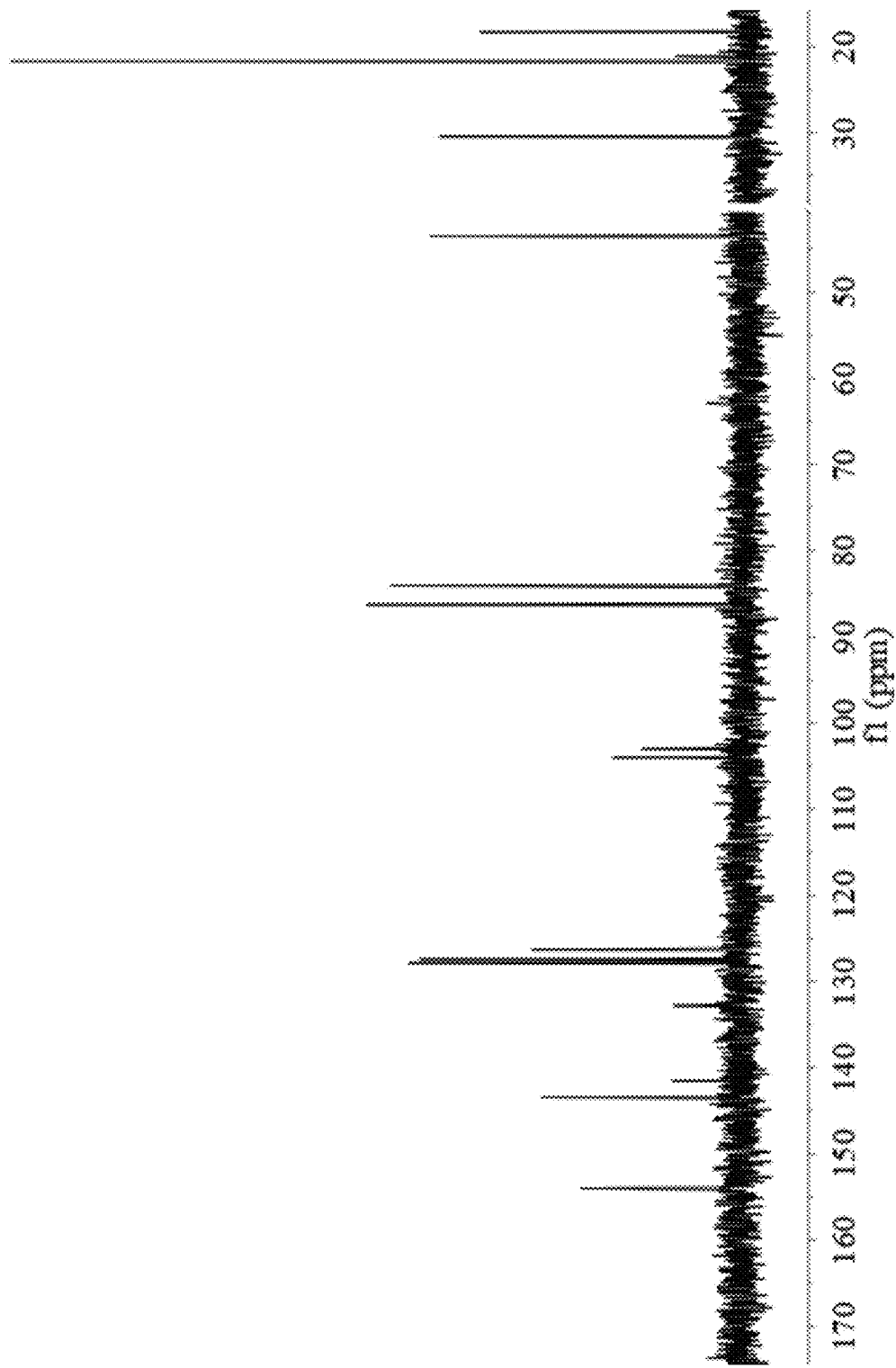
Figure 63 The $^{13}$C NMR spectra of RAP22

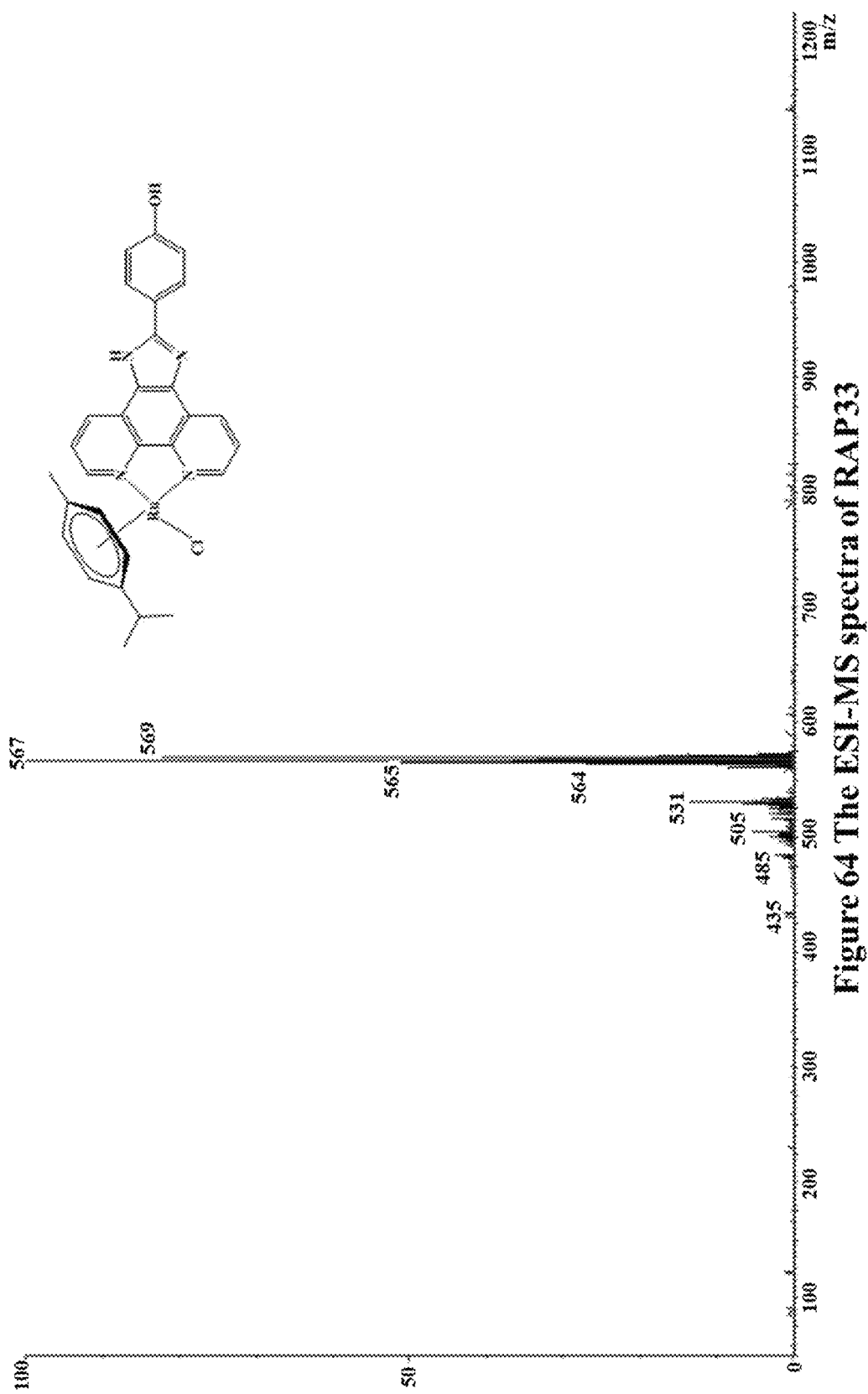
Figure 64 The ESI-MS spectra of RAP33

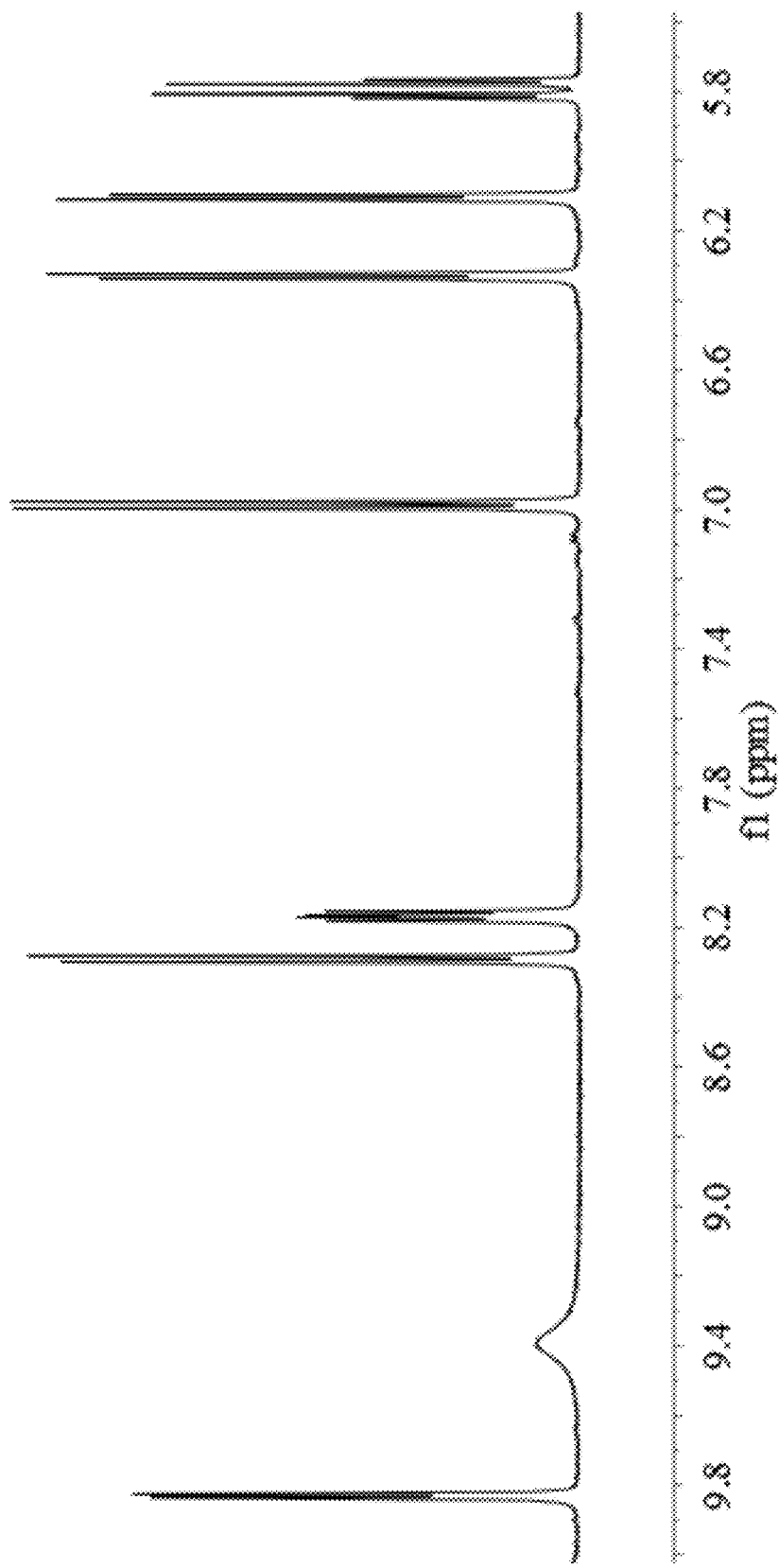
Figure 65 The $^1$H NMR spectra of RAP33

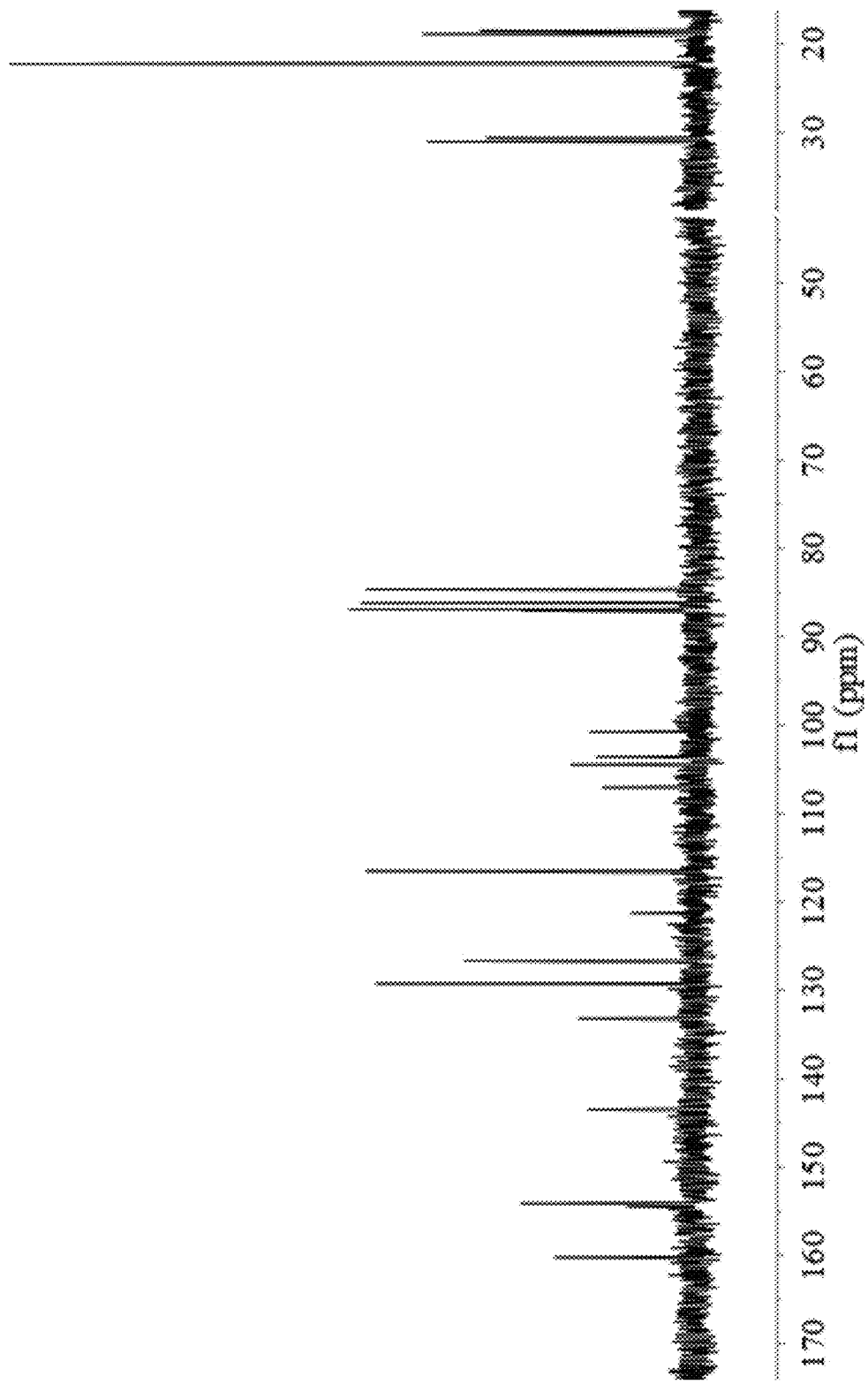
Figure 66 The $^{13}$C NMR spectra of RAP33

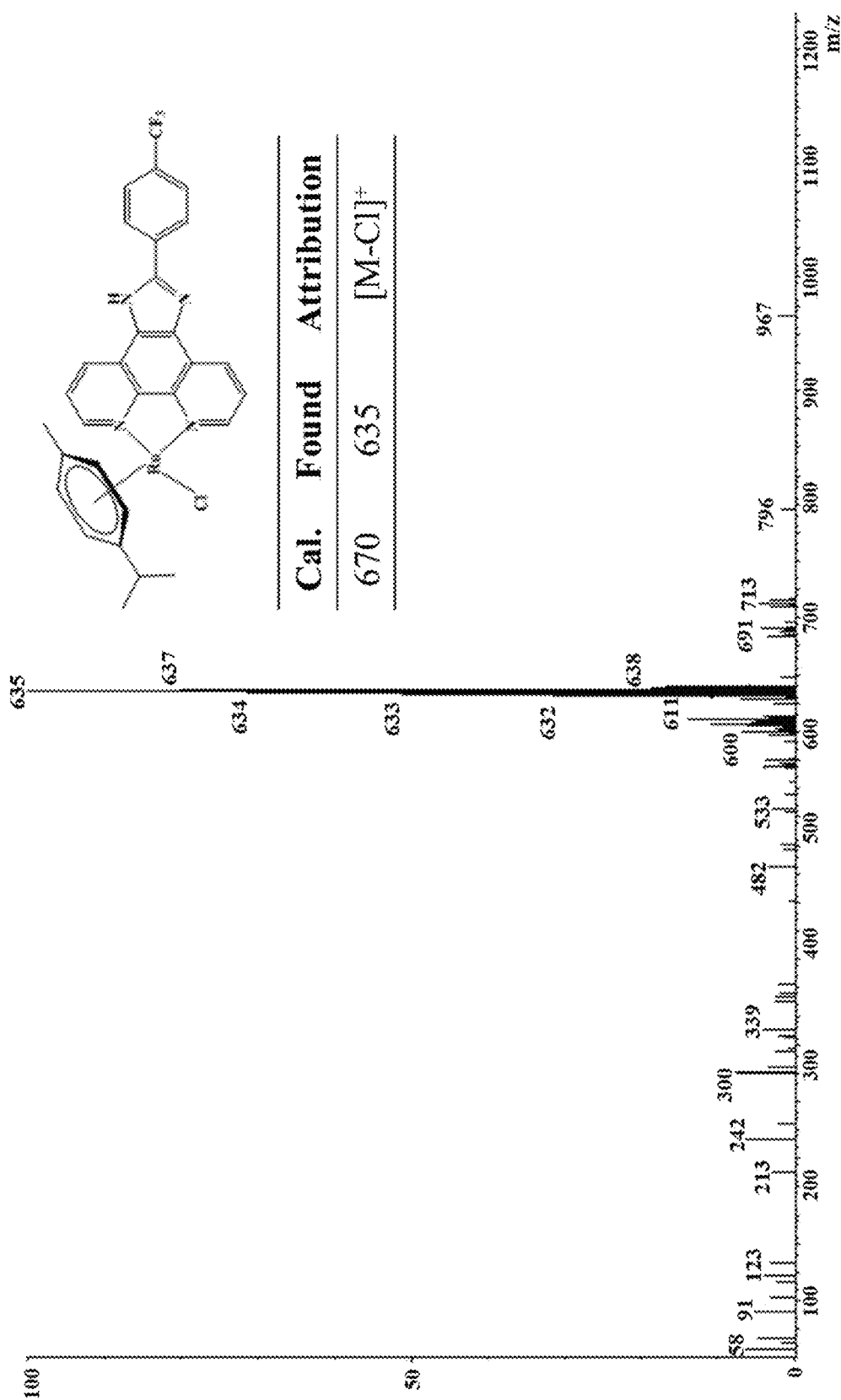
Figure 67 The ESI-MS spectra of RAP83

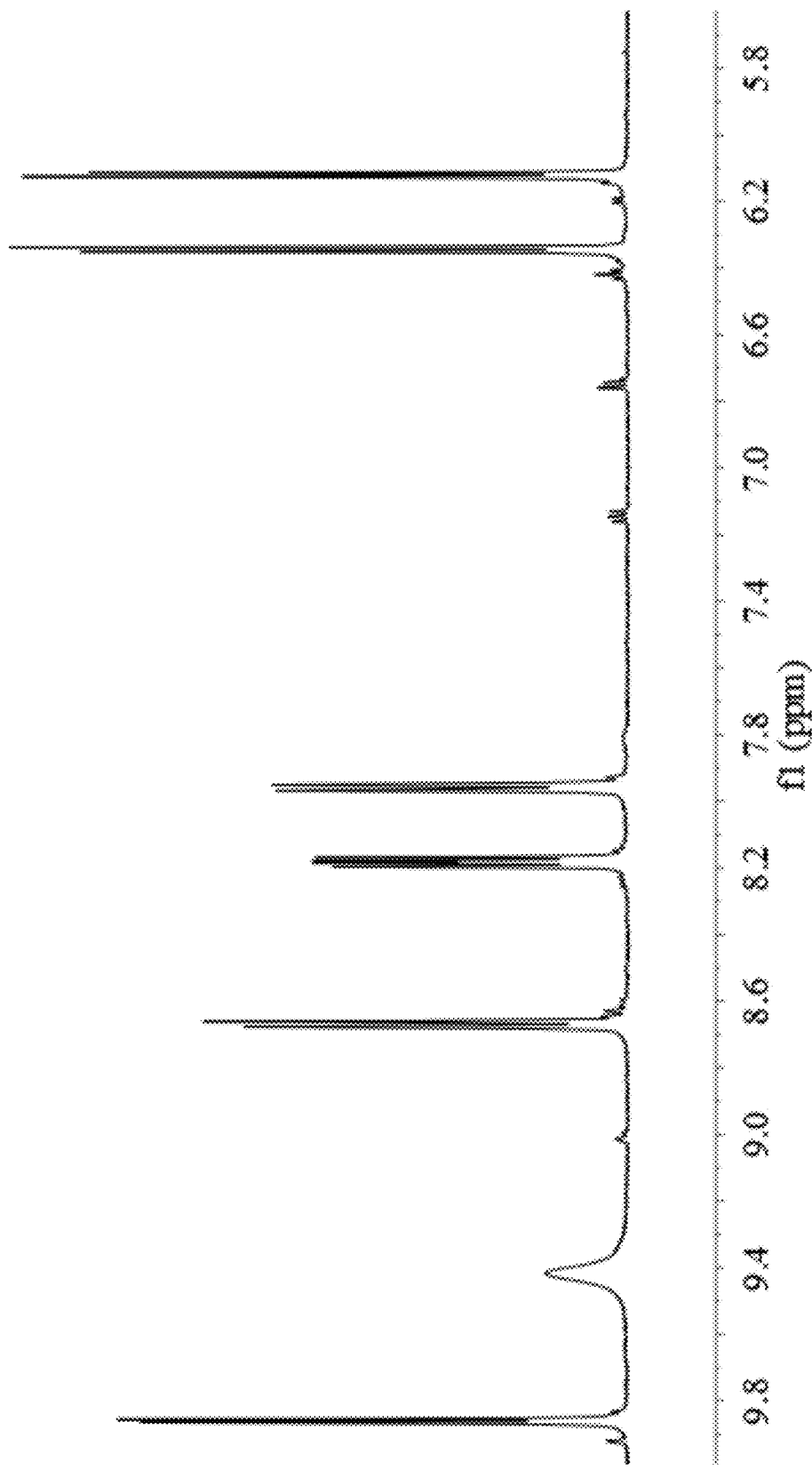
Figure 68 The $^1$H NMR spectra of RAP83

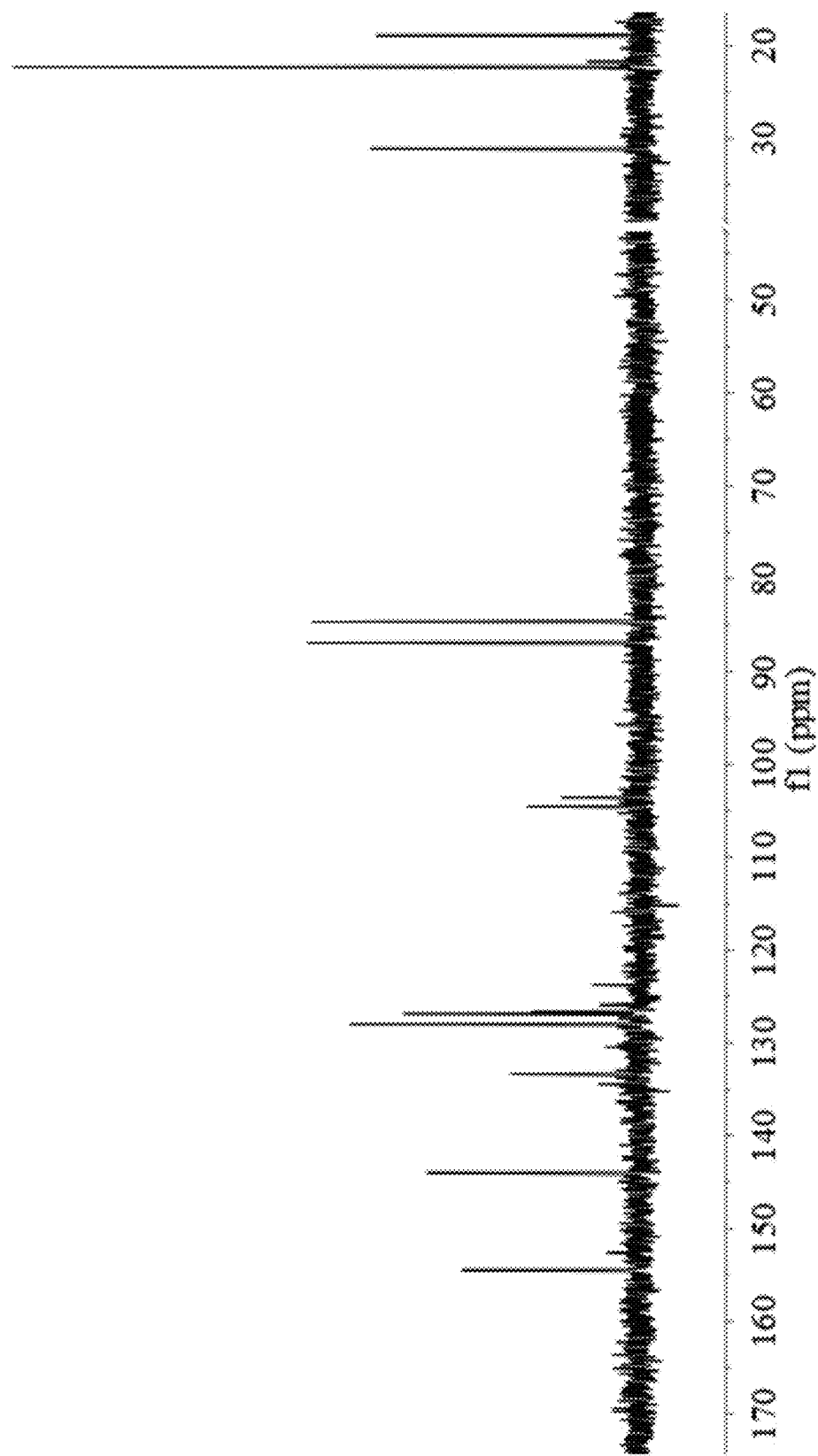
Figure 69 The $^{13}C$ NMR spectra of RAP83

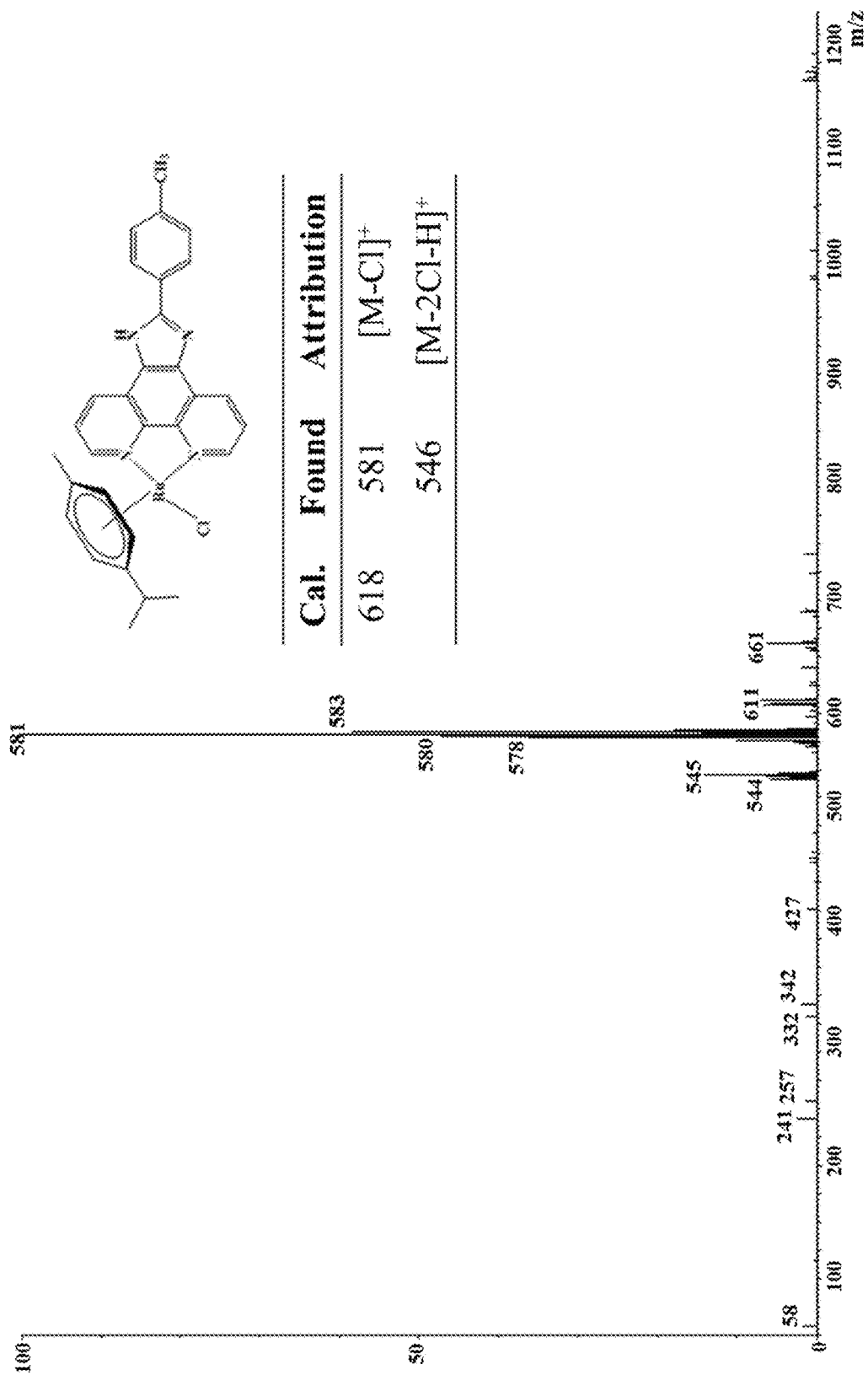
Figure 70 The ESI-MS spectra of RAP27

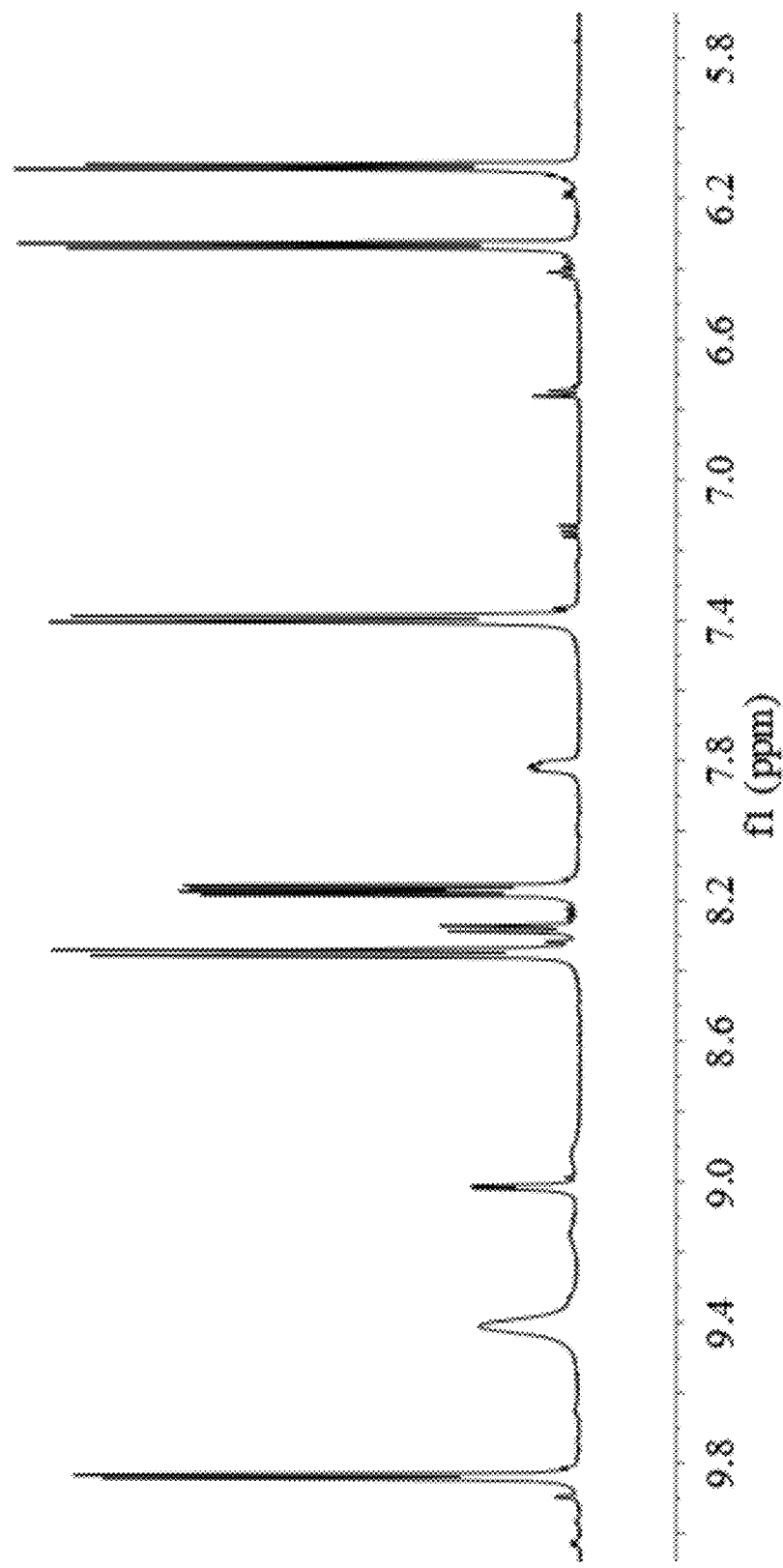
Figure 71 The $^1$H NMR spectra of RAP27

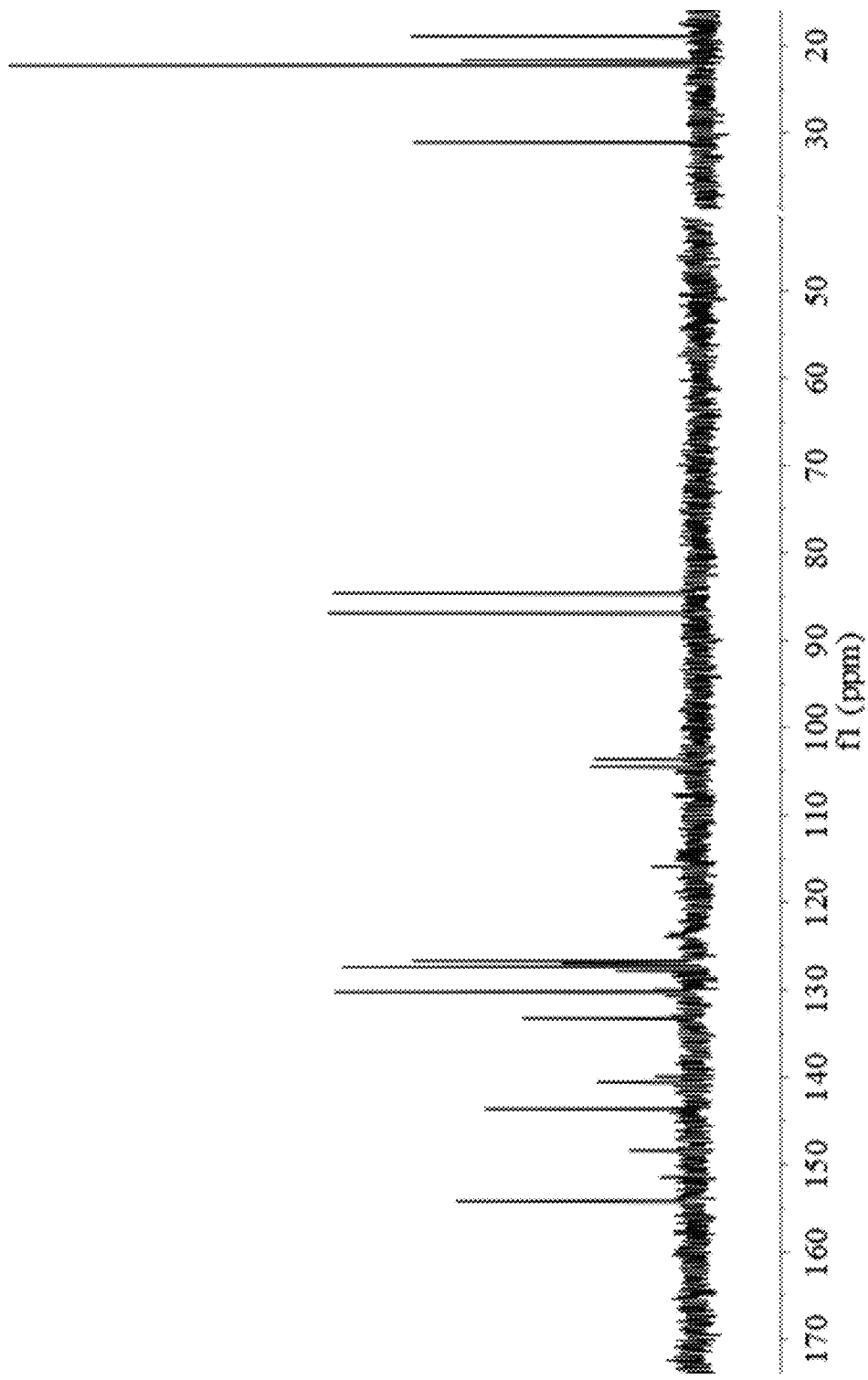
Figure 72 The $^{13}$C NMR spectra of RAP27

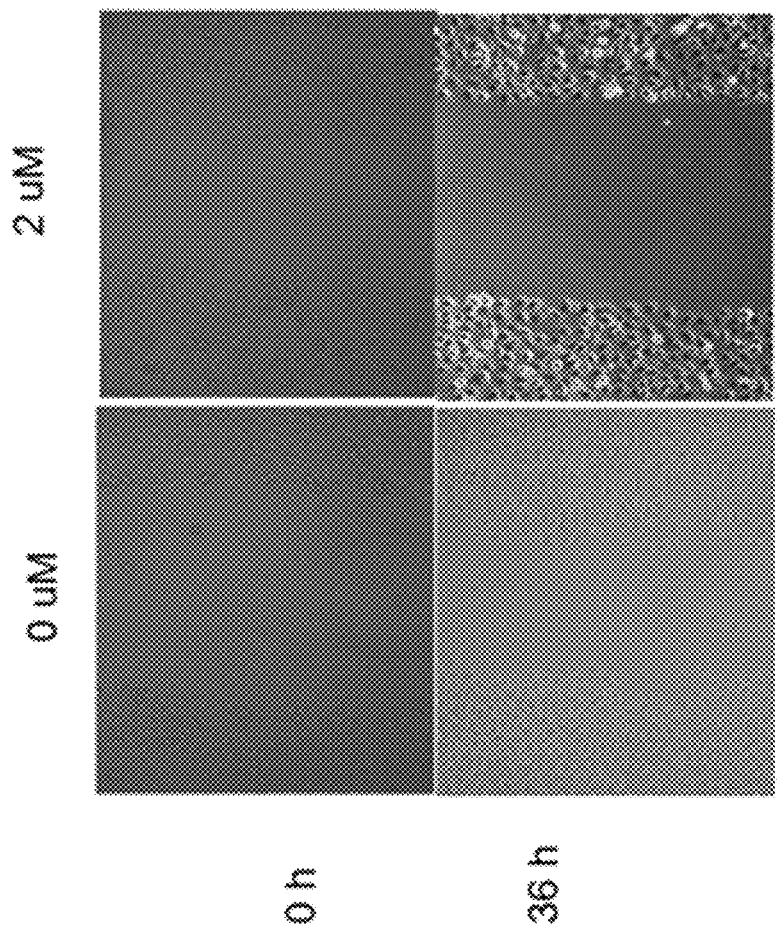
Figure 73 The antimigration ability contrast map of arene ruthenium(II) complex RAP07 against MDA-MB-231 cells

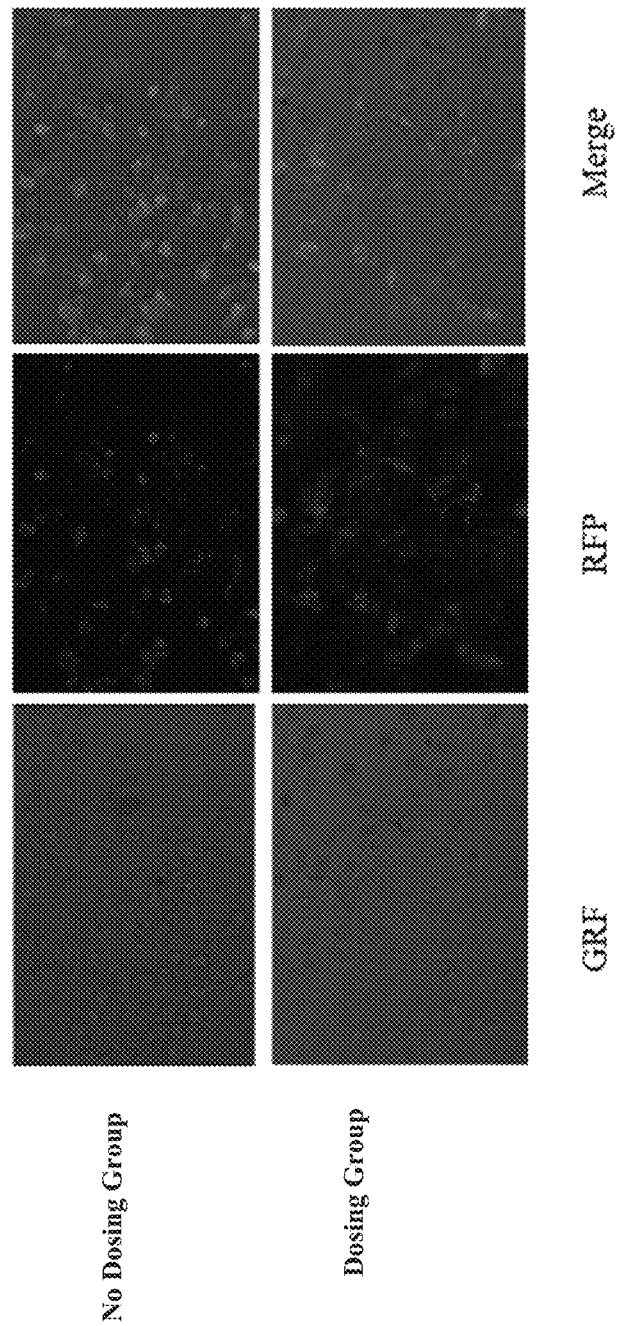
Figure 74 The suppression of invasion ability contrast map ability of arene ruthenium(II) complex RAP07 against MDA-MB-231 cells

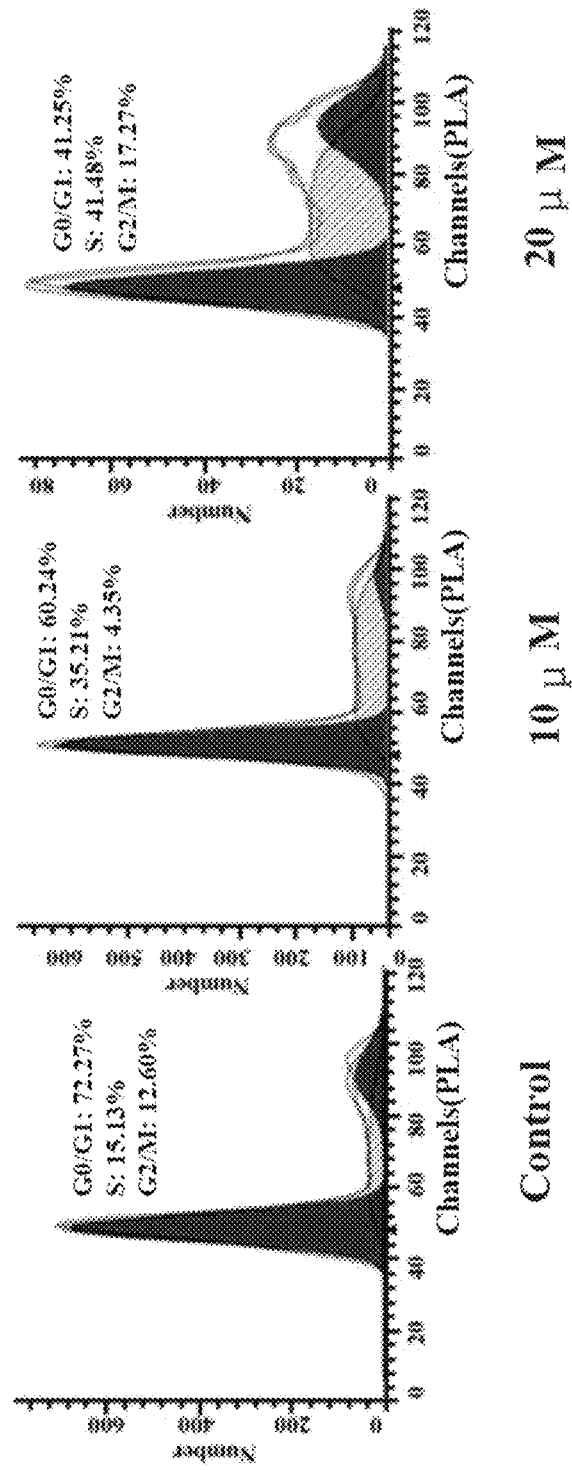
Figure 75 The measurement of the content of apoptotic cells with sub-diploid DNA of in Example 38 and the effect of cell cycle distribution

ARENE RUTHENIUM COMPLEX, PREPARATION METHOD AND UTILIZATION THEREOF

CROSS REFERENCE TO RELATED APPLICATIONS

This application is based upon and claims priority to Chinese Patent Application No. 2017103607965, filed on May 19, 2017, the entire contents of which are incorporated herein by reference.

TECHNICAL FIELD

The present invention relates to the technical field of synthetic chemistry, and particularly relates to an arene ruthenium complex, preparation method and utilization thereof.

BACKGROUND

Arene ruthenium complex has the classical "piano stool" geometry. The arene ruthenium complex is a small molecular organometallic compound which forms a covalent bond through π-orbital electron on benzene ring and the center metal ruthenium, wherein the auxiliary ligand is benzene or substituted benzene with strong hydrophobicity. The synthesis of various types of arene ruthenium complexes and utilization thereof as an anticancer agent have been reported in a large amount of literature, both at home and abroad, since the first synthesis of arene ruthenium (II) complexes by Winkhaus and Singer in 1967.

Kondapi et al. reported that arene ruthenium complexes represented by $[(\eta^6-C_6H_6)Ru(DMSO)Cl_2]_2{}^+$ have showed good inhibitory effect on Colo-205 human colon carcinoma cells and ZR-75-1 breast cancer cells, strong affinity for DNA, and inhibiting the growth and proliferation of tumor cells by inhibiting the activity of topoisomerase II. [Vashisht G Y N, Konuru N, KondapiAK. Topoisomerase II antagonism and anticancer activity of coordinated derivatives of $[RuCl_2(C_6H_6)(dmso)]$. [J]. *Arch. Biochem. Biophys*, 2002, 401(1):53-62].

A class of arene ruthenium (II) complexes with amantadine ligands reported by Dyson et al. were synthesized by heating and refluxing a mixture of $[RuCl_2(\eta^6\text{-arene})]_2$ (0.64 mmol) and PTA (1.28 mmol) in methanol solvent for 24 h with a yield of 85-95%. [Scolaro C, Bergamo A, Brescacin L, Delfino R, Cocchietto M, Laurenczy G, Geldbach T J, Sava G, Dyson P J. In vitro and in vivo evaluation of ruthenium(II)-arene PTA complexes. [J]. *J Med Chem*, 2005, 48: 4161-4171]. This class of complexes exhibit growth inhibitory activity against TS/A cell ($IC_{50}$ 60~300 μM) and low toxicity to normal human cells ($IC_{50}$>300 μM). Wherein the complexes RAPTA-B ($[Ru(\eta^6-C_6H_6)(pta)Cl_2]$) and RAPTA-C($[Ru(\eta^6-p-C_6H_4MeiPr)(pta)Cl_2]$) induce G2/M phase arrest and apoptosis in cancer cells by regulating various signal pathways of mitochondrial and P53-JNK, increasing p21 level and reducing the amount of Cyclins E[Chatterjee S, Kundu S, Bhattacharyya A, Hartinger C G, Dyson P J, The ruthenium(II)-arene compound RAPTA-C induces apoptosis in EAC cells through mitochondrial and p53-JNK pathways. [J]. *J Biol Inorg Chem*, 2008, 13:1149-1155]. Moreover, in vivo studies showed that RAPTA-C can inhibit the proliferation and metastasis of MCa breast cancer in CBA mice through inhibiting angiogenesis [Nowak-Sliwinska P, Van B J R, Casini A. Organometallic ruthenium (II) arene com-pounds with antiangiogenic activity[J]. *J. Med. Chem*. 2011, 54(11):3895-3902].

The arene ruthenium (II) complexes with ethylenediamine ligand reported by Sadler et al. were synthesized by adding $[RuCl_2(\eta^6\text{-arene})]_2$ (0.64 mmol) and ethylenediamine derivative (2.0 mmol) into a methanol solvent, stirring for 1.5 h, adding $NH_4PF_6$, filtrating, and recrystallizing the filtrate in fridge for 6 h. The yield was 37.7%. This type of complexes exhibit effective growth inhibitory activity against A2780 human ovarian cancer cells without cross resistance. The complexes can bind to the guanines in DNA closely, which is an important strategy to develop the targeting of antitumor activity against tumor cells [Morris R E, Aird R E, del Socorro Murdoch P, Chen H, Cummings J, Hughes N D, Parsons S, Parkin A, Boyd G, Jodrel lD I, Sadler P J. Inhibition of cancer cell growth by ruthenium (II) arene complexes. *J Med Chem*, 2001, 44: 3616-3621]. Wherein the complex RM175 ($[(\eta^6\text{-biphenyl})Ru(ethylenediamine)-Cl]^+$) can inhibit tumor invasion and metastasis by promoting cell-cell re-adhesion and reducing the release of metalloproteinases (MMPs) [Bergamo A, Masi A, Peacock A F, Habtemariam A, Sadler P J, Sava G J. In vivo tumour and metastasis reduction and in vitro effects on invasion assays of the ruthenium RM175 and osmium AFAP51 organometallics in the mammary cancer model. Inorg Biochem, 2010, 104:79-86], [Habtemariam A, Melchart M, Fernandez R, Parsons S, Oswald I D H, Parkin A, Fabbiani F P A, Davidson J E, Dawson A, Aird R E, Jodrell D I, Sadler P J. Structure-activity relationships for cytotoxic ruthenium (II) arene complexes containing N,N-, N,O-, and O,O-chelating ligands. J. Med Chem, 2006, 49: 6858-6868].

Another type of arene ruthenium (II) complexes $[(\eta^6\text{-arene})Ru(\beta\text{-diketonate})Cl]$ with 2,4-pentanedione ligand reported by Sadler et al. were obtained by mixing and stirring $[RuCl_2 (\eta^6\text{-arene})]$ and sodium acetylacetonate in acetone for 50 min. The yield was 61.2%. The $IC_{50}$ values of these complexes in the human ovarian cancer line A2780 in vitro are determined by the types of auxiliary ligands of the arene ring. The complexes with an arene ring of p-cymene ligand has a highest antitumor activity compared to those with other ligands, wherein the complex $[(\eta^6\text{-p-cymene}) Ru (\beta\text{-diketonate}) Cl]$ exhibits effective antitumor activity against the human ovarian cancer cell line A2780 with $IC_{50}$ of 17 μM.

The arene ruthenium (II) complexes with carboline ligand reported by Mao et al. were obtained through refluxing $[RuCl_2(\eta^6\text{-arene})]$ and carboline derivative in methanol for 2.5 h. The yield was 78%. The in vitro antitumor activity of this type of complexes is 3 to 12 times higher than that of cisplatin against tumor cell lines in vitro, but much lower cytotoxic against normal cells, as well as no cross-resistance to cisplatin was found. Especially, the complexes exhibit high antitumor activity against cisplatin-resistant cell lines A549cisR, and low toxicity to normal human nonfibroblast cell lines HLF. The complexes may directly target CDK1 (cyclin-dependent kinase) by downregulating the expression of CDK1 and cyclin B1, induce G2M phase arrest block in cancer cells. Furthermore, the complexes can effectively induce apoptosis through mi-tochondrial-related pathways and increase the amount of intracellular reactive oxygen species (ROS) elevation [He L, Liao S Y, Tan C P, Ye R R, Xu Y W, Zhao M, Ji L N, Mao Z W. Ruthenium-Arene-β-Carboline Complexes as Potent Inhibitors of Cyclindependent Kinase 1: Synthesis, Characterization and Anticancer Mechanism Studies. Chem. Eur. J, 2013, 19, 12152-12160].

Three ruthenium arene complexes with thiosemicarbazones ligand [(η⁶-p-cymene)Ru(R-BzTSC)Cl]Cl (BzTSC=benzaldehyde thiourea, R=H, CH$_3$ and C$_6$H$_5$) reported by Su et al. were obtained through refluxing [RuCl$_2$ (η⁶-p-cymene)] (0.05 mmol) and benzaldehyde thiourea (0.1 mmol) in acetone for 6 h at 45° C. The yield was 39%. These types of arene ruthenium complexes exhibit effective anti-proliferative activity against nasopharyngeal carcinoma, lung cancer, breast cancer and ovarian cancer cells. Wherein the complexes [(η⁶-p-cymene)Ru(C$_6$H$_5$-BzTSC) Cl]Cl exhibit most effective anti-proliferative activity with IC$_{50}$ values of 20 μM, 31 μM, 10 μM and 34 μM, respectively [Su W, Zhou Q, Huang Y M, et al. Synthesis, crystal and electronic structure, anticancer activity of ruthenium(II) arene complexes with thiosemicarbazones[J]. *Appl. Organometal. Chem.* 2013, 27(5): 307-312.].

Due to differences in ligands, the arene ruthenium complexes presented usually have different anticancer activities against various tumor cell lines. Therefore, specific to different tumor symptoms, developing different types of ruthenium arene complexes is necessary.

SUMMARY

One of the purposes of the present invention is to provide a novel type of arene ruthenium complexes which exhibit high inhibitory activity against various tumor cell lines.

To address above technical problems, the present invention is implemented by the following technical scheme: a novel arene ruthenium complex, comprising R$_1$, R$_2$, R$_3$, and PIP as main ligands, wherein the main ligand has a molecular structure as follows:

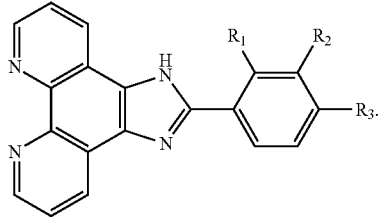

Wherein R$_1$, R$_2$, R$_3$ are selected from —H, —Cl, —F, —Br, —I, —CF$_3$, —NO$_2$, —OCH$_3$, —OH, —COOH, —CH$_3$, —N(CH$_3$)$_2$, —C$_2$H$_2$, —SO$_2$CH$_3$, alkanes with 1 to 6 carbon atoms, substituted alkyl with 1 to 6 carbon atoms, phenyl, substituted phenyl, pyridyl, substituted pyridyl, furyl, substituted furyl, pyrrolyl, substituted pyrrolyl, thiazyl or substituted thiazyl group respectively. The substituted groups in the substituted phenyl, substituted pyridyl, substituted furyl, substituted thiazyl and substituted pyrrolyl are selected from hydroxyl, nitro, halogen, amido, carboxyl, cyano, thiol, naphthene group with 3 to 8 carbon atoms, SO$_3$H, alkanes with 1 to 6 carbon atoms, alkenyl with 2 to 6 carbon atoms, alkyne with 2 to 6 carbon atoms, C$_1$-C$_6$ hydroxyalkanes, C$_1$-C$_6$ aminoalkanes, CO2R', CONR'R', COR', SO2R'R', C$_1$-C$_6$ alkoxyl, C$_1$-C$_6$ alkyl thiol, —N=NR', —NR'R' or C$_1$-C$_6$ trifloroalkyl respectively. The R' group is selected from H, alkyl with 1 to 6 carbon atoms or phenyl respectively.

Further, the arene ruthenium complex has a chemical formula of [(η⁶-p-cymene)Ru(RPIP)Cl]Y, wherein the R includes R$_1$, R$_2$ and R$_3$. The arene ruthenium complex has the molecular structure of:

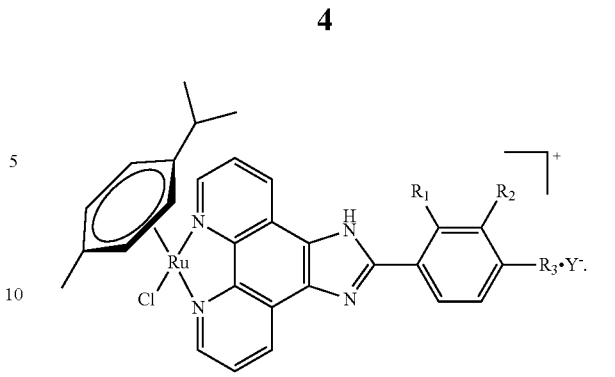

Wherein Y is selected from chloride ion, iodide ion, bromide ion, perchlorate ion, hexafluorophosphate ion or selenate ion, and preferably chloride ion.

Further, the arene ruthenium complex has the molecular structure of:

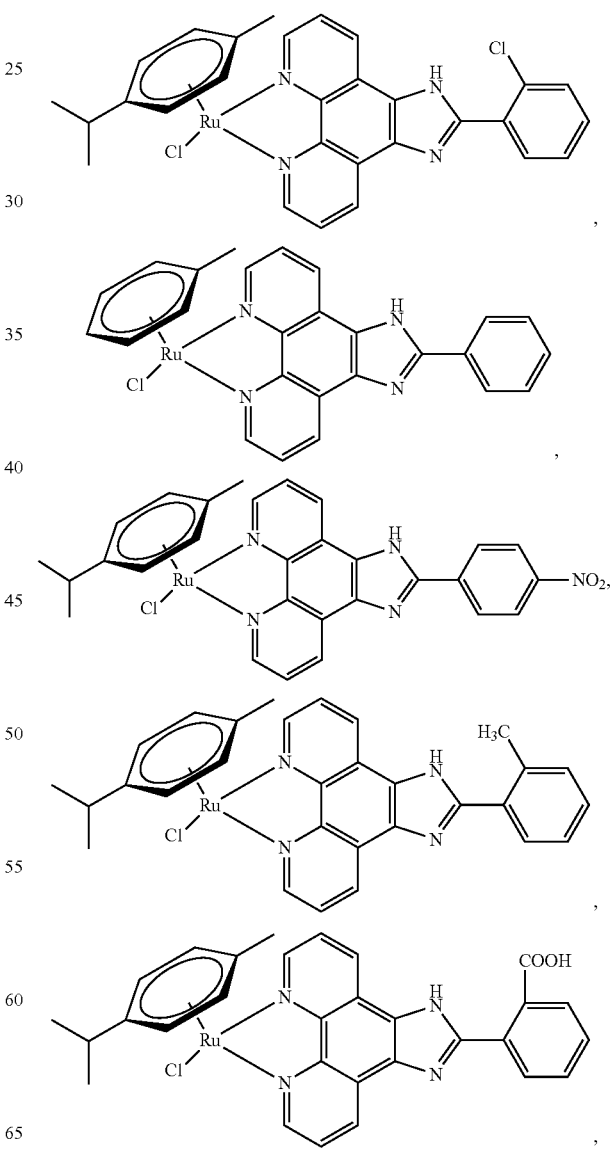

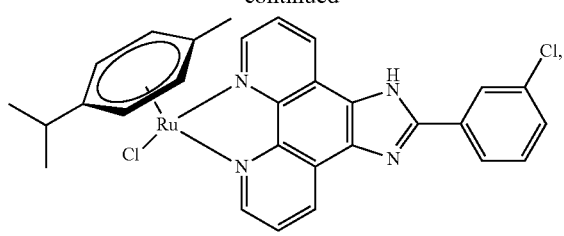
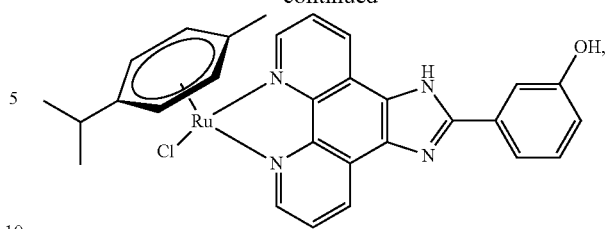
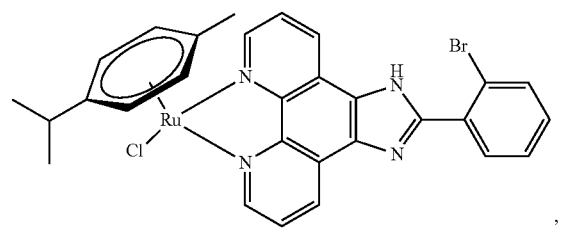
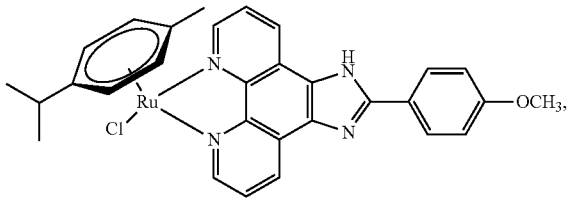
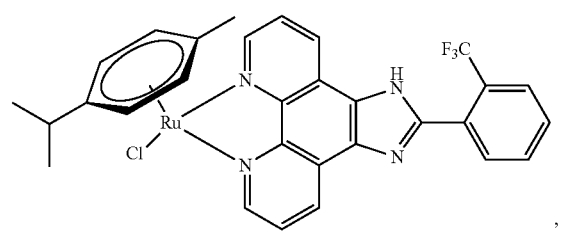
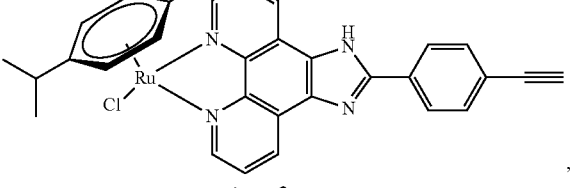
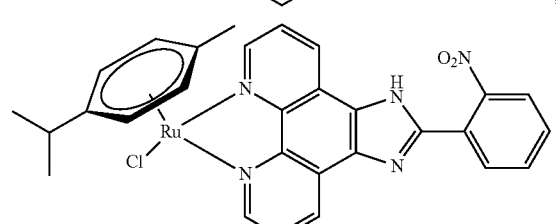
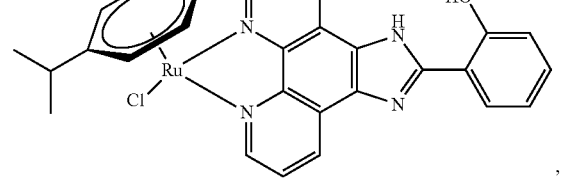
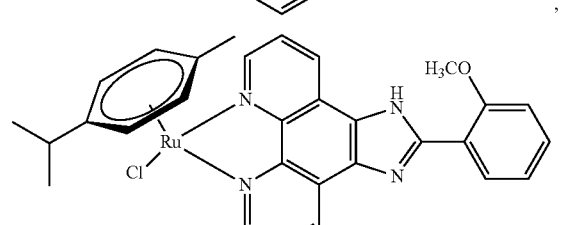
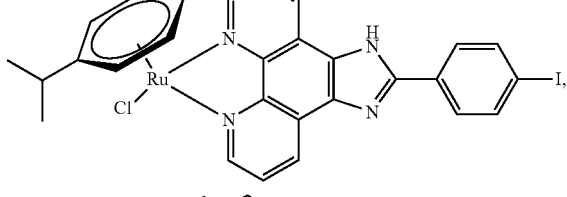
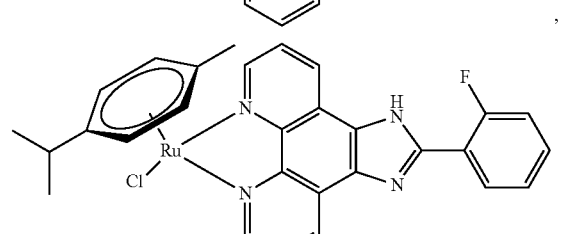
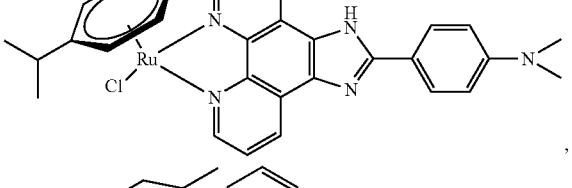
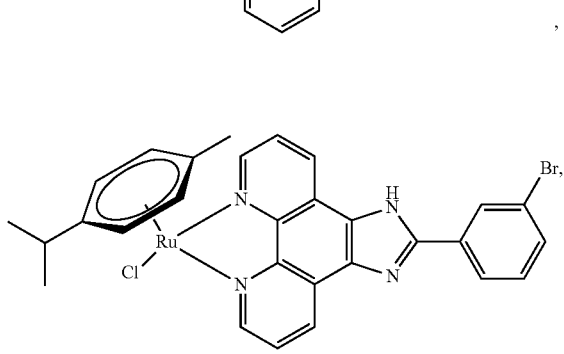
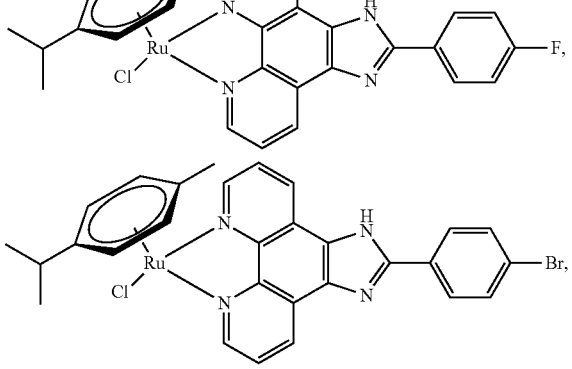

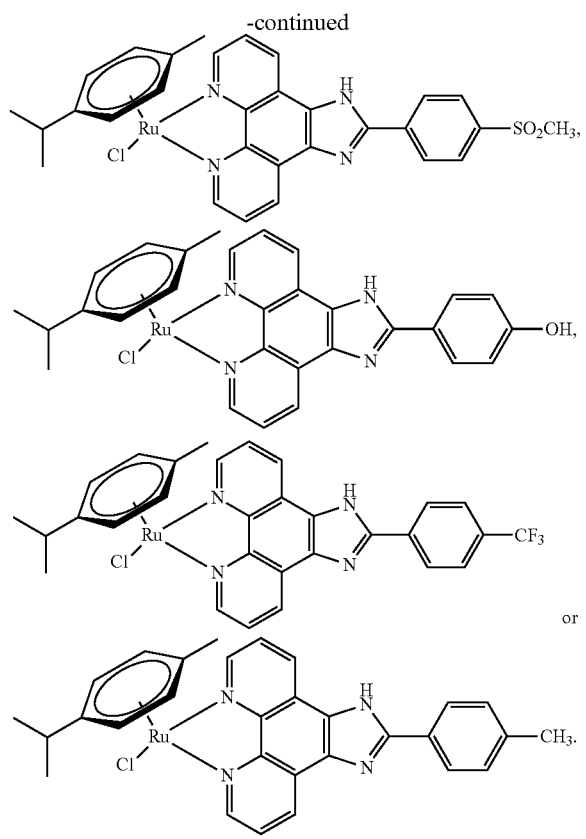

Another purpose of the invention is to provide a preparation method of the novel type of arene ruthenium complexes. The method is simple and can be generalize easily.

The preparation method of the arene ruthenium complexes is microwave-assisted synthetic method.

Further, the preparation method of the arene ruthenium complexes includes the following steps:

(1) irradiating a mixture of $RuCl_3$ and 1-methyl-4-isopropyl-1,3-cyclohexadiene with microwave at 30-180° C. for 15 seconds to 60 minutes, or refluxing the mixture at 30-180° C. for 1 hour to 7 days to obtain $[(\eta^6\text{-p-cymene})RuCl_2]_2$;

(2) adding the $[(\eta^6\text{-p-cymene})RuCl_2]_2$ and a derivative of phenanthrene imidazole into a solvent to obtain a solution, irradiating the solution with microwave at 30-180° C. for 15 seconds to 60 minutes, or refluxing the mixture at 30-180° C. for 1 hour to 7 days to obtain $[(\eta^6\text{-p-cymene})Ru(RPIP)Cl]Cl$.

Wherein in step (2), the solvent is a dichloromethane solvent.

In addition, the invention provides a utilization of the arene ruthenium complexes in inhibiting the growth of various tumors, especially in treating breast cancer, glioma cancer, leukemia, nasopharyngeal carcinoma and lung adenocarcinoma.

The novel arene ruthenium complexes of the present invention including RPIP as main ligand combined with other structures, a group of products with antitumor effects can be formed thereof. The complexes have good tumor inhibitory effect, especially in treating breast cancer, glioma cancer, leukemia, nasopharyngeal carcinoma and lung adenocarcinoma. The present invention provides a reference for the research of anti-tumor.

Besides, the present application also provide a preparation method of the novel type of arene ruthenium complexes, which is simple and can be expand production easily.

BRIEF DESCRIPTION OF THE DRAWINGS

FIG. 1 is the ESI-MS spectra of RAP051.
FIG. 2 is the $^1$H NMR spectra of RAP051.
FIG. 3 is the $^{13}$C NMR spectra of RAP051.
FIG. 4 is the ESI-MS spectra of RAP09.
FIG. 5 is the $^1$H NMR spectra of RAP09.
FIG. 6 is the $^{13}$C NMR spectra of RAP09.
FIG. 7 is the ESI-MS spectra of RAP143.
FIG. 8 is the $^1$H NMR spectra of RAP143.
FIG. 9 is the $^{13}$C NMR spectra of RAP143.
FIG. 10 is the ESI-MS spectra of RAP271.
FIG. 11 is the $^1$H NMR spectra of RAP271.
FIG. 12 is the $^{13}$C NMR spectra of RAP271.
FIG. 13 is the ESI-MS spectra of RAP211.
FIG. 14 is the $^1$H NMR spectra of RAP211.
FIG. 15 is the $^{13}$C NMR spectra of RAP211.
FIG. 16 is the ESI-MS spectra of RAP052.
FIG. 17 is the $^1$H NMR spectra of RAP052.
FIG. 18 is the $^{13}$C NMR spectra of RAP052.
FIG. 19 is the ESI-MS spectra of RAP061.
FIG. 20 is the $^1$H NMR spectra of RAP061.
FIG. 21 is the $^{13}$C NMR spectra of RAP061.
FIG. 22 is the ESI-MS spectra of RAP031.
FIG. 23 is the $^1$H NMR spectra of RAP031.
FIG. 24 is the $^{13}$C NMR spectra of RAP031.
FIG. 25 is the ESI-MS spectra of RAP141.
FIG. 26 is the $^1$H NMR spectra of RAP141.
FIG. 27 is the $^{13}$C NMR spectra of RAP141.
FIG. 28 is the ESI-MS spectra of RAP201.
FIG. 29 is the $^1$H NMR spectra of RAP201.
FIG. 30 is the $^{13}$C NMR spectra of RAP201.
FIG. 31 is the ESI-MS spectra of RAP041.
FIG. 32 is the $^1$H NMR spectra of RAP041.
FIG. 33 is the $^{13}$C NMR spectra of RAP041.
FIG. 34 is the ESI-MS spectra of RAP062.
FIG. 35 is the $^1$H NMR spectra of RAP062.
FIG. 36 is the $^{13}$C NMR spectra of RAP062.
FIG. 37 is the ESI-MS spectra of RAP032.
FIG. 38 is the $^1$H NMR spectra of RAP032.
FIG. 39 is the $^{13}$C NMR spectra of RAP032.
FIG. 40 is the ESI-MS spectra of RAP203.
FIG. 41 is the $^1$H NMR spectra of RAP203.
FIG. 42 is the $^{13}$C NMR spectra of RAP203.
FIG. 43 is the ESI-MS spectra of RAP01.
FIG. 44 is the $^1$H NMR spectra of RAP01.
FIG. 45 is the $^{13}$C NMR spectra of RAP01.
FIG. 46 is the ESI-MS spectra of RAP13.
FIG. 47 is the $^1$H NMR spectra of RAP13.
FIG. 48 is the $^{13}$C NMR spectra of RAP13.
FIG. 49 is the ESI-MS spectra of RAP073.
FIG. 50 is the $^1$H NMR spectra of RAP073.
FIG. 51 is the $^{13}$C NMR spectra of RAP073.
FIG. 52 is the ESI-MS spectra of RAP093.
FIG. 53 is the $^1$H NMR spectra of RAP093.
FIG. 54 is the $^{13}$C NMR spectra of RAP093.
FIG. 55 is the ESI-MS spectra of RAP04.
FIG. 56 is the $^1$H NMR spectra of RAP04.
FIG. 57 is the $^{13}$C NMR spectra of RAP04.
FIG. 58 is the ESI-MS spectra of RAP07.
FIG. 59 is the $^1$H NMR spectra of RAP07.
FIG. 60 is the $^{13}$C NMR spectra of RAP07.
FIG. 61 is the ESI-MS spectra of RAP22.

FIG. 62 is the $^1$H NMR spectra of RAP22.
FIG. 63 is the $^{13}$C NMR spectra of RAP22.
FIG. 64 is the ESI-MS spectra of RAP33.
FIG. 65 is the $^1$H NMR spectra of RAP33.
FIG. 66 is the $^{13}$C NMR spectra of RAP33.
FIG. 67 is the ESI-MS spectra of RAP83.
FIG. 68 is the $^1$H NMR spectra of RAP83.
FIG. 69 is the $^{13}$C NMR spectra of RAP83.
FIG. 70 is the ESI-MS spectra of RAP27.
FIG. 71 is the $^1$H NMR spectra of RAP27.
FIG. 72 is the $^{13}$C NMR spectra of RAP27.
FIG. 73 is a comparison chart of the antimigration ability of arene ruthenium (II) complex RAP07 against MDA-MB-231 cells in Embodiment 36.
FIG. 74 is a comparison chart of the invasion inhibitory ability of arene ruthenium (II) complex RAP07 against MDA-MB-231 cells in Embodiment 37.
FIG. 75 is a measurement of the content of apoptotic cells with sub-diploid DNA and the effect of cell cycle distribution in Embodiment 38.

DETAILED DESCRIPTION OF THE INVENTION

In order to make the present invention more clear and intuitive to the technical personnel in this field, the invention will be further explained in detail along with the accompanying figures.

Embodiment 1

Synthesis of $[(\eta^6\text{-p-cymene})RuCl_2]_2$

RuCl$_3$ and 1-methyl-4-isopropyl-1,3-cyclohexadiene were irradiated with microwave at 50° C. for 30 min, and suction filtrated to obtain $[(\eta^6\text{-p-cymene})RuCl_2]_2$.

Embodiment 2

Synthesis of $[(\eta^6\text{-p-cymene})Ru(o\text{-ClPIP})Cl]Cl$ (RAP051)

The precursor $[(\eta^6\text{-p-cymene})RuCl_2]_2$ (0.1 mmol, 61.2 mg) obtained in Embodiment 1 and the ligand o-ClPIP (0.2 mmol, 66.1 mg) were irradiated with microwave at 60° C. for 15 s to obtain 124.5 mg bright-yellow solid, which was the $[(\eta^6\text{-p-cymene})Ru(o\text{-ClPIP})Cl]Cl$ (RAP051). The yield was 97.9%.
The ESI-MS, $^1$H NMR and $^{13}$C NMR spectra of RAP051 are shown in FIGS. 1-3. ESI-MS (in MeOH, m/z): 636 (Cal.). 601 (Found for [M-Cl]$^+$), 565 (Found for [M-2Cl—H]$^+$). $^1$H NMR (500 MHz, DMSO-d$^6$) δ 9.89 (d, J=5.2 Hz, 1H), 9.32 (d, J=8.1 Hz, 1H), 8.20 (dd, J=8.2, 5.3 Hz, 1H), 8.01 (s, 1H), 7.69 (dd, J=23.2, 8.0 Hz, 1H), 7.63-7.55 (m, 1H), 6.37 (d, J=6.2 Hz, 1H), 6.13 (d, J=6.2 Hz, 1H), 2.23 (d, J=9.5 Hz, 1H), 1.47-1.06 (m, 1H), 0.91 (d, J=6.9 Hz, 3H). $^{13}$C NMR (126 MHz, DMSO-d$^6$) δ 154.24 (s), 152.11-148.43 (m), 143.64 (s), 134.16-132.32 (m), 131.98 (s), 130.89 (s), 130.55 (d, J=85.9 Hz), 127.95 (s), 126.70 (s), 104.28 (s), 103.57 (s), 86.73 (s), 84.38 (s), 22.13 (s), 18.77 (s).

Embodiment 3

Synthesis of $[(\eta^6\text{-p-cymene})Ru(PIP)Cl]Cl$ (RAP09)

The precursor $[(\eta^6\text{-p-cymene})RuCl_2]_2$ (0.1 mmol, 61.2 mg) obtained in Embodiment 1 and the ligand PIP (0.2 mmol, 59.2 mg) were irradiated at 60° C. with microwave for 30 min to obtain 113 mg yellow solid, which was the $[(\eta^6\text{-p-cymene})Ru(PIP)Cl]Cl$ (RAP09). The yield was 91.0%.
ESI-MS (in MeOH, m/z): 592 (Cal.). 567 (Found for [M-Cl]$^+$). $^1$H NMR (500 MHz, DMSO-d$^6$) δ 9.85 (d, J=5.2 Hz, 1H), 9.45 (s, 1H), 8.48 (d, J=7.9 Hz, 1H), 8.19 (dd, J=8.1, 5.3 Hz, 1H), 7.59 (dd, J=20.7, 13.2 Hz, 1H), 7.55 (dd, J=20.2, 13.0 Hz, 1H), 6.35 (d, J=6.2 Hz, 1H), 6.12 (d, J=6.2 Hz, 1H), 2.82-2.52 (m, 1H), 2.23 (d, J=19.7 Hz, 2H), 1.30-1.06 (m, 1H), 0.89 (t, J=15.6 Hz, 3H). $^{13}$C NMR (126 MHz, DMSO-d$^6$) δ 153.53 (s), 143.02 (s), 132.60 (s), 130.03 (s), 128.99 (s), 126.74 (s), 126.05 (s), 103.79 (s), 102.91 (s), 86.19 (s), 83.91 (s), 73.23-27.78 (m), 21.53 (d, J=16.7 Hz), 18.24 (s).

Embodiment 4

Synthesis of $[(\eta^6\text{-p-cymene})Ru(p\text{-NO}_2\text{PIP})Cl]Cl$ (RAP143)

The precursor $[(\eta^6\text{-p-cymene})RuCl_2]_2$ (0.1 mmol, 61.2 mg) obtained in Embodiment 1 and the ligand p-NO$_2$PIP (0.2 mmol, 68.2 mg) were irradiated at 60° C. with microwave for 60 min to obtain 61.2 mg yellow solid, which was $[(\eta^6\text{-p-cymene})Ru(p\text{-NO}_2\text{PIP})Cl]Cl$ (RAP143). The yield was 96.05%.
ESI-MS (in MeOH, m/z): 647 (Cal.), 612 (Found for [M-Cl]$^+$), 576 (Found for [M-2Cl-H]$^+$). $^1$H NMR (500 MHz, DMSO) δ 9.88 (d, J=4.8 Hz, 2H), 9.41 (s, 2H), 8.69 (d, J=8.8 Hz, 2H), 8.42 (d, J=8.9 Hz, 2H), 8.19 (dd, J=8.2, 5.3 Hz, 2H), 6.36 (d, J=6.4 Hz, 2H), 6.14 (d, J=6.3 Hz, 2H). $^{13}$C NMR (126 MHz, DMSO) δ 154.44 (s), 148.27 (s), 143.96 (s), 133.25 (s), 128.09 (s), 126.73 (s), 124.80 (s), 104.48 (s), 103.32 (s), 86.68 (s), 84.50 (s), 30.90 (s), 22.12 (s), 18.72 (s).

Embodiment 5

Synthesis of $[(\eta^6\text{-p-cymene})Ru(o\text{-CH}_3\text{PIP})Cl]Cl$ (RAP271)

The precursor $[(\eta^6\text{-p-cymene})RuCl_2]_2$ (0.1 mmol, 61.2 mg) obtained in Embodiment 1 and the ligand o-CH$_3$PIP (0.2 mmol, 62.0 mg) were irradiated at 30° C. with microwave for 30 min to obtain 118.5 mg yellow solid, which was RAP271. The yield was 96.2%.
ESI-MS (in MeOH, m/z): 616 (Cal.), 581 (Found for [M-Cl]$^+$). $^1$H NMR (500 MHz, DMSO) δ 9.88 (dd, J=5.2, 0.8 Hz, 2H), 9.39 (s, 1H), 8.20 (dd, J=8.2, 5.3 Hz, 1H), 7.99 (d, J=7.3 Hz, 1H), 7.48-7.38 (m, 1H), 6.37 (d, J=6.4 Hz, 1H), 6.13 (d, J=6.3 Hz, 1H). $^{13}$C NMR (126 MHz, DMSO) δ 153.66 (s), 143.02 (s), 137.21 (s), 132.57 (s), 131.35 (s), 129.80 (s), 126.08 (d, J=13.1 Hz), 126.08 (d, J=13.1 Hz), 103.77 (s), 103.41 (d, J=91.3 Hz), 103.04 (s), 86.22 (s), 85.04 (d, J=295.9 Hz), 83.87 (s), 30.38 (s), 21.63 (s), 21.08 (s), 18.27 (s).

Embodiment 6

Synthesis of $[(\eta^6\text{-p-cymene})Ru(o\text{-COOHPIP})Cl]Cl$ (RAP211)

The precursor $[(\eta^6\text{-p-cymene})RuCl_2]_2$ (0.1 mmol, 61.2 mg) and obtained in Embodiment 1 and the ligand o-COOHPIP (0.2 mmol, 68.0 mg) were irradiated at 60° C. with microwave for 30 min to obtain 110.8 mg yellow solid, which was the [(η⁶-p-cymene)Ru(o-COOHPIP)Cl]Cl (RAP211). The yield was 85.8%.

ESI-MS (in MeOH, m/z): 646 (Cal.), 611 (Found for [M-Cl]⁺), ¹H NMR (500 MHz, DMSO) δ 9.88 (dd, J=5.3, 1.1 Hz, 2H), 9.21 (d, J=8.1 Hz, 2H), 8.20 (dd, J=8.3, 5.3 Hz, 2H), 8.09 (d, J=7.5 Hz, 2H), 8.00 (dd, J=7.7, 1.1 Hz, 1H), 7.74 (td, J=7.6, 1.3 Hz, 2H), 7.67 (td, J=7.6, 1.2 Hz, 2H). ¹³C NMR (126 MHz, DMSO) δ 168.97 (s), 154.14 (s), 153.84 (s), 143.48 (s), 133.81 (s), 133.81 (s), 132.70 (s), 132.70 (s), 131.54 (s), 131.54 (s), 130.95 (s), 130.80 (s), 130.31 (d, J=7.9 Hz), 130.31 (d, J=7.9 Hz), 126.71 (s), 104.34 (s), 103.46 (s), 86.84 (s), 86.72 (s), 85.98 (s), 84.40 (s), 49.06 (s), 30.89 (s), 22.14 (s), 18.54 (d, J=51.5 Hz).

Embodiment 7

Synthesis of [(η⁶-p-cymene)Ru(m-ClPIP)Cl]Cl (RAP052)

The precursor [(η⁶-p-cymene)RuCl₂]₂ (0.1 mmol, 61.2 mg) obtained in Embodiment 1 and the ligand m-ClPIP (0.2 mmol, 66.1 mg) were irradiated at 180° C. by microwave for 30 min to obtain 124.5 mg bright-yellow solid, which was [(η⁶-p-cymene)Ru(m-ClPIP)Cl]Cl (RAP052). The yield was 97.9%.

ESI-MS (in MeOH, m/z): 636 (Cal.), 601 (Found for [M-Cl]⁺), 565 (Found for [M-2Cl—H]⁺). ¹H NMR (500 MHz, DMSO-d⁶). δ 9.85 (d, J=5.2 Hz, 1H), 9.33 (d, J=85.0 Hz, 1H), 8.53 (s, 1H), 8.42 (t, J=24.6 Hz, 1H), 8.19 (dd, J=8.1, 5.3 Hz, 1H), 8.07-8.04 (m, 1H), 7.80-7.49 (m, 1H), 6.35 (d, J=6.1 Hz, 2H), 6.13 (s, 2H), 2.69-2.52 (m, 1H), 2.23 (d, J=21.0 Hz, 3H), 0.89 (t, J=16.2 Hz, 6H). ¹³C NMR (126 MHz, DMSO-d⁶) δ 153.55 (s), 153.55 (s), 143.12 (s), 143.12 (s), 133.78 (s), 132.57 (s), 130.93 (s), 130.14-129.64 (m), 126.10 (d, J=11.6 Hz), 125.22 (s), 103.81 (s), 102.87 (s), 86.26 (d, J=19.7 Hz), 83.93 (s), 30.16 (d, J=55.3 Hz), 21.54 (d, J=17.4 Hz), 18.23 (s).

Embodiment 8

Synthesis of [(η⁶-p-cymene)Ru(o-BrPIP)Cl]Cl (RAP061)

The precursor [(η⁶-p-cymene)RuCl₂]₂ (0.1 mmol, 61.2 mg) obtained in Embodiment 1 and the ligand o-BrPIP (0.2 mmol, 74.8 mg) were irradiated at 60° C. with microwave for 30 min to obtain 127 mg bright-yellow solid, which was [(η⁶-p-cymene)Ru(o-BrPIP)Cl]Cl (RAP061). The yield was 93.4%.

ESI-MS (in MeOH, m/z): 680 (Cal.), 645 (Found for [M-Cl]⁺), 609 (Found for [M-2Cl—H]⁺). ¹H NMR (500 MHz, DMSO-d⁶) δ 9.90 (d, J=5.2 Hz, 2H), 9.30 (d, J=6.7 Hz, 2H), 8.24 (dd, J=26.7, 8.3, 5.2 Hz, 2H), 7.89 (dd, J=7.7, 3.6 Hz, 2H), 7.63 (t, J=7.5 Hz, H), 7.54 (dd, J=15.5, 7.8 Hz, H), 6.38 (d, J=6.2 Hz, 2H), 6.32-6.10 (m, 2H), 2.70-2.58 (m, 1H), 2.51 (s, 3H), 0.93 (t, J=10.9 Hz, 6H). ¹³C NMR (126 MHz, DMSO-d⁶) δ 153.91 (s), 151.88 (s), 143.19 (s), 132.97 (d, J=127.9 Hz), 132.42 (d, J=8.0 Hz), 131.60 (s), 127.92 (s), 126.31 (s), 121.87 (s), 103.88 (s), 103.04-98.30 (m), 86.23 (s), 83.90 (s), 30.38 (s), 21.65 (s), 18.26 (s).

Embodiment 9

Synthesis of [(η⁶-p-cymene)Ru(o-CF₃PIP)Cl]Cl (RAP031)

The precursor [(η⁶-p-cymene)RuCl₂]₂ (0.1 mmol, 61.2 mg) obtained in Embodiment 1 and the ligand o-CF₃PIP (0.2 mmol, 72.8 mg) were irradiated at 60° C. with microwave for 30 min to obtain 127.0 mg green solid (127.0 mg), which was [(η⁶-p-cymene)Ru(o-CF₃PIP)Cl]Cl (RAP031). The yield was 94.8%.

ESI-MS (in MeOH, m/z): 670 (Cal.), 635 (Found for [M-Cl]⁺). ¹H NMR (500 MHz, DMSO-d⁶) δ 9.96-9.56 (m, 2H), 9.25 (t, J=15.9 Hz, 1H), 8.28-8.11 (m, 2H), 8.01 (d, J=7.9 Hz, 1H), 7.95-7.87 (m, 1H), 7.85-7.77 (m, 1H), 6.38 (t, J=8.6 Hz, 1H), 6.14 (t, J=10.1 Hz, 1H), 2.64 (td, J=13.9, 7.1 Hz, 1H), 2.26-2.15 (m, 2H), 0.93 (d, J=6.9 Hz, 4H). ¹³C NMR (126 MHz, DMSO-d⁶) δ 153.71 (s), 143.13 (s), 132.56-132.09 (m), 126.82 (s), 126.23 (s), 103.89 (s), 102.94 (s), 86.27 (d, J=16.9 Hz), 83.90 (s), 30.39 (s), 21.65 (s), 18.24 (s).

Embodiment 10

Synthesis of [(η⁶-p-cymene)Ru(o-NO₂PIP)Cl]Cl (RAP141)

The precursor [(η⁶-p-cymene)RuCl₂]₂ (0.1 mmol, 61.2 mg) obtained in Embodiment 1 and the ligand o-NO₃PIP (0.2 mmol, 68.2 mg) were irradiated at 60° C. with microwave for 30 min to obtain 122.5 mg yellow solid, which was [(η⁶-p-cymene)Ru(o-NO₂PIP)Cl]Cl (RAP141). The yield was 94.7%.

ESI-MS (in MeOH, m/z): 647 (Cal.), 612 (Found for [M-Cl]⁺), 576 (Found for [M-2Cl—H]⁺). ¹H NMR (500 MHz, DMSO) δ 9.86 (dd, J=9.2, 8.6 Hz, 2H), 9.24 (d, J=6.6 Hz, 2H), 8.29 (dd, J=7.8, 1.2 Hz, 2H), 8.17 (dd, J=8.2, 5.3 Hz, 2H), 8.05 (d, J=8.0 Hz, 2H), 7.96-7.85 (m, 2H), 7.81-7.74 (m, 2H), 6.35 (d, J=6.4 Hz, 2H), 6.11 (d, J=6.4 Hz, 2H). ¹³C NMR (126 MHz, DMSO) δ 156.03 (s), 150.83 (s), 145.31 (s), 134.78 (s), 133.31 (s), 128.35 (s), 126.45 (s), 105.95 (s), 105.03 (s), 88.24 (s), 85.93 (s).

Embodiment 11

Synthesis of [(η⁶-p-cymene)Ru(o-OCH₃PIP)Cl]Cl (RAP201)

The precursor [(η⁶-p-cymene)RuCl₂]₂ (0.1 mmol, 61.2 mg) obtained in Embodiment 1 and the ligand o-OCH₃PIP (0.2 mmol, 65.2 mg) were irradiated at 60° C. with microwave for 30 min to obtain 118.6 mg yellow solid, which was [(η⁶-p-cymene)Ru(o-OCH₃PIP)Cl]Cl (RAP201). The yield was 93.8%.

ESI-MS (in MeOH, m/z): 647 (Cal.), 632 (Found for [M-Cl]⁺), 561 (Found for [M-2Cl—H]⁺). ¹H NMR (500 MHz, DMSO) δ 9.88 (dd, J=5.3, 1.2 Hz, 2H), 9.43 (s, 2H), 8.20 (ddd, J=13.3, 7.9, 3.4 Hz, 2H), 8.20 (ddd, J=13.6, 8.0, 3.5 Hz, 2H), 7.55 (ddd, J=8.4, 7.3, 1.8 Hz, 2H), 7.40-7.24 (m, 2H), 7.18 (td, J=7.6, 1.0 Hz, 2H), 6.36 (d, J=6.5 Hz, 2H), 6.13 (d, J=6.4 Hz, 2H). ¹³C NMR (126 MHz, DMSO) δ 158.76 (s), 155.75 (s), 152.81 (s), 145.05 (s), 134.73 (s), 134.73 (s), 133.89 (s), 128.07 (s), 122.89 (s), 120.04 (s), 114.12 (s), 105.84 (s), 105.00 (s), 88.30 (d, J=15.5 Hz), 85.96 (s), 58.04 (s), 41.81 (dt, J=26.5, 12.5 Hz), 41.47 (d, J=12.9 Hz), 41.36 (s), 41.23 (s), 41.11 (d, J=21.0 Hz), 32.40 (s), 23.56 (d, J=17.8 Hz), 20.28 (s).

Embodiment 12

Synthesis of [(η⁶-p-cymene)Ru(o-FPIP)Cl]Cl (RAP041)

The precursor [(η⁶-p-cymene)RuCl₂]₂ (0.1 mmol, 61.2 mg) obtained in Embodiment 1 and the ligand o-FPIP (0.2 mmol, 62.8 mg) were irradiated at 60° C. with microwave for 30 min to obtain 112.3 mg yellow solid, which was [($\eta^6$-p-cymene)Ru(o-FPIP)Cl]Cl (RAP041). The yield was 90.5%.

ESI-MS (in MeOH, m/z): 620 (Cal.), 585 (Found for [M-Cl]$^+$), 549 (Found for [M-2Cl—H]$^+$). $^1$H NMR (500 MHz, DMSO) δ 9.87 (dd, J=5.3, 1.2 Hz, 2H), 9.40 (d, J=7.3 Hz, 2H), 8.31 (td, J=7.7, 1.7 Hz, 1H), 8.19 (dd, J=8.3, 5.3 Hz, 2H), 7.61 (tdd, J=7.1, 5.1, 1.8 Hz, 1H), 7.54-7.37 (m, 2H). $^{13}$C NMR (126 MHz, DMSO) δ 162.32 (s), 155.81 (s), 155.81 (s), 150.72 (s), 145.20 (s), 134.67 (s), 134.67 (s), 134.15 (s), 132.69 (s), 132.69 (s), 128.19 (s), 128.19 (s), 127.07 (s), 120.15 (s), 118.67 (d, J=21.4 Hz), 105.83 (s), 105.83 (s), 105.05 (s), 105.05 (s), 88.30 (d, J=13.7 Hz), 88.25 (s), 87.50 (s), 85.93 (s), 85.93 (s), 42.53-41.51 (m), 41.51-41.43 (m), 41.36 (s), 41.19 (s), 41.02 (s), 32.40 (s), 23.56 (d, J=17.7 Hz), 20.28 (s), 19.86 (s).

Embodiment 13

Synthesis of [($\eta^6$-p-cymene)Ru(m-BrPIP)Cl]Cl (RAP062)

The precursor [($\eta^6$-p-cymene)RuCl$_2$]$_2$ (0.1 mmol, 61.2 mg) obtained in Embodiment 1 and the ligand m-BrPIP (0.2 mmol, 74.8 mg) were irradiated at 60° C. with microwave for 30 min to obtain 126.0 mg bright-yellow solid, which was [($\eta^6$-p-cymene)Ru(m-BrPIP)Cl]Cl (RAP062). The yield was 92.6%.

ESI-MS (in MeOH, m/z): 680 (Cal.), 645 (Found for [M-Cl]$^+$). $^1$H NMR (500 MHz, DMSO) δ 9.88 (dd, J=5.3, 1.1 Hz, 2H), 9.43 (s, 2H), 8.65 (t, J=1.7 Hz, 2H), 8.54-8.40 (m, 2H), 8.21 (dd, J=8.2, 5.3 Hz, 2H), 7.71 (ddd, J=8.0, 1.9, 0.8 Hz, 1H), 7.54 (t, J=7.9 Hz, 2H), 6.36 (d, J=6.4 Hz, 2H), 6.13 (d, J=6.4 Hz, 2H). $^{13}$C NMR (126 MHz, DMSO) δ 154.36 (s), 143.74 (s), 133.23 (s), 131.73 (s), 129.52 (s), 126.70 (s), 126.14 (s), 122.83 (s), 104.43 (s), 103.38 (s), 86.68 (s), 84.46 (s), 30.89 (s), 22.12 (s), 18.73 (s).

Embodiment 14

Synthesis of [($\eta^6$-p-cymene)Ru(m-OHPIP)Cl]Cl (RAP032)

The precursor [($\eta^6$-p-cymene)RuCl$_2$]$_2$ (0.1 mmol, 61.2 mg) obtained in Embodiment 1 and the ligand o-OHPIP (0.2 mmol, 62.4 mg) were irradiated at 60° C. with microwave for 30 min to obtain 115.0 mg bright-yellow solid, which was RAP032. The yield was 93.0%.

ESI-MS (in MeOH, m/z): 618 (Cal.), 583 (Found for [M-Cl]$^+$), 548 (Found for [M-2Cl—H]$^+$). $^1$H NMR (500 MHz, DMSO) δ 9.85 (d, J=5.1 Hz, 2H), 9.39 (s, 2H), 8.18 (dd, J=8.2, 5.3 Hz, 2H), 7.91 (d, J=7.8 Hz, 2H), 7.84 (s, 1H), 7.39 (t, J=7.9 Hz, 2H), 6.96 (dd, J=8.0, 2.0 Hz, 2H), 6.34 (d, J=6.3 Hz, 2H), 6.12 (d, J=6.3 Hz, 2H). $^{13}$C NMR (126 MHz, DMSO) δ 158.36 (s), 153.93 (s), 143.45 (s), 133.00 (s), 130.53 (s), 126.50 (s), 118.06 (s), 117.63 (s), 113.95 (s), 104.25 (s), 103.41 (s), 86.69 (s), 84.40 (s), 30.88 (s), 22.10 (s), 18.74 (s).

Embodiment 15

Synthesis of [($\eta^6$-p-cymene)Ru(p-OCH$_3$PIP)Cl]Cl (RAP203)

The precursor [($\eta^6$-p-cymene)RuCl$_2$]$_2$ (0.1 mmol, 61.2 mg) obtained in Embodiment 1 and the ligand p-OCH$_3$PIP (0.2 mmol, 65.2 mg) were irradiated at 60° C. with microwave for 30 min to obtain 124.2 mg yellow solid, which was [($\eta^6$-p-cymene)Ru(p-OCH$_3$PIP)Cl]Cl (RAP203). The yield was 98.3%.

ESI-MS (in MeOH, m/z): 632 (Cal.), 597 (Found for [M-Cl]$^+$), 561 (Found for [M-2Cl—H]$^+$). $^1$H NMR (500 MHz, DMSO-d$^6$) δ 9.85 (dd, J=5.3, 1.0 Hz, 1H), 9.43 (s, 1H), 8.43 (d, J=8.5 Hz, 1H), 8.17 (dd, J=8.2, 5.3 Hz, 1H), 7.16 (d, J=8.9 Hz, 1H), 6.34 (d, J=6.4 Hz, 1H), 6.11 (d, J=6.4 Hz, 1H), 3.86 (s, 2H), 2.59 (tt, J=18.6, 9.2 Hz, 1H), 2.19 (s, 1H), 0.89 (d, J=6.9 Hz, 3H). $^{13}$C NMR (126 MHz, DMSO-d$^6$) δ 162.90 (s), 155.41 (d, J=43.1 Hz), 144.91 (s), 134.63 (s), 130.47-128.84 (m), 128.06 (s), 124.12 (s), 116.49 (s), 105.82 (s), 104.91 (s), 88.22 (s), 85.97 (s), 57.43 (s), 32.42 (s), 23.64 (s), 20.27 (s).

Embodiment 16

Synthesis of [($\eta^6$-p-cymene)Ru(IP)Cl]Cl (RAP01)

The precursor [($\eta^6$-p-cymene)RuCl$_2$]$_2$ (0.1 mmol, 61.2 mg) obtained in Embodiment 1 and the ligand IP (0.2 mmol, 44.0 mg) were irradiated at 60° C. with microwave for 30 min to obtain 82.9 mg yellow solid, which was [($\eta^6$-p-cymene)Ru(IP)Cl]Cl (RAP01). The yield was 78.8%.

ESI-MS (in MeOH, m/z): 526 (Cal.), 491 (Found for [M-Cl]$^+$), 455 (Found for [M-2Cl—H]$^+$). $^1$H NMR (500 MHz, DMSO) δ 9.85 (dd, J=5.3, 1.0 Hz, 1H), 9.25 (dd, J=8.2, 0.8 Hz, 1H), 8.64 (s, 1H), 8.18 (dd, J=8.2, 5.3 Hz, 1H), 6.35 (d, J=6.4 Hz, 1H). $^{13}$C NMR (126 MHz, DMSO) δ 154.02 (s), 144.36 (s), 143.50 (s), 132.79 (s), 126.61 (s), 124.17-123.68 (m), 104.30-104.21 (m), 103.54-103.33 (m), 86.70 (s), 84.38 (s), 30.87 (s), 22.10 (s), 18.73 (s).

Embodiment 17

Synthesis of [($\eta^6$-p-cymene)Ru(p-C$_2$H$_2$PIP)Cl]Cl (RAP13)

The precursor [($\eta^6$-p-cymene)RuCl$_2$]$_2$ (0.1 mmol, 61.2 mg) obtained in Embodiment 1 and the ligand p-C$_2$H$_2$PIP (0.2 mmol, 64.2 mg) were irradiated at 60° C. with microwave for 30 min to obtain 108.5 mg brown solid, which was [($\eta^6$-p-cymene)Ru(p-C$_2$H$_2$PIP)Cl]Cl (RAP13). The yield was 86.7%.

ESI-MS (in MeOH, m/z): 626 (Cal.), 591 (Found for [M-Cl]$^+$). $^1$H NMR (500 MHz, DMSO-d$^6$). $^1$H NMR (500 MHz, DMSO) δ 10.46-9.87 (m, 1H), 9.61 (d, J=8.1 Hz, 1H), 8.50-8.08 (m, 2H), 8.16-7.72 (m, 1H), 6.44 (d, J=6.2 Hz, 1H), 6.22 (d, J=6.1 Hz, 1H), 5.80 (dd, J=19.0, 6.4 Hz, 1H), 2.50 (dt, J=3.7, 1.8 Hz, 2H), 2.23 (s, 2H), 1.10-0.89 (m, 3H). $^{13}$C NMR (126 MHz, DMSO) δ 159.52 (s), 149.96 (s), 143.79 (s), 141.12 (s), 137.27 (s), 134.49 (s), 131.33 (s), 129.68 (s), 106.84 (s), 87.97 (s), 86.30 (s), 83.89-30.19 (m), 23.81 (s), 20.29 (s)

Embodiment 18

Synthesis of [($\eta^6$-p-cymene)Ru(o-OHPIP)Cl]Cl (RAP031)

The precursor [($\eta^6$-p-cymene)RuCl$_2$]$_2$ (0.1 mmol, 61.2 mg) obtained in Embodiment 1 and the ligand o-OHPIP (0.2 mmol, 62.4 mg) were irradiated at 60° C. with microwave for 30 min to obtain 115.0 mg bright-yellow solid, which was [($\eta^6$-p-cymene)Ru(o-OHPIP)Cl]Cl (RAP031). The yield was 93.0%.

ESI-MS (in MeOH, m/z): 618 (Cal.), 583 (Found for [M-Cl]$^+$), 548 (Found for [M-2Cl—H]$^+$). $^1$H NMR (500 MHz, DMSO-d$^6$)$^1$H NMR (500 MHz, DMSO) δ 10.12-9.94 (m, 1H), 9.81 (d, J=5.0 Hz, 3H), 9.39 (s, 2H), 8.52 (d, J=7.6 Hz, 1H), 8.13 (dd, J=8.0, 5.4 Hz, 2H), 7.32 (t, J=6.7 Hz, 1H), 7.03-6.97 (m, 2H), 6.34 (d, J=6.2 Hz, 2H), 6.11 (d, J=6.1 Hz, 3H). $^{13}$C NMR (126 MHz, DMSO-d$^6$) δ 157.86 (s), 143.20 (s), 132.96 (s), 126.21 (s), 119.39 (s), 117.31 (s), 103.72 (d, J=98.7 Hz), 103.33 (s), 86.75 (d, J=20.7 Hz), 84.37 (s), 30.66 (d, J=54.9 Hz), 22.08 (t, J=12.4 Hz), 18.54 (d, J=50.2 Hz).

Embodiment 19

Synthesis of [(η$^6$-p-cymene)Ru(p-IPIP)Cl]Cl (RAP073)

The precursor [(η$^6$-p-cymene)RuCl$_2$]$_2$ (0.1 mmol, 61.2 mg) obtained in Embodiment 1 and the ligand p-IPIP (0.2 mmol, 84.2 mg) were irradiated at 60° C. with microwave for 30 min to obtain 111.7 mg yellow solid, which was [(η$^6$-p-cymene)Ru(p-IPIP)Cl]Cl (RAP073). The yield was 76.7%.

ESI-MS (in MeOH, m/z): 728 (Cal.), 693 (Found for [M-Cl]$^+$), 657 (Found for [M-2Cl—H]$^+$). $^1$H NMR (500 MHz, DMSO) δ 9.85 (d, J=5.1 Hz, 2H), 9.32 (s, 2H), 8.19 (dd, J=6.3, 4.5 Hz, 2H), 8.00 (t, J=8.6 Hz, 2H), 6.35 (d, J=6.3 Hz, 2H), 6.13 (t, J=9.0 Hz, 2H). $^{13}$C NMR (126 MHz, DMSO) δ 154.89-152.55 (m), 143.55-142.52 (m), 137.91 (s), 133.35-131.58 (m), 128.42 (s), 126.41-124.64 (m), 104.31-103.57 (m), 103.27-101.94 (m), 86.20 (s), 83.91 (s), 80.30-78.86 (m), 48.57 (s), 30.38 (s), 21.60 (s), 18.24 (s).

Embodiment 20

Synthesis of [(η$^6$-p-cymene)Ru(p-N(CH$_3$)$_2$PIP)Cl]Cl (RAP093)

The precursor [(η$^6$-p-cymene)RuCl$_2$]$_2$ (0.1 mmol, 61.2 mg) obtained in Embodiment 1 and the ligand p-N(CH$_3$)$_2$PIP (0.2 mmol, 68.2 mg) were irradiated at 60° C. by microwave for 30 min to obtain 120.7 mg bright-red solid, which was [(η$^6$-p-cymene)Ru(p-N(CH$_3$)$_2$PIP)Cl]Cl (RAP093). The yield was 93.6%.

ESI-MS (in MeOH, m/z): 645 (Cal.), 610 (Found for [M-Cl]$^+$). $^1$H NMR (500 MHz, DMSO) δ 9.89 (dd, J=5.3, 1.0 Hz, 2H), 8.58 (dd, J=7.9, 1.4 Hz, 2H), 8.21 (dd, J=8.2, 5.3 Hz, 1H), 7.41-7.36 (m, 1H), 7.04 (ddd, J=15.1, 8.2, 4.2 Hz, 2H), 6.58-6.20 (m, 2H), 6.36 (d, J=6.4 Hz, 2H), 6.14 (d, J=6.4 Hz, 2H). $^{13}$C NMR (126 MHz, DMSO) δ 155.71-153.66 (m), 153.17 (s), 151.37 (s), 142.57 (s), 132.42 (s), 127.94 (s), 125.82 (s).

Embodiment 21

Synthesis of [(η$^6$-p-cymene)Ru(p-FPIP)Cl]Cl (RAP04)

The precursor [(η$^6$-p-cymene)RuCl$_2$]$_2$ (0.1 mmol, 58.3 mg) obtained in Embodiment 1 and the ligand p-FPIP (0.22 mmol, 69.1 mg) were irradiated at 60° C. with microwave for 30 min to obtain 132.5 mg yellow solid, which was [(η$^6$-p-cymene)Ru(p-FPIP)Cl]Cl (RAP04). The yield was 81.3%.

ESI-MS: m/z 585, ([M]$^+$); $^1$H NMR (500 MHz, DMSO-d$^6$) δ 9.86 (dd, J=5.3, 1.1 Hz, 1H), 9.03 (dd, J=4.3, 1.7 Hz, 1H), 8.57-8.49 (m, 1H), 8.19 (dd, J=8.2, 5.3 Hz, 1H), 7.46 (t, J=8.8 Hz, 1H), 6.35 (d, J=6.5 Hz, 1H), 6.13 (d, J=6.4 Hz, 1H), 2.21 (s, 3H), 0.91 (d, J=6.9 Hz, 6H). $^{13}$C NMR (126 MHz, DMSO-d$^6$) δ 153.66 (s), 143.10 (s), 132.63 (s), 129.18 (s), 129.11 (s), 126.15 (s), 103.90 (s), 102.95 (s), 86.26 (s), 84.02 (s), 30.47 (s), 21.69 (s), 18.31 (s).

Embodiment 22

Synthesis of [(η$^6$-p-cymene)Ru(p-BrPIP)Cl]Cl (RAP07)

The precursor [(η$^6$-p-cymene)RuCl$_2$]$_2$ (0.1 mmol, 58.3 mg) obtained in Embodiment 1 and the ligand p-BrPIP (0.22 mmol, 82.5 mg) were irradiated at 60° C. with microwave for 30 min to obtain 132.5 mg yellow solid, which was [(η$^6$-p-cymene)Ru(p-BrPIP)Cl]Cl (RAP07). The yield was 99.3%.

ESI-MS: m/z 647.1, ([M]$^+$); $^1$H NMR (500 MHz, DMSO-d$^6$) δ 9.82 (d, J=4.6 Hz, 1H), 9.31 (d, J=7.0 Hz, 1H), 8.38-8.33 (m, 1H), 8.16 (dd, J=8.2, 5.3 Hz, 1H), 7.80 (d, J=8.6 Hz, 1H), 6.33 (d, J=6.4 Hz, 1H), 6.11 (d, J=6.4 Hz, 1H), 2.20 (s, 3H), 0.88 (t, J=12.3 Hz, 6H). $^{13}$C NMR (126 MHz, DMSO-d$^6$) δ 153.28 (s), 142.98 (s), 132.38 (s), 131.99 (s), 128.53 (s), 125.99 (s), 103.72 (s), 102.95 (s), 86.23 (s), 83.93 (s), 30.42 (s), 21.63 (s), 18.28 (s).

Embodiment 23

Synthesis of [(η$^6$-p-cymene)Ru(p-SO$_2$CH$_3$PIP)Cl]Cl (RAP22)

The precursor [(η$^6$-p-cymene)RuCl$_2$]$_2$ (0.1 mmol, 58.3 mg) obtained in Embodiment 1 and the ligand p-SO$_2$CH$_3$PIP (0.22 mmol, 82.4 mg) were irradiated at 60° C. with microwave for 30 min to obtain 132.5 mg yellow solid, which was [(η$^6$-p-cymene)Ru(p-SO$_2$CH$_3$PIP)Cl]Cl (RAP22). The yield was 85.1%.

ESI-MS: m/z 645.2, ([M-Cl]$^+$); $^1$H NMR (500 MHz, DMSO-d$^6$) δ 9.88 (dd, J=5.2, 0.8 Hz, 1H), 8.73 (d, J=8.6 Hz, 1H), 8.21 (dd, J=8.1, 5.3 Hz, 1H), 8.18-8.14 (m, 1H), 6.36 (d, J=6.4 Hz, 1H), 6.13 (d, J=6.4 Hz, 1H), 3.49-3.27 (m, 3H), 2.21 (s, 3H), 0.93 (t, J=9.9 Hz, 6H). $^{13}$C NMR (126 MHz, DMSO-d$^6$) δ 153.98 (s), 143.45 (s), 127.84 (s), 127.40 (s), 126.31 (s), 86.27 (s), 84.05 (s), 43.51 (s), 30.47 (s), 21.70 (s), 18.32 (s).

Embodiment 24

Synthesis of [(η$^6$-p-cymene)Ru(p-OHPIP)Cl]Cl (RAP33)

The precursor [(η$^6$-p-cymene)RuCl$_2$]$_2$ (0.1 mmol, 58.3 mg) obtained in Embodiment 1 and the ligand p-OHPIP (0.22 mmol, 68.7 mg) were irradiated at 60° C. with microwave for 30 min to obtain 132.5 mg yellow solid, which was [(η$^6$-p-cymene)Ru(p-OHPIP)Cl]Cl (RAP33). The yield was 93.5%.

ESI-MS (in MeOH, m/z): 620 (Cal.), 567 (Found for [M-Cl]$^+$). $^1$H NMR (500 MHz, DMSO-d$^6$) δ 9.83 (d, J=4.5 Hz, 1H), 8.29 (d, J=8.7 Hz, 1H), 8.17 (dd, J=8.2, 5.3 Hz, 1H), 6.99 (d, J=8.8 Hz, 1H), 6.33 (d, J=6.4 Hz, 1H), 6.10 (d, J=6.3 Hz, 1H), 2.19 (s, 3H), 2.08 (s, 1H), 1.18 (d, J=6.9 Hz, 3H). $^{13}$C NMR (126 MHz, DMSO-d$^6$) δ 160.21 (s), 143.48 (s), 133.20 (s), 129.24 (s), 126.68 (s), 116.51 (s), 104.48 (s), 100.77 (s), 86.19 (s), 84.62 (s), 31.09 (s), 22.30 (s), 18.94 (s).

Embodiment 25

Synthesis of [(η⁶-p-cymene)Ru(p-CF₃PIP)Cl]Cl (RAP83)

The precursor [(η⁶-p-cymene)RuCl₂]₂ (0.1 mmol, 58.3 mg) obtained in Embodiment 1 and the ligand p-CF₃PIP (0.22 mmol, 80.1 mg) were irradiated at 60° C. with microwave for 30 min to obtain 32.5 mg yellow solid, which was [(η⁶-p-cymene)Ru(p-CF₃PIP)Cl]Cl (RAP83). The yield was 87.3%.

ESI-MS (in MeOH, m/z): 670 (Cal.), 635 (Found for [M-Cl]⁺). ¹H NMR (500 MHz, DMSO-d⁶) δ 9.86 (dt, J=11.9, 5.9 Hz, 1H), 8.67 (d, J=8.1 Hz, 1H), 8.18 (dd, J=8.2, 5.3 Hz, 1H), 7.95 (t, J=9.8 Hz, 1H), 6.34 (d, J=6.5 Hz, 1H), 6.13 (t, J=8.2 Hz, 1H), 2.20 (s, 1H), 1.91 (s, 1H), 0.89 (t, J=7.1 Hz, 3H). ¹³C NMR (126 MHz, DMSO-d⁶) δ 154.47 (s), 143.98 (s), 133.38 (s), 128.00 (s), 126.86 (s), 126.68 (s), 104.57 (s), 103.61 (s), 86.90 (s), 84.65 (s), 31.09 (s), 22.31 (s), 18.94 (s).

Embodiment 26

Synthesis of [(η⁶-p-cymene)Ru(p-CH₃PIP)Cl]Cl (RAP27)

The precursor [(η⁶-p-cymene)RuCl₂]₂ (0.1 mmol, 58.3 mg) obtained in Embodiment 1 and the ligand p-CH₃PIP (0.22 mmol, 68.3 mg) were irradiated at 60° C. with microwave for 30 min to obtain 132.5 mg yellow solid, which was [(η⁶-p-cymene)Ru(p-CH₃PIP)Cl]Cl (RAP27). The yield was 91.2%.

ESI-MS (in MeOH, m/z): 618 (Cal.), 581 (Found for [M-Cl]⁺). ¹H NMR (500 MHz, DMSO-d⁶) δ 9.83 (dt, J=10.9, 5.5 Hz, 1H), 9.41 (s, 1H), 8.34 (t, J=9.9 Hz, 1H), 8.16 (dt, J=14.2, 7.1 Hz, 1H), 7.39 (t, J=9.8 Hz, 1H), 6.34 (t, J=10.0 Hz, 1H), 6.12 (t, J=8.2 Hz, 1H), 2.40 (s, 3H), 2.20 (s, 1H), 0.88 (t, J=6.5 Hz, 3H). ¹³C NMR (126 MHz, DMSO-d⁶) δ 154.19 (s), 143.64 (s), 140.55 (s), 133.26 (s), 130.26 (s), 127.40 (s), 127.02 (s), 126.71 (s), 104.47 (s), 103.60 (s), 86.89 (s), 84.62 (s), 31.08 (s), 22.30 (s), 21.72 (s), 18.94 (s).

Embodiment 27

Synthesis of [(η⁶-p-cymene)Ru(p-BrPIP)Cl]PF₆

Dissolving the [(η⁶-p-cymene)Ru(p-BrPIP)Cl]Cl in methanol, adding saturated ammonium hexafluorophosphate solution to obtain precipitate, filtering, subjecting to a column chromatography to obtain the hexafluorophosphate of arene ruthenium complexes.

Embodiment 28

Synthesis of [(η⁶-p-cymene)Ru(p-BrPIP)Cl]ClO₄

Dissolving the [(η⁶-p-cymene)Ru(p-BrPIP)Cl]Cl in methanol, adding saturated sodium perchlorate solution to obtain precipitate, filtering, subjecting to a column chromatography to obtain the perchlorate of arene ruthenium complexes.

Embodiment 29

Synthesis of [(η⁶-p-cymene)Ru(p-BrPIP)Cl]SeO₃

Dissolving the [(η⁶-p-cymene)Ru(p-BrPIP)Cl]Cl in methanol, adding saturated sodium selenate solution to obtain precipitate, filtering, subjecting to a column chromatography to obtain the selenate of arene ruthenium complexes.

Embodiment 30

The Anti-Invasion Activities of Arene Ruthenium (II) Complexes Against MDA-MB-231 Breast Cancer Cells.

The anti-invasion activities of arene ruthenium (II) complexes against MDA-MB-231 breast cancer cells was evaluated by MTT assay. Discarding the medium of the MDA-MB-231 breast cancer cells in exponential growth phase, washing the cells twice with phosphate-buffered saline (PBS), dissociating into single cells by digesting with 1 mL trypsin, counting the cells. Adding fresh medium to dilute cell population to $1.5 \times 10^4$ cells/mL, inoculating into 96-well tissue culture plates ($3 \times 10^3$ cells per well) with 200 μL/well in 6 wells of each group, repeating twice, and then culturing at 37° C. in 5% CO₂ saturated humidity incubator for 16 h. After adherent cells are apparent, removing the supernatant carefully and adding DMEM media. Meanwhile, the cells were incubated with different concentrations of arene ruthenium (II) complexes with a final concentration of 5, 10, 20, 40 and 80 μM respectively and maintain the total volume at 200 μL/well. Thereafter, the cells were cultured for 72 h. At the end of incubation, 20 μL/well of MTT solution (5 mg/mL) was added and incubated for 4 h. Removing the supernatant carefully and replaced with 150 μL/well of DMSO and oscillated for 10 mins to ensure complete dissolution of the formazan crystallization. The absorbance values were measured at 490 nm using a microplate reader. Cell viability was calculated according to the following formula:

Cell viability (%)=$A_{490\ nm}$ (cells in experimental group)/$A_{490\ nm}$ (cells in control group)×100%

According to the values of cell viability, calculating the inhibitory activities (IC₅₀) of the target complex against MDA-MB-231 cells.

TABLE 1

The inhibitory effect IC₅₀ (μM) of arene ruthenium (II) complexes on MDA-MB-231 breast cancer cells

| Compd. | RAP07 | RAP083 | RAP273 | RAP093 | RAP073 | RAP062 | cis-platin |
|---|---|---|---|---|---|---|---|
| IC₅₀ | 8.33 ± 0.6 | 6.27 ± 0.29 | 9.6 ± 0.3 | 6.4 ± 0.16 | 3.2 ± 0.1 | 9.2 ± 0.3 | 17.8 ± 0.9 |

Embodiment 31

The Antiproliferative Activities of Arene Ruthenium (II) Complexes Against Rat Glioma C6 Cancer Cells.

The antiproliferative effects of arene ruthenium (II) complex against rat glioma C6 cells were evaluated by MTT assay. Discarding the medium of the rat glioma C6 cells in exponential growth phase, washing the cells twice with phosphate-buffered saline (PBS), dissociating into single cells by digesting with 1 mL trypsin, counting the cells. Adding fresh medium to dilute cell population to $1.5 \times 10^4$ cells/mL, inoculating into 96-well tissue culture plates ($3 \times 10^3$ cells per well) with 200 μL/well in 6 wells of each group, repeating twice, and then culturing at 37° C. in 5% $CO_2$ saturated humidity incubator for 16 h. After adherent cells are apparent, removing the supernatant carefully and adding DMEM media. Meanwhile, the cells were incubated with different concentrations of arene ruthenium (II) complexes with a final concentration of 5, 10, 20, 40 and 80 μM respectively, and maintain the total volume at 200 μL/well. Thereafter, the cells were cultured for 72 h. At the end of incubation, 20 μL/well of MTT solution (5 mg/mL) was added and incubated for 4 h. Removing the supernatant carefully and replaced with 150 μL/well of DMSO and oscillated for 10 min to ensure complete dissolution of the formazan crystallization. The absorbance values were measured at 490 nm using a microplate reader. Cell viability was calculated according to the following formula:

Cell viability (%)=$A_{490\ nm}$ (cells in experimental group)/$A_{490\ nm}$ (cells in control group)×100%

According to the values of cell viability, calculating the inhibitory activities ($IC_{50}$) of the target complex against rat glioma C6 cells.

TABLE 2

The inhibitory effect $IC_{50}$ (μM) of arene ruthenium(II) complexes on rat glioma C6 cancer cells

| Compd. | RAP04 | RAP07 | RAP083 | RAP031 | RAP143 | RAP062 | RAP093 | Temozolomide |
|---|---|---|---|---|---|---|---|---|
| $IC_{50}$ | 1.2 ± 0.3 | 5.6 ± 0.2 | 4.5 ± 0.07 | 5.3 ± 0.12 | 2.4 ± 0.05 | 5.4 ± 0.17 | 5.6 ± 0.11 | 258.9 ± 15.5 |

Embodiment 32

The Antiproliferative Activities of Arene Ruthenium (II) Complexes Against Nasopharyngeal Carcinoma CNE-1 Cancer Cells.

The antiproliferative effects of arene ruthenium (II) complex against nasopharyngeal carcinoma CNE-1 cells were evaluated by MTT assay. Discarding the medium of the nasopharyngeal carcinoma CNE-1 cells in exponential growth phase, washing the cells twice with phosphate-buffered saline (PBS), dissociating into single cells by digesting with 1 mL trypsin, counting the cells. Adding fresh medium to dilute cell population to $1.5 \times 10^4$ cells/mL, inoculating into 96-well tissue culture plates ($3 \times 10^3$ cells per well) with 200 μL/well in 6 wells of each group, repeating twice, and then culturing at 37° C. in 5% $CO_2$ saturated humidity incubator for 16 h. After adherent cells are apparent, removing the supernatant carefully and adding DMEM media. Meanwhile, the cells were incubated with different concentrations of arene ruthenium (II) complexes with a final concentration of 5, 10, 20, 40 and 80 μM respectively and maintain the total volume at 200 μL/well. Thereafter, the cells were cultured for 72 h. At the end of incubation, 20 μL/well of MTT solution (5 mg/mL) was added and incubated at 37° C. for 4 h. Removing the supernatant carefully and replaced with 150 μL/well of DMSO and oscillated for 10 min to ensure complete dissolution of the formazan crystallization. The absorbance values were measured at 490 nm using a microplate reader. Cell viability was calculated according to the following formula:

Cell viability (%)=$A_{490\ nm}$ (cells in experimental group)/$A_{490\ nm}$ (cells in control group)×100%

According to the values of cell viability, calculating the inhibitory activities ($IC_{50}$) of the target complex against CNE-1 cancer cells.

TABLE 3

The inhibitory effect $IC_{50}$ (μM) of arene ruthenium(II) complexes on CNE-1 cancer cells

| Compd. | RAP073 | RAP093 | RAP082 | RAP201 | RAP062 | cis-platin |
|---|---|---|---|---|---|---|
| $IC_{50}$ | 3.3 ± 0.07 | 11.9 ± 0.73 | 13.8 ± 0.4 | 17.4 ± 0.47 | 15.70 ± 0.11 | 19.1 ± 0.5 |

Embodiment 33

The Antiproliferative Activities of Arene Ruthenium (II) Complexes Against A549 Lung Adenocarcinoma Cancer Cells The antiproliferative effects of arene ruthenium (II) complex against A549 lung adenocarcinoma cells were evaluated by MTT assay. Discarded the medium of the A549 lung adenocarcinoma cells in exponential growth phase, washing the cells twice with phosphate-buffered saline (PBS), dissociating into single cells by digesting with 1 mL trypsin, counting the cells. Adding fresh medium to dilute cell population to $1.5 \times 10^4$ cells/mL, inoculating into 96-well tissue culture plates ($3 \times 10^3$ cells per well) with 200 μL/well in 6 wells of each group, repeating twice, and then culturing at 37° C. in 5% $CO_2$ saturated humidity incubator for 16 h. After adherent cells are apparent, removing the supernatant carefully and adding DMEM media. Meanwhile, the cells were incubated with different concentrations of arene ruthenium (II) complexes with a final concentration of 5, 10, 20, 40 and 80 μM respectively and maintain the total volume at 200 μL/well. Thereafter, the cells were cultured for 72 h. At the end of incubation, 20 μL/well of MTT solution (5 mg/mL) was added and incubated at 37° C. for 4 h. Removing the supernatant carefully and replaced with 150 μL/well of DMSO and oscillated for 10 min to ensure complete dissolution of the formazan crystallization. The absorbance values were measured at 490 nm using a microplate reader. Cell viability was calculated according to the following formula:

Cell viability (%)=$A_{490\ nm}$ (cells in experimental group)/$A_{490\ nm}$ (cells in control group)×100%

According to the values of cell viability, calculating the inhibitory activities ($IC_{50}$) of the target complex against A549 lung adenocarcinoma cancer cells.

TABLE 4

The inhibitory effect $IC_{50}$ (μM) of arene ruthenium(II) complexes on A549 lung adenocarcinoma cancer cells

| Compd. | RAP031 | RAP052 | RAP042 | RAP143 | RAP062 | cis-platin |
|---|---|---|---|---|---|---|
| $IC_{50}$ | 26.9 ± 0.6 | 36.6 ± 0.67 | 25.01 ± 4.3 | 11.8 ± 0.9 | 6.59 ± 2.26 | 93.1 ± 0.9 |

Embodiment 34

The Antiproliferative Activities of Arene Ruthenium (II) Complexes Against Human Esophageal Carcinoma EC-1 Cells.

The antiproliferative effects of arene ruthenium (II) complex against human esophageal carcinoma EC-1 cells were evaluated by MTT assay. Discarding the medium of human esophageal carcinoma EC-1 cells in exponential growth phase, washing the cells twice with phosphate-buffered saline (PBS), dissociating into single cells by digesting with 1 mL trypsin, counting the cells. Adding fresh medium to dilute cell population to 1.5×10⁴ cells/mL, inoculating into 96-well tissue culture plates (3×10³ cells per well) with 200 L/well in 6 wells of each group, repeating twice, and then culturing at 37° C. in 5% $CO_2$ saturated humidity incubator for 16 h. After adherent cells are apparent, removing the supernatant carefully and adding DMEM media. Meanwhile, the cells were incubated with different concentrations of arene ruthenium (II) complexes with a final concentration of 5, 10, 20, 40 and 80 μM respectively and maintain the total volume at 200 μL/well. Thereafter, the cells were cultured for 72 h. At the end of incubation, 20 μL/well of MTT solution (5 mg/mL) was added and incubated at 37° C. for 4 h. Removing the supernatant carefully and replaced with 150 μL/well of DMSO and oscillated for 10 min to ensure complete dissolution of the formazan crystallization. The absorbance values were measured at 490 nm using a microplate reader. Cell viability was calculated according to the following formula:

Cell viability (%)=$A_{490\ nm}$ (cells in experimental group)/$A_{490\ nm}$ (cells in control group)×100%

According to the values of cell viability, calculating the inhibitory activities ($IC_{50}$) of the target complex against human esophageal carcinoma EC-1 cells.

Embodiment 35

The Antiproliferative Activities of Arene Ruthenium (II) Complexes Against Human Epidermal HaCaT Cells.

The antiproliferative effects of arene ruthenium (II) complex against human epidermal HaCaT cells were evaluated by MTT assay. Discarding the medium of human epidermal HaCaT cells in exponential growth phase and washing the cells twice with phosphate-buffered saline (PBS), dissociating into single cells by digesting with 1 mL trypsin. Adding fresh medium to dilute cell population to 1.5×10⁴ cells/mL, inoculating into 96-well tissue culture plates (3×10³ cells per well) with 200 μL/well in 6 wells of each group, repeating twice, and then culturing at 37° C. in 5% $CO_2$ saturated humidity incubator for 16 h. After adherent cells are apparent, carefully removing the supernatant and adding DMEM media. Meanwhile, the cells were incubated with different concentrations of arene ruthenium (II) complexes with a final concentration of 5, 10, 20, 40 and 80 μM respectively and maintain the total volume at 200 L/well. Thereafter, the cells were cultured for 72 h. At the end of incubation, 20 μL/well of MTT solution (5 mg/mL) was added and incubated at 37° C. for 4 h. Removing the supernatant carefully and replaced with 150 μL/well of DMSO and oscillated for 10 min to ensure complete dissolution of the formazan crystallization. The absorbance values were measured at 490 nm using a microplate reader. Cell viability was calculated according to the following formula:

Cell viability (%)=$A_{490\ nm}$ (cells in experimental group)/$A_{490\ nm}$ (cells in control group)×100%

According to the values of cell viability, calculating the inhibitory activities ($IC_{50}$) of the target complex against human epidermal HaCaT cells.

TABLE 5

The inhibitory effect $IC_{50}$ (μM) of arene ruthenium(II) complexes on human esophageal carcinoma EC-1 cells

| Compd. | RAP04 | RAP07 | RAP083 | RAP273 | RAP11 | cis-platin |
|---|---|---|---|---|---|---|
| $IC_{50}$ | 18.2 ± 0.5 | 18.1 ± 1.7 | 6.9 ± 0.2 | 18.4 ± 11.7 | 34.1 ± 2.7 | 9.4 ± 0.21 |

TABLE 6

The inhibitory effect $IC_{50}$ (μM) of arene ruthenium(II) complexes on human epidermal HaCaT cells

| Compd. | RAP031 | RAP083 | RAP061 | RAP093 | RAP062 | cis-platin |
|---|---|---|---|---|---|---|
| $IC_{50}$ | >100 | >100 | >100 | >100 | 37.3 ± 1.99 | 17.1 ± 0.8 |

Embodiment 36

The Antimigration Ability of Arene Ruthenium (II) Complex RAP07 Against MDA-MB-231 Cells.

MDA-MB-231 cells were inoculated into 6-well tissue culture plates ($1\times10^5$ cells per well), wherein the plates were marked on the back with uniform horizontal line every 0.5-1 cm. The lines cross the well, and there's at least 5 lines cross through each well. After overnight culturing, the monolayer cells covered more than 80% of the bottom of the culture plate, then scratching on the bottom of the culture plate using a tip (200 μL pipet) along the mark line and perpendicular to the mark line on the plate, and washing the cells 3 times with PBS to remove the cells that were divided by scratching. Subsequently, MDA-MB-231 cells were incubated in serum free medium added with the arene ruthenium (II) complexes at different concentrations (5, 10, 20, 40 and 80 μM), and then cultured at 37° C. in 5% $CO_2$ saturated humidity incubator for 24 h. Migrating cells were observed in the same visual field every 6 h and captured under a fluorescence microscope during 24 h cultured period. The effect of different concentrations of complexes treatment is show in FIG. 73.

Embodiment 37

The Anti-Migration Ability of Arene Ruthenium (II) Complex RAP07 Against MDA-MB-231 Cells.

Taking 50 μL FITC-gelatin in a 3 cm glass dish and placing in incubator at 37° C. for 30 min to allow FITC-gelatin to fully coagulate, adding 0.5% glutaraldehyde, incubating at room temperature for 10 min in dark, quenching with 5 mg·$mL^{-1}$ freshly prepared NaBH4 at room temperature until no bubbles generated and washing 3 times with phosphate-buffered saline (PBS). Discarding the medium of the MDA-MB-231 cells in the exponential growth phase and washing the cells twice with PBS, then dissociating into single cells by digesting with 1 mL trypsin, counting the cells. Adding fresh serum free medium to dilute cell population to $1.5\times10^4$ cells/mL, inoculating into the glass dishes with 1 mL/dish. After adherent cells are apparent, carefully removing the supernatant and culturing in serum free medium added with the complexes RAP07 at different concentrations (0, 5, 10, and 20 μM) for 24 h. And finally the status of MDA-MB-231 cells perforated on FITC-gelatin was evaluated and photographed with a laser confocal microscope. The effect of different concentrations of complexes RAP07 treatment is shown in FIG. 74.

Embodiment 38

Arene Ruthenium (II) Complex RAP07 Induces the S-Phase Arrest of MDA-MB-231 Cells.

After incubating with arene ruthenium (II) complex RAP07, the cell cycle arrest of MDA-MB-231 cells was analyzed with an Epics XL-MCL flow cytometer. The general method is: Trypsinizing the cells with trypsin, washing the cells with phosphate-buffered saline (PBS), and fixing the cells with 70% ethanol overnight at −20° C. Washing the fixed cells with phosphate-buffered saline (PBS) and staining with propidium iodide (PI) for 4 hours in the dark. Finally, the cell cycle arrest was analyzed using an Epics XL-MCL flow cytometer, cell cycle distribution was analyzed using MultiCycle software (Phoenix Flow Systems, San Diego, Calif.). The number of apoptotic cells with sub-diploid DNA were determined by measuring the G1 peak in the cell cycle, every 10000 cells of each sample were recorded. The effects of different concentrations of complexes RAP07 treatment are shown in FIG. 75.

The foregoing descriptions are merely preferred embodiments of the present invention, which are not used to limit the present invention. Any modifications, equivalent substitutions, improvements within the spirit and principle of the present invention should be included in the protection scope of the present invention.

What is claimed is:

1. A salt of an arene ruthenium complex, wherein the salt of the arene ruthenium complex is represented by the following structural formula:

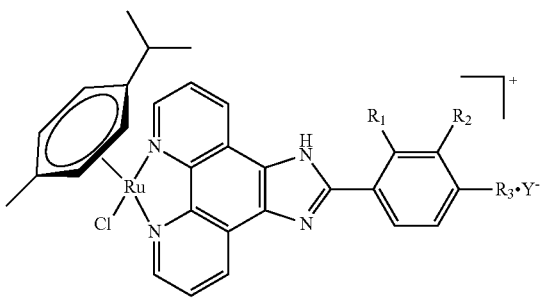

wherein the arene ruthenium complex is selected from the group consisting of:

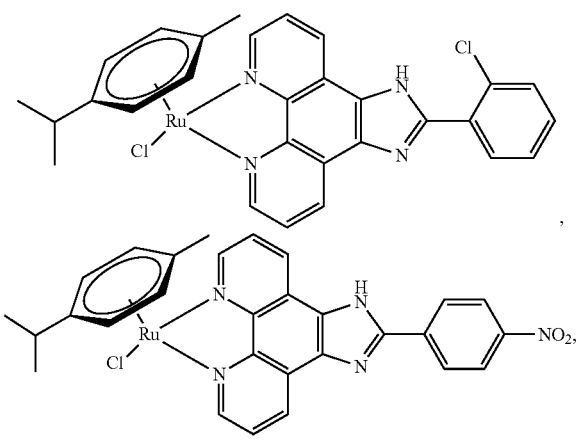

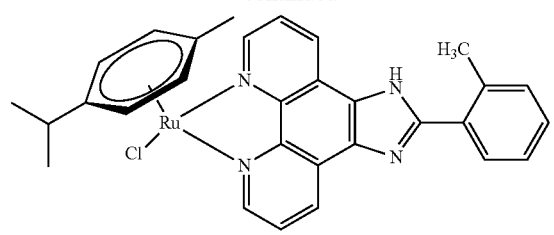
,
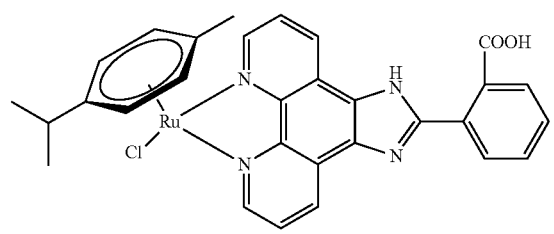
,
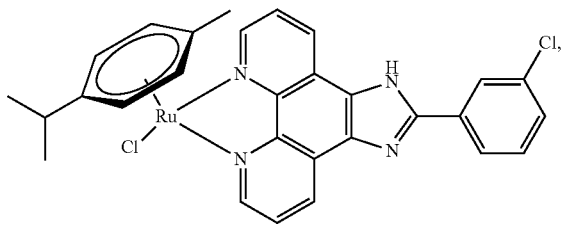
,
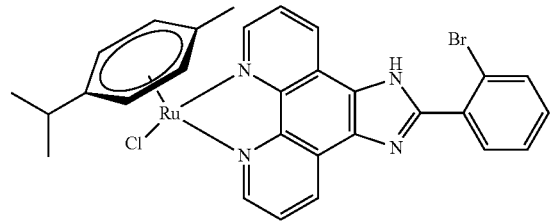
,
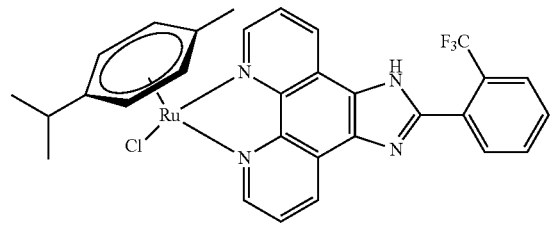
,
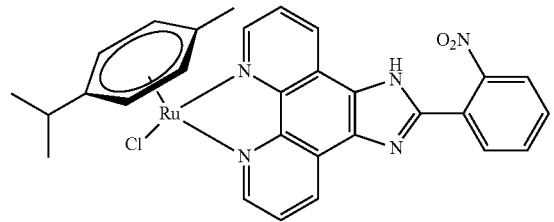
,
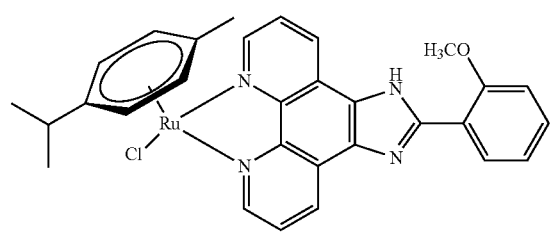
,
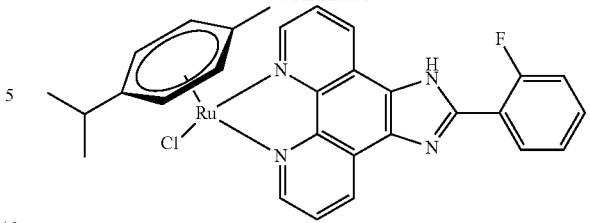
,
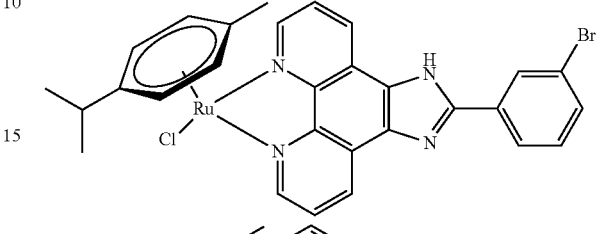
,
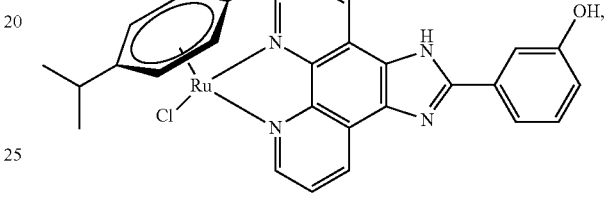
,
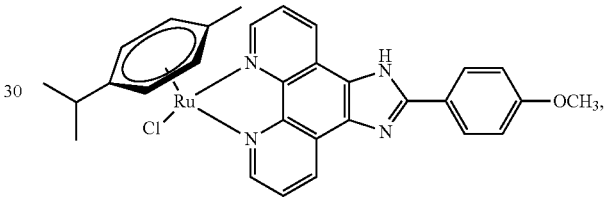
,
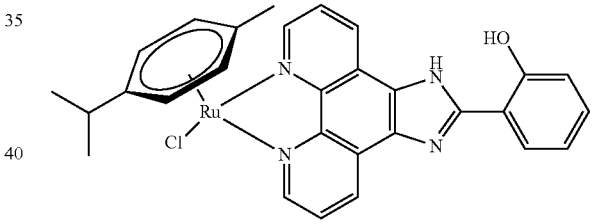
,
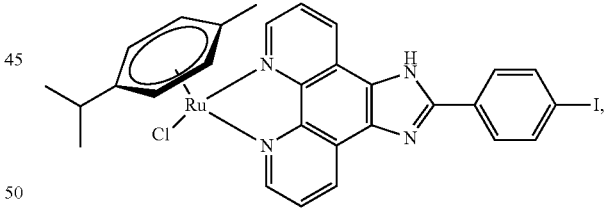
,
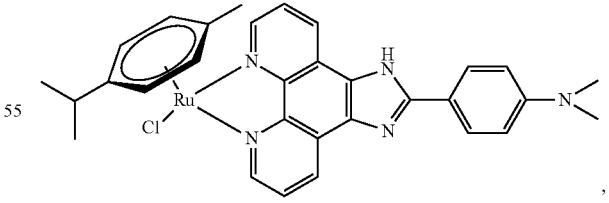
,
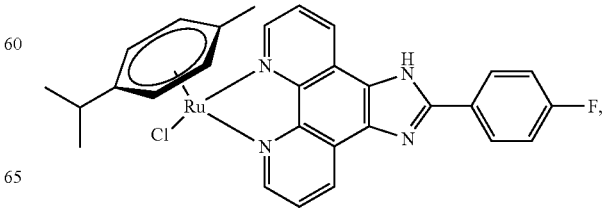
,

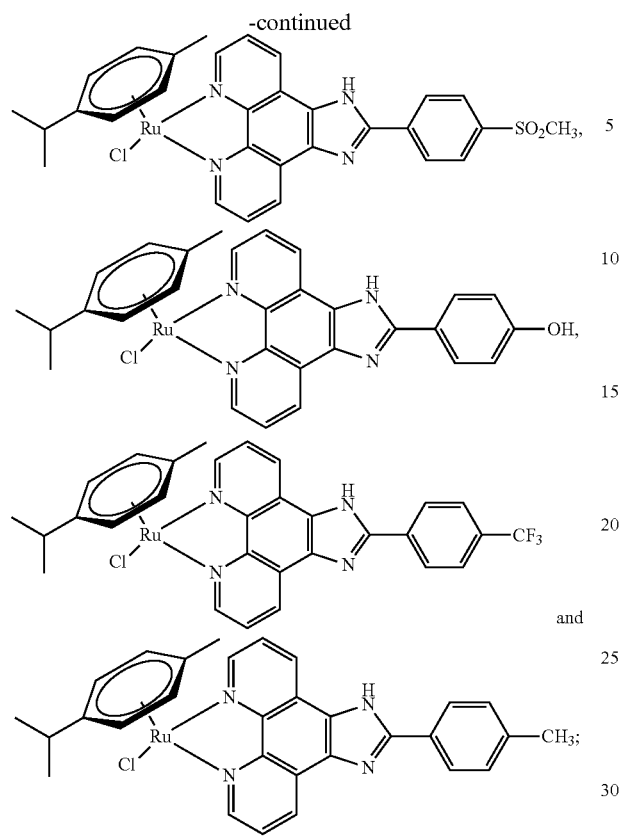

and

Y is selected from the group consisting of chloride, iodide, bromide, perchlorate, hexafluorophosphate and selenate.

2. A preparation method of the salt of the arene ruthenium complex according to claim 1, comprising the following steps:

(1) irradiating a mixture of RuCl$_3$ and 1-methyl-4-isopropyl-1,3-cyclohexadiene with microwave at 30-180° C. for 15 seconds to 60 minutes, or refluxing the mixture at 30-180° C. for 1 hour to 7 days to obtain [($\eta^6$-p-cymene)RuCl$_2$]$_2$;

(2) adding the [($\eta^6$-p-cymene)RuCl$_2$]$_2$ and an imidazole [4,5f][1,10] phenanthroline derivative into a solvent to obtain a solution, irradiating the solution with microwave at 30-180° C. for 15 seconds to 60 minutes, or refluxing the solution at 30-180° C. for 1 hour to 7 days to obtain the salt of the arene ruthenium complex;

wherein the imidazole[4,5f][1,10] phenanthroline derivative is selected from the group consisting of:

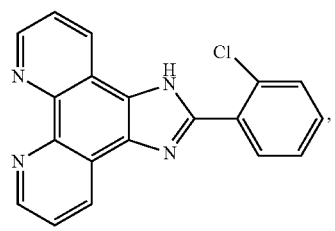

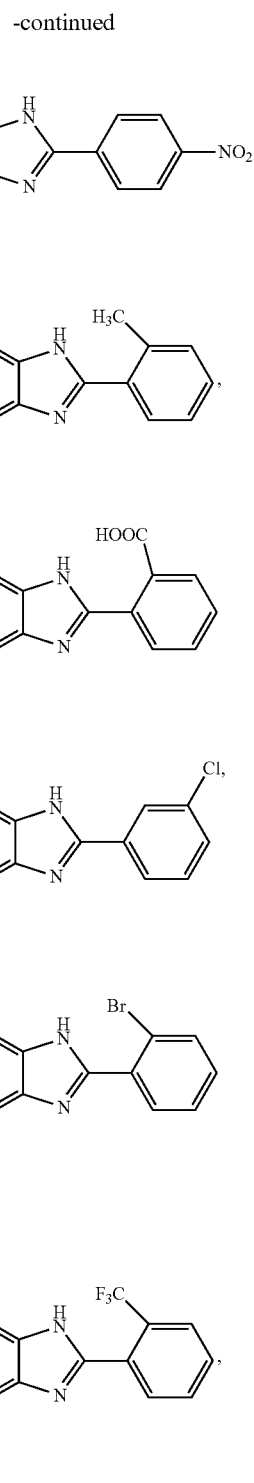

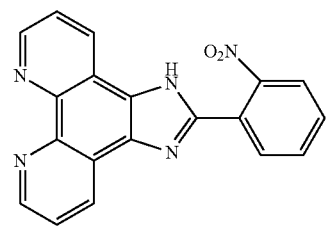

-continued
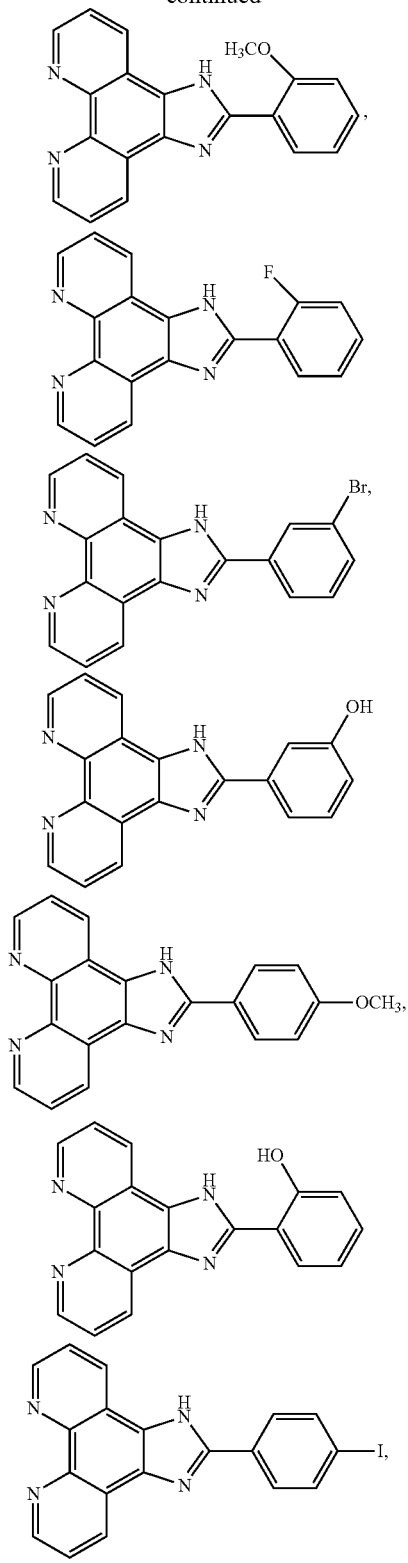
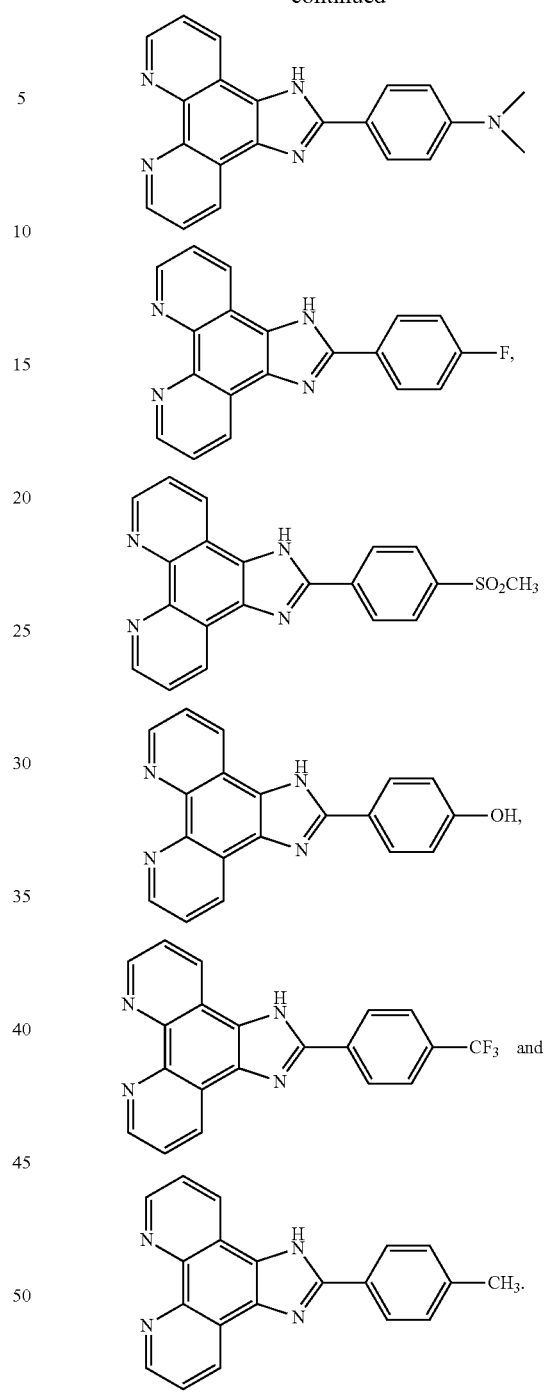
3. The preparation method of claim 2, wherein the solvent in step (2) is a dichloromethane.
* * * * *